United States Patent
Klinger

(10) Patent No.: US 10,428,325 B1
(45) Date of Patent: Oct. 1, 2019

(54) IDENTIFICATION OF ANTIGEN-SPECIFIC B CELL RECEPTORS

(71) Applicant: Adaptive Biotechnologies Corp., Seattle, WA (US)

(72) Inventor: Mark Klinger, Seattle, WA (US)

(73) Assignee: Adaptive Biotechnologies Corporation, Seattle, WA (US)

( * ) Notice: Subject to any disclaimer, the term of this patent is extended or adjusted under 35 U.S.C. 154(b) by 0 days.

(21) Appl. No.: 15/710,390

(22) Filed: Sep. 20, 2017

Related U.S. Application Data

(60) Provisional application No. 62/397,811, filed on Sep. 21, 2016.

(51) Int. Cl.
C40B 30/04 (2006.01)
C12N 15/10 (2006.01)

(52) U.S. Cl.
CPC .......... *C12N 15/1037* (2013.01); *C40B 30/04* (2013.01)

(58) Field of Classification Search
None
See application file for complete search history.

(56) References Cited

U.S. PATENT DOCUMENTS

| | | |
|---|---|---|
| 5,189,147 A | 2/1993 | Saito et al. |
| 5,213,960 A | 5/1993 | Chang |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,418,134 A | 5/1995 | Morley |
| 5,506,126 A | 4/1996 | Seed et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,925,517 A | 7/1999 | Tyagi et al. |
| 5,935,793 A | 8/1999 | Wong |
| 5,981,176 A | 11/1999 | Wallace |
| 6,087,096 A | 7/2000 | Dau et al. |
| 6,091,000 A | 7/2000 | Haynes |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

US 6,331,391 B1, 12/2001, Wittrup et al. (withdrawn)

(Continued)

*Primary Examiner* — Christian C Boesen
(74) *Attorney, Agent, or Firm* — Cooley LLP

(57) ABSTRACT

Compositions and methods are disclosed for identifying B-cell receptor sequences that bind to corresponding antigens. The disclosed methods and related embodiments permit the identification paired relationships between rearranged gene segments of B-cell receptors with unique antigens.

30 Claims, 1 Drawing Sheet
Specification includes a Sequence Listing.

(56) References Cited

U.S. PATENT DOCUMENTS

| | | |
|---|---|---|
| 6,136,566 A | 10/2000 | Sands et al. |
| 6,172,214 B1 | 1/2001 | Brenner |
| 6,207,371 B1 | 3/2001 | Zambrowicz et al. |
| 6,214,613 B1 | 4/2001 | Higuchi et al. |
| 6,228,589 B1 | 5/2001 | Brenner |
| 6,255,071 B1 | 7/2001 | Beach et al. |
| 6,258,568 B1 | 7/2001 | Nyren |
| 6,291,183 B1 | 9/2001 | Pirrung et al. |
| 6,300,065 B1 | 10/2001 | Kieke et al. |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,423,538 B1 | 7/2002 | Wittrup et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,753,147 B2 | 6/2004 | Vogelstein et al. |
| 6,787,308 B2 | 9/2004 | Balasubramanian et al. |
| 6,919,434 B1 | 7/2005 | Goto et al. |
| 6,964,850 B2 | 11/2005 | Bevilacqua |
| 6,969,597 B2 | 11/2005 | Lukyanov et al. |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,323,306 B2 | 1/2008 | Dunn et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,709,197 B2 | 5/2010 | Drmanac |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,955,794 B2 | 6/2011 | Shen et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | MacEvicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,685,898 B2 | 4/2014 | Wiley |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,279,159 B2 | 3/2016 | Robins et al. |
| 9,371,558 B2 | 6/2016 | Robins et al. |
| 9,394,567 B2 | 7/2016 | Asbury et al. |
| 9,416,420 B2 | 8/2016 | Faham et al. |
| 9,506,119 B2 | 11/2016 | Faham et al. |
| 9,512,487 B2 | 12/2016 | Faham et al. |
| 9,708,657 B2 | 7/2017 | Asbury et al. |
| 9,809,813 B2 | 11/2017 | Robins et al. |
| 10,066,265 B2 | 9/2018 | Klinger et al. |
| 10,077,473 B2 | 9/2018 | Asbury et al. |
| 10,077,478 B2 | 9/2018 | Faham et al. |
| 10,150,996 B2 | 12/2018 | Robins et al. |
| 10,155,992 B2 | 12/2018 | Faham et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0018489 A1 | 1/2004 | Ma et al. |
| 2004/0033490 A1 | 2/2004 | Laird et al. |
| 2004/0121364 A1 | 6/2004 | Chee et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | MacEvicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0275752 A1 | 7/2006 | Sindhi |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |

(56) References Cited

U.S. PATENT DOCUMENTS

| | | |
|---|---|---|
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0233802 A1 | 9/2009 | Bignell et al. |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0129874 A1 | 5/2010 | Mitra et al. |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0323355 A1 | 12/2010 | Dittmer |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0166034 A1 | 7/2011 | Kwong et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0010096 A1 | 1/2012 | Wohlgemuth et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2012/0308999 A1 | 12/2012 | Sarma et al. |
| 2013/0005584 A1 | 1/2013 | Faham |
| 2013/0017957 A1 | 1/2013 | Faham et al. |
| 2013/0045221 A1 | 2/2013 | Stauss et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0137108 A1 | 5/2013 | Tripathi et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0273647 A1 | 10/2013 | Sahin et al. |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0065629 A1 | 3/2014 | Barken et al. |
| 2014/0094376 A1 | 4/2014 | Han |
| 2014/0127699 A1 | 5/2014 | Han |
| 2014/0141982 A1 | 5/2014 | Jacobson et al. |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0227705 A1 | 8/2014 | Vogelstein et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017630 A1 | 1/2015 | Oved et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0087535 A1 | 3/2015 | Patel et al. |
| 2015/0133317 A1 | 5/2015 | Robinson et al. |
| 2015/0154352 A1 | 6/2015 | Johnson et al. |
| 2015/0167080 A1 | 6/2015 | Moorhead et al. |
| 2015/0203897 A1 | 7/2015 | Robins et al. |
| 2015/0215062 A1 | 7/2015 | Li et al. |
| 2015/0218656 A1 | 8/2015 | Kirsch et al. |
| 2015/0232936 A1 | 8/2015 | Shoemaker et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |

(56) References Cited

U.S. PATENT DOCUMENTS

| | | |
|---|---|---|
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0024493 A1 | 1/2016 | Robins et al. |
| 2016/0115532 A1 | 4/2016 | Faham |
| 2016/0138011 A1 | 5/2016 | Dewitt et al. |
| 2016/0186260 A1 | 6/2016 | Klinger et al. |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0258025 A1 | 9/2016 | Klinger et al. |
| 2016/0304956 A1 | 10/2016 | Robins et al. |
| 2016/0319340 A1 | 11/2016 | Robins et al. |
| 2017/0037469 A1 | 2/2017 | Robins et al. |
| 2017/0292149 A1 | 10/2017 | Emerson et al. |
| 2017/0335386 A1 | 11/2017 | Livingston et al. |
| 2017/0335390 A1 | 11/2017 | Asbury et al. |
| 2017/0335391 A1 | 11/2017 | Emerson et al. |
| 2017/0349954 A1 | 12/2017 | Faham et al. |
| 2018/0023143 A9 | 1/2018 | Faham et al. |
| 2018/0037953 A1 | 2/2018 | Emerson et al. |
| 2018/0073015 A1 | 3/2018 | Robins et al. |
| 2018/0080090 A1 | 3/2018 | Faham et al. |
| 2018/0087109 A1 | 3/2018 | Klinger et al. |
| 2018/0112278 A1 | 4/2018 | Faham et al. |
| 2018/0312832 A1 | 11/2018 | Robins et al. |
| 2018/0355429 A1 | 12/2018 | Klinger et al. |

FOREIGN PATENT DOCUMENTS

| | | |
|---|---|---|
| CN | 103097888 A | 5/2013 |
| EA | 007958 B1 | 2/2007 |
| EP | 0303459 A2 | 2/1989 |
| EP | 0799897 A1 | 10/1997 |
| EP | 1516929 A2 | 3/2005 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088205 A1 | 8/2009 |
| EP | 2088432 A1 | 8/2009 |
| EP | 2418287 A2 | 2/2012 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2011-505123 A | 2/2011 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013868 A1 | 4/1997 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2001/014424 A2 | 3/2001 |
| WO | WO 2002/024322 A2 | 3/2002 |
| WO | WO 2003/008624 A2 | 1/2003 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/003375 A2 | 1/2005 |
| WO | WO 2005/005651 A2 | 1/2005 |
| WO | WO 2005/010200 A2 | 2/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/008759 A2 | 1/2007 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/152928 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/083456 A1 | 7/2010 |
| WO | WO 2010/151416 A1 | 12/2010 |
| WO | WO 2011/017151 A2 | 2/2011 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/012703 A2 | 1/2012 |
| WO | WO 2012/017081 A1 | 2/2012 |
| WO | WO 2012/027503 A2 | 3/2012 |
| WO | WO 2012/048340 A2 | 4/2012 |
| WO | WO 2012/048341 A2 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/122484 A1 | 9/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/123442 A1 | 8/2013 |
| WO | WO 2013/130512 A2 | 9/2013 |
| WO | WO 2013/131074 A1 | 9/2013 |

(56) References Cited

FOREIGN PATENT DOCUMENTS

| | | |
|---|---|---|
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2014/145992 A1 | 9/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2015/134787 A2 | 9/2015 |
| WO | WO 2015/153788 A1 | 10/2015 |
| WO | WO 2015/160439 A2 | 10/2015 |
| WO | WO 2016/069886 A1 | 5/2016 |
| WO | WO 2016/138122 A1 | 9/2016 |
| WO | WO 2016/161273 A1 | 10/2016 |

OTHER PUBLICATIONS

US 8,642,750 B2, 02/2014, Faham et al. (withdrawn)
Zwick et al. (Jul. 2001) Journal of Virology vol. 75 pp. 6692 to 6699.*
Abbott, et al. "Design and use of signature primers to detect carry-over of amplified material", J Virol Methods, 46(1):51-59, Abstract Only (1994).
Ahmadzadeh et al. "FOXP3 expression accurately defines the population of intratumoral regulatory T cells that selectively accumulate in metastatic melanoma lesions", Blood, 112(13): 4953-4960 (2008).
Aird, et al., "Analyzing and minimizing PCR amplification bias in Illumina sequencing libraries." Genome Biology (2011); 12: R18, pp. 1-14.
Akamatsu, Y. et al., "Essential Residues in V(D)J Recombination Signals." The Journal of Immunology (1994); 153 (10): 4520-4529.
Akatsuka, Y. et al., "Rapid screening of T-cell receptor (TCR) variable gene usage by multiplex PCR: Application for assessment of clonal composition", Tissue Antigens, 53(2):122-134 (1999).
Alatrakchi et al. "T-cell clonal expansion in patients with B-cell lymphoproliferative disorders", Journal of Immunotherapy, 21(5):363-370 (1998).
Alexandre, D. et al. "H. sapiens rearranged T-cell receptor gamma chain gene, V2-JP1", GenBank accession No: X57737, NCBI, Nov. 14, 2006, 8 pages [online] [retrieved on Jun. 26, 2013] Retrieved from the internet <URL:http://www.ncbi.nlm.nih.gov/nuccore/x57737>.
Alexandre, D. et al. "H. sapiens rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Altman, et al. "Phenotypic analysis of antigen-specific T lymphocytes", The Journal of Immunology, 187(1):7-9 (2011).
Andreasson, et al. "The human IgE-encoding transcriptome to assess antibody repertoires and repertoire evolution", J Mol Biol., 362(2):212-227 (2006). Epub Aug. 14, 2006.
Armand, P. et al., "Detection of circulating tumour DNA in patients with aggressive B-cell non-Hodgkin lymphoma", Brit. J. Haematol., vol. 163, pp. 123-126 (2013).
Arstila, T.P., et al., "A direct estimate of the human αβ T cell receptor diversity," Science, 286(5441): 958-961 (1999).
Aslanzadeh. "Preventing PCR amplification carryover contamination in a clinical laboratory", Ann Clin Lab Sci., 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", Blood, 96(2): 640-646 (2000).
Attaf, et al., "αβ T cell receptors as predictors of health and disease." Cellular & Molecular Immunology (Jul. 2015); 12 (4): 391-399. Epub Jan. 26, 2015.
Babrzadeh et al. "Development on High-throughput Sequencing Technology: emPCR Titration and Barcode Design", Stanford School of Medicine, 2 pages (2011).
Bagnara, et al. "IgV gene intraclonal diversification and clonal evolution in B-cell chronic lymphocytic leukaemia", British Journal of Haematology, 133(1):50-58 (2006).
Barbas III, et al., "Assembly of combinatorial antibody libraries on phage surfaces: the gene III site." Proc Natl Acad Sci U S A. (Sep. 1991); 88(18): 7978-7982.
Barker, et al. "A second type II restriction endonuclease from Thermus aquaticus with an unusual sequence specificity", Nucleic Acids Res., 12(14): 5567-5581 (1984).
Barnard, et al., "PCR Bias Toward the Wild-Type k-rasand p53 Sequences: Implications for PCR Detection of Mutations and Cancer Diagnosis." BioTechniques (Oct. 1998); 25: 684-691.
Baum and McCune et al. "Direct measurement of T-cell receptor repertoire diversity with AmpliCot", Nat Methods, 3(11): 895-901 (2006).
Becton-Dickinson T-Cell Research Tools, "Novel multicolor flow cytometry tools for the study of CD4+ T-cell differentiation and plasticity", 16 pages. (2009).
Becton-Dickinson, CD marker handbook. bdbiosciences.com/go/mousecdmarkers, p. 1-47 (2010).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", Blood, 83(8):2238-2247 (1994).
Béné and Kaeda, "How and why minimal residual disease studies are necessary in leukemia: a review from WP10 and WP12 of the European LeukaemiaNet", Haematologica, 94(8):1135-1150 (2009).
Benichou, J. et al., "The restricted DH gene reading frame usage in the expressed human antibody repertoire is selected based upon its amino acid content", J Immunol., 190(11): 5567-77, 29 pages (2013).
Benichou, J. et al., "Rep-Seq: uncovering the immunological repertoire through next-generation sequencing", Immunology, 135(3): 183-191 (2011).
Berger, et al. "The clonotypic T cell receptor is a source of tumor-associated antigens in cutaneous T cell lymphoma", Annals of the New York Academy of Sciences, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Bernard et al. "Color multiplexing hybridization probes using the apolipoprotein E locus as a model system for genotyping", Anal Biochem., 273(2):221-228 (1999).
Bernardin, F. et al., "Estimate of the total Number of CD8+ clonal expansions in healthy adults using a new DNA heteroduplex-tracking assay for CDR3 repertoire analysis", Journal of Immunological Methods, 274(1-2):159-175 (2003).
Bertness, et al. "T-Cell Receptor Gene Rearrangements as Clinical Markers of Human T-Cell Lymphomas", The New England Journal of Medicine, 313:534-538 (1985).
Bessette, et al., "Rapid isolation of high-affinity protein binding peptides using bacterial display." Protein Engineering, Design and Selection (Oct. 2004); 17(10): 731-739.
Bhatia, et al., "Rolling Adhesion Kinematics of Yeast Engineered to Express Selectins." Biotechnology Progress (2003); 19(3): 1033-1037.

(56) References Cited

OTHER PUBLICATIONS

Bidwell, "Advances in DNA-based HLA-typing methods." Immunol Today (Jul. 1994); 15 (7): 303-307.
Biggerstaff, et al. "Enumeration of leukocyte infiltration in solid tumors by confocal laser scanning microscopy", BMC Immunol., 7:16, 13 pages (2006).
Boder and Wittrup, "Yeast surface display for screening combinatorial polypeptide libraries." Nat Biotechnol. (Jun. 1997); 15(6): 553-557.
Bolotin, D.A. et al., "Next generation sequencing for TCR repertoire profiling: Platform-specific features and correction algorithms", Eur. J. Immunol., 42:3073-3083 (2012).
Bonarius, H.P.J. et al. "Monitoring the T-Cell Receptor Repertoire at Single-Clone Resolution", PLOS One, 1(e55):1-10 (2006).
Boria, et al. "Primer sets for cloning the human repertoire of T cell receptor variable regions", BMC Immunology, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", Molecular Immunology, 45: 2437-2445 (2008).
Boulware and Daugherty, "Protease specificity determination by using cellular libraries of peptide substrates (CLiPS)." PNAS (May 2006); 103 (20): 7583-7588.
Boyce, et al. "Human regulatory T-cell isolation and measurement of function", BD Biosciences, pp. 1-20 (2010).
Boyd, S.D. et al., "Individual Variation in the Germline Ig Gene Repertoire Inferred from Variable Region Gene Rearrangements", The Journal of Immunology, 184(12): 6986-6992 (2010). Epub 2010.
Boyd, S.D. et al., "Measurement and Clinical Monitoring of Human Lymphocyte Clonality by Massively Parallel V-D-J Pyrosequencing," Science Translational Medicine, 1:12ra23, 40 pages, including Supplementary Materials (2009).
Bradbury, et al., "Use of Living Columns to Select Specific Phage Antibodies." BioTechnology (1993); 11: 1565-1568.
Bradfield, et al. "Graft-versus-leukemia effect in acute lymphoblastic leukemia: the importance of tumor burden and early detection", Leukemia, 18(6): 1156-1158 (2004).
Brehm-Stecher and Johnson. "Single-cell microbiology: tools, technologies, and applications", Microbiology and Molecular Biology Reviews, 68(3):538-559 (2004).
Brenan, C. et al., "High throughput, nanoliter quantitative PCR," Drug Discovery Today: Technologies, 2(3):247-253 (2005).
Brennan et al. "Predictable αβ T-cell receptor selection toward an HLA-B*3501—restricted human cytomegalovirus epitope", J. Virol., 81(13): 7269-7273 (2007).
Brisco, et al. "Determining the repertoire of IGH gene rearrangements to develop molecular markers for minimal residual disease in B-lineage acute lymphoblastic leukemia", J Mol Diagn., 11(3):194-200 (2009).
Brisco, et al. "Outcome prediction in childhood acute lymphoblastic leukaemia by molecular quantification of residual disease at the end of induction", Lancet, 343:196-200 (1994).
Brochet et al. "IMGT/V-QUEST: the highly customized and integrated system for IG and TR standardized V-J and V-D-J sequence analysis", Nucleic Acids Research, vol. 36, Web Server issue W503-W508 (2008).
Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", Journal of Clinical Oncology, ASCO Annual Meeting Abstracts Part 1, Suppl; abstr 2509: vol. 29, No. 15, 1 page (2011).

Brüggemann, et al. "Clinical significance of minimal residual disease quantification in adult patients with standard-risk acute lymphoblastic leukemia", Blood, 107(3):1116-1123 (2006). Epub Sep. 29, 2005.
Brüggemann, et al. "Rearranged T-cell receptor beta genes represent powerful targets for quantification of minimal residual disease in childhood and adult T-cell acute lymphoblastic leukemia", Leukemia, 18(4): 709-719 (2004).
Brüggemann, et al. "Standardized MRD quantification in European All trials: proceedings of the Second International Symposium on MRD assessment in Kiel, Germany, Sep. 18-20, 2008", Leukemia, 24(3):521-535 (2010). doi: 10.1038/leu.2009.268. Epub Dec. 24, 2009.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Bupp and Roth, "Altering retroviral tropism using a random-display envelope library." Mol Ther. (Mar. 2002); 5(3): 329-335.
Butkus, B. "Hutch Team Uses ddPCR to Quantify T-Cell Response in Tumors; Adaptive Biotech Eyes Market", PCR Insider, Dec. 12, 2013, 3 pages http://www.genomeweb.com/print/1323296.
Bystrykh. "Generalized DNA Barcode Design Based on Hamming Codes", PLoS One, 7(5): e36852, 1-8 (2012).
Campana, et al. "Role of minimal residual disease monitoring in adult and pediatric acute lymphoblastic leukemia", Hematol Oncol Clin North Am., 23(5): 1083-1098 (2009). doi: 10.1016/j.hoc.2009.07.010.
Campana. "Minimal residual disease in acute lymphoblastic leukemia", Semin Hematol., 46(1):100-106 (2009).
Campbell et al. "Subclonal phylogenetic structures in cancer revealed by ultra-deep sequencing," PNAS, 105(35):13081-13086 (2008).
Caporaso, J.G. et al. "Global patterns of 16S rRNA diversity at a depth of millions of sequences per sample", PNAS, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", Blood, 113(15): 3553-3557 (2009). doi: 10.1182/blood-2008-08-174839. Epub Feb. 6, 2009.
Carlson et al. "Profiling the repertoire of TCRB usage in induced and natural Treg cells", The Journal of Immunology, 186: 62.5, Abstract (2011).
Carlson, C.S. et al. "Using synthetic templates to design an unbiased multiplex PCR assay", Nature Communications, 4:2680, pgs. 1-9 (2013).
Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.
Casali, et al. "Human monoclonals from antigen-specific selection of B lymphocytes and transformation by EBV", Science, 234(4775): 476-479, Abstract Only (1986).
Casbon et al. "A method for counting PCR template molecules with application to next-generation sequencing", Nucleic Acids Research, 39(12): e81, 8 pages (2011).
Catherwood, M.A. et al., "Improved clonality assessment in germinal centre/post germinal centre non-Hodgkin's lymphomas with high rates of somatic hypermutation", J. Clin. Pathol., 60:524-528, Abstract (2007).
Cha et al., "Improved Survival with T Cell Clonotype Stability After Anti-CTLA-4 Treatment in Cancer Patients." Sci Transl Med (2014); 6(238): 238ra70.
Chan et al. "Evaluation of Nanofluidics Technology for High-Throughput SNP Genotyping in a Clinical Setting", The Journal of Molecular Diagnostics, 13(3): 305-312 (2011).
Charbit, et al., "Versatility of a vector for expressing foreign polypeptides at the surface of Gram-negative bacteria." Gene (1988); 70(1): 181-189.

(56) References Cited

OTHER PUBLICATIONS

Chen et al. "A novel approach for the analysis of T-cell reconstitution by using a T-cell receptor β-based oligonucleotide microarray in hematopoietic stem cell transplantation", *Exp Hematol.*, 35(5):831-841 (2007).
Chen, et al. "Microfluidic cell sorter with integrated piezoelectric actuator", Biomed Microdevices, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).
Chestnut, et al., "Selective isolation of transiently transfected cells from a mammalian cell population with vectors expressing a membrane anchored single-chain antibody." J Immunol Methods. (Jun. 1996);193(1): 17-27.
Chinese Application No. 201380042163.X, Search Report dated Apr. 12, 2016 (English translation), 2 pages.
Chinese Patent Application No. 2014800254909, Search Report and English translation, dated May 25, 2017, mailed by the Chinese Patent Office dated Jun. 6, 2017, 5 pages.
Chinese Patent Application No. 201510054401.X, Search Report dated Jul. 14, 2016, 2 pages.
Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.
Choi, et al. "Clonal evolution in B-lineage acute lymphoblastic leukemia by contemporaneous $V_H$-$V_H$ gene replacements and $V_H$-$DJ_H$ gene rearrangements", *Blood*, 87(6):2506-2512 (1996).
Choi, et al. "Relapse in children with acute lymphoblastic leukemia involving selection of a preexisting drug-resistant subclone", *Blood*, 110(2):632-639 (2007).
Chothia, C. et al. "Canonical structures for the hypervariable regions of immunoglobulins," *J. Mol. Biol.*, 196:901-917, Abstract only (1987).
Chothia, C. et al. "Conformations of immunoglobulin hypervariable regions," *Nature*, 342:877-883 (1989).
Chou, et al., "Expression of Chimeric Monomer and Dimer Proteins on the Plasma Membrane of Mammalian Cells." Biotechnol Bioeng (Oct. 1999); 65(2): 160-169.
Churchill and Waterman. "The Accuracy of DNA Sequences: Estimating Sequence Quality", *Genomics*, 14:89-98 (1992).
Chute, et al. "Detection of immunoglobulin heavy chain gene rearrangements in classic Hodgkin lymphoma using commercially available BIOMED-2 primers", *Diagn Mol Pathol.*, 17(2): 65-72 (2008).
Citri et al. "Comprehensive qPCR profiling of gene expression in single neuronal cells", *Nature Protocols*, 7(1): 118-127 (2012).
Cleary, et al. "Production of complex nucleic acid libraries using highly parallel in situ oligonucleotide synthesis", *Nat Methods*, 1(3): 241-248 (2004). Epub Nov. 18, 2004.
Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.
Craig et al. "Identification of genetic variants using bar-coded multiplex sequencing", *Nature Methods*, 5(10): 887-893 (2008) and Supplemental Materials.
Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.
Cronn et al. "Multiplex sequencing of plant chloroplast genomes using Solexa sequencing-by-synthesis technology", *Nucleic Acids Research*, 36(19):e122, 1-11 (2008).
Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", *The Journal of Immunology*, 172:1935-1944 (2004).
Curran-Everett, D., "Multiple comparisons: philosophies and illustrations", *Am J Physiol Regulatory Integrative Comp Physiol.*, 279:R1-R8 (2000).
Currier and Robinson. "Spectratype/immunoscope analysis of the expressed TCR repertoire", *Current Protocols in Immunology*, Supplement 38:10.28.1-10.28.24 (2000).
Dane, et al., "Isolation of cell specific peptide ligands using fluorescent bacterial display libraries." J Immunol Methods. (Feb. 2006); 309(1-2): 120-129. Epub Jan. 11, 2006.
Dash, P. et al., "Paired analysis of TCR[alpha] and TCR[beta] chains at the single-cell level in mice", *Journal of Clinical Investigation*, 121(1):288-295 (2011).
Daugherty, et al., "Quantitative analysis of the effect of the mutation frequency on the affinity maturation of single chain Fv antibodies." PNAS (Feb. 2000); 97 (5): 2029-2034.
Davi, et al. "Lymphocytic progenitor cell origin and clonal evolution of human B-lineage acute lymphoblastic leukemia", *Blood*, 88(2):609-621 (1996).
Davis, et al. "Interrogating the repertoire: broadening the scope of peptide-MHC multimer analysis", *Nat Rev Immunol.*, 11(8):551-558 (2011). doi: 10.1038/nri3020.
Davis, et al. "Staining of cell surface human CD4 with 2'-F-pyrimidine-containing RNA aptamers for flow cytometry", *Nucleic Acids Research*, 26(17):3915-3924 (1998).
Day, et al., "Identification of non-amplifying CYP21 genes when using PCR-based diagnosis of 21-hydroxylase deficiency in congenital adrenal hyperplasia (CAH) affected pedigrees." Hum Mol Genet. (Dec. 1996); 5(12): 2039-2048.
de Cárcer, et al., "Strategy for Modular Tagged High-Throughput Amplicon Sequencing." Applied and Environmental Microbiology (Sep. 2011); 77(17): 6310-6312.
Dean, et al. "Rapid amplification of plasmid and phage DNA using Phi 29 DNA polymerase and multiply-primed rolling circle amplification", *Genome Res.*, 11(6): 1095-1099 (2001).
Dedhia, et al. "Evaluation of DNA extraction methods and real time PCR optimization on formalin-fixed paraffin-embedded tissues", *Asian Pac J Cancer Prev.*, 8(1): 55-59 (2007).
DeKosky et al. "High-throughput sequencing of the paired human immunoglobulin heavy and light chain repertoire", *Nature Biotechnology*, 31(2): 166-169 (2013).
Deng et al. "Gene profiling involved in immature CD4+ T lymphocyte responsible for systemic lupus erythematosus", *Molecular Immunology*, 43:1497-1507 (2006).
Deschoolmeester, et al. "Tumor infiltrating lymphocytes: an intriguing player in the survival of colorectal cancer patients", *BMC Immunology*, 11:19, 12 pages (2010).
Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).
Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.
DeWitt, et al., "Dynamics of the Cytotoxic T Cell Response to a Model of Acute Viral Infection." J. Virol. (Apr. 2015); 89 (8): 4517-4526. Epub Feb. 4, 2015.
Dictor et al. "Resolving T-cell receptor clonality in two and genotype in four multiplex polymerase chain reactions", *Haematologica*, 90(11): 1524-1532 (2005).
Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 15, 2003.
Diehl, et al. "BEAMing: single-molecule PCR on microparticles in water-in-oil emulsions", *Nat Methods*, 3(7):551-559, Abstract Only (2006).

(56) References Cited

OTHER PUBLICATIONS

Ding, et al. "Clonal evolution in relapsed acute myeloid leukaemia revealed by whole-genome sequencing", Nature, 481(7382):506-510 (2012).
Diviacco, et al. "A novel procedure for quantitative polymerase chain reaction by coamplification of competitive templates", Gene, 122(2):313-320 (1992).
Dobosy, J. et al. "RNase H-dependent PCR (rhPCR): improved specificity and single nucleotide polymorphism detection using blocked cleavable primers", BMC Biotechnology, 11(80):1-18 (2011).
Dohm, et al. "Substantial biases in ultra-short read data sets from high throughput DNA sequencing", Nucleic Acids Research, 36:e105, 10 pages (2008).
Dou, et al. "Analysis of T cell receptor $V_\beta$ gene usage during the course of disease in patients with chronic hepatitis B", Journal of Biomedical Science, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", Science, 327(5961):78-81 (2010). Epub Nov. 5, 2009.
Droege, et al. "The Genome Sequencer FLX System—longer reads, more applications, straight forward bioinformatics and more complete data sets", J Biotechnol., 136(1-2):3-10 (2008). doi: 10.1016/j.jbiotec.2008.03.021. Epub Jun. 21, 2008.
Droese, J., et al. "Validation of BIOMED-2 multiplex PCR tubes for detection of TCRB gene rearrangements in T-cell malignancies," Leukemia, 18:1531-1538 (2004).
Du et al. "TCR spectratyping revealed T lymphocytes associated with graft-versus-host disease after allogeneic hematopoietic stem cell transplantation", Leukemia & Lymphoma, 48(8):1618-1627 (2007).
Dueñnas, M., et al. "In vitro immunization of naive human B cells yields high affinity immunoglobulin G antibodies as illustrated by phage display." Immunology (1996); 89.1: 1-7.
Dunn, et al. "Focus on TILs: Prognostic significance of tumor infiltrating lymphocytes in human glioma", Cancer Immun., 7:12, 16 pages (2007).
Dziubianau, M., et al., "TCR repertoire analysis by next generation sequencing allows complex differential diagnosis of T cell-related pathology." Am J Transplant (Nov. 2013); 13(11): 2842-2854. doi: 10.1111/ajt.12431. Epub Sep. 10, 2013.
Eason et al. "Characterization of synthetic DNA bar codes in Saccharomyces cerevisiae gene-deletion strains," PNAS, 101(30): 11046-11051 (2004).
Edd et al. "Controlled encapsulation of single cells into monodisperse picoliter drops", Lab Chip, 8(8):1262-1264 (2008).
Efron and Thisted, "Estimating the number of unseen species: How many words did Shakespeare know?" Biometrika (1976); 63(3): 435-447.
Eichler, et al. "Haplotype and interspersion analysis of the FMR1 CGG repeat identifies two different mutational pathways for the origin of the fragile X syndrome", Hum Mol Genet., 5(3):319-330 (1996).
Eichler, et al. "Length of uninterrupted CGG repeats determines instability in the FMR1 gene", Nat Genet., 8(1):88-94, Abstract Only (1994).
Eid et al. "Real-time DNA sequencing from single polymerase molecules", Science, 323(5910):133-138 (2009). Epub Nov. 20, 2008.
Eis, et al. "An invasive cleavage assay for direct quantitation of specific RNAs", Nat Biotechnol., 19(7):673-676, Abstract Only (2001).
Eisenstein. "Personalized, sequencing-based immune profiling spurs startups", Nat Biotechnol., 31(3):184-186 (2013). doi: 10.1038/nbt0313-184b.
Elkord et al. "T regulatory cells in cancer: recent advances and therapeutic potential", Expert Opinion on Biological Therapy, 10(11): 1573-1586 (2010).

Emerson et al. "Defining the Alloreactive T Cell Repertoire Using High-Throughput Sequencing of Mixed Lymphocyte Reaction Culture", PLoS One, 9(11): e111943 (2014).
Emerson, et al. "CD4+ and CD8+ T cell β antigen receptors have different and predictable V and J gene usage and CDR3 lengths", Presented at the Annual Meeting of The American Association of Immunologists 2012 in Boston, MA May 2012. Poster.
Emerson, et al. "Correlation of TCR diversity with immune reconstitution after cord blood transplant", Presented at the American Society of Clinical Oncology's annual meeting. May 2012. Poster. 1 page.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al., "De novo detection and HLA-association of public T cell responses to Cytomegalovirus using high-throughput immune repertoire sequencing (VIR1P.1134)." The Journal of Immunology (May 2015); 194 (1 Supplement): 74.1, Abstract.
Emerson, et al., "Immunosequencing identifies signatures of cytomegalovirus exposure history and HLA-mediated effects on the T cell repertoire." Nature Genetics (May 2017); 49 (3): 659-665. Epub Apr. 3, 2017.
Emerson, R.O. et al. "High-throughput sequencing of T-cell receptors reveals a homogeneous repertoire of tumour-infiltrating lymphocytes in ovarian cancer", Journal of Pathology, 231: 433-440 (2013).
Esendagli et al. "Malignant and non-malignant lung tissue areas are differentially populated by natural killer cells and regulatory T cells in non-small cell lung cancer", Lung Cancer, 59(1): 32-40 (2008).
Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.1300622. Epub Oct. 25, 2013.
European Application No. 09764927.1, European Opposition dated Oct. 15, 2014 (in French only).
European Application No. 09764927.1, Notice of Opposition dated Oct. 14, 2014, Reference# 547-7.
European Application No. 09764927.1, Notice of Opposition dated Oct. 14, 2014, Reference# BR0-0001EP.
European Application No. 10732172.1, Extended European Search Report dated May 29, 2012, 5 pages.
European Application No. 16162568.6, Extended European Search Report dated Jul. 20, 2016, 6 pages.
European Patent Application No. 09764927.1, EPO's Communication of Notices of Opposition, dated Nov. 21, 2014.
European Patent Application No. 09764927.1, Opponent's Response to Submission of the Patentee dated Nov. 23, 2015.
European Patent Application No. 09764927.1, Patentee's Observations/Response dated May 27, 2015.
European Patent Application No. 11777704.5, European Search Report dated Jul. 26, 2013, 6 pages.
European Patent Application No. 13195379.6, Extended European Search Report and Opinion dated Mar. 13, 2014, 6 pages.
European Patent Application No. 13757482.8, Extended European Search Report dated Jun. 6, 2016, 5 pages.
European Patent Application No. 13775514.6, Extended European Search Report dated Dec. 1, 2015, 12 pages.
European Patent Application No. 13804085.2, Extended European Search Report dated Nov. 16, 2015, 10 pages.
European Patent Application No. 13828563.0, Extended European Search Report dated Feb. 12, 2016, 10 pages.
European Patent Application No. 14819680.1, Extended European Search Report dated Feb. 10, 2017, 10 pages.
European Patent Application No. 15758762.7, Extended European Search Report dated Sep. 22, 2017, 12 pages.
European Patent Application No. 15772627.4, Extended European Search Report dated Jul. 19, 2017, 8 pages.
European Patent Application No. 15779750.7, Extended European Search Report dated Aug. 9, 2017, 9 pages.
European Patent Application No. 15854358.7, Extended European Search Report dated Mar. 12, 2018, 12 pages.
European Patent Application No. 16165939.6, Extended European Search Report dated Oct. 7, 2016, 9 pages.

(56) References Cited

OTHER PUBLICATIONS

European Patent Application No. 16183402.3, Extended European Search Report dated Feb. 21, 2017, 8 pages.
European Patent Application No. 16756268.5, Extended European Search Report dated Oct. 22, 2018, 20 pages.
European Patent Application No. 16756268.5, Partial Supplementary European Search Report dated Jun. 19, 2018, 21 pages.
European Patent Application No. 16774304.6, Extended European Search Report dated Oct. 15, 2018, 9 pages.
European Patent Application No. 18153536.0, Extended European Search Report dated Jun. 6, 2018, 7 pages.
European Patent Application No. 18184843.3, Extended European Search Report dated Aug. 13, 2018, 10 pages.
Faham, M. et al. "Deep-sequencing approach for minimal residual disease detection in acute lymphoblastic leukemia", *Blood*, 120(26): 5173-5180 (2012).
Fanning, et al., "Development of the immunoglobulin repertoire." Clin Immunol Immunopathol. (Apr. 1996); 79(1): 1-14.
Feldhaus, et al., "Flow-cytometric isolation of human antibodies from a nonimmune *Saccharomyces cerevisiae* surface display library." Nat Biotechnol. (Feb. 2003); 21(2):163-70. Epub Jan. 21, 2003.
Ferradini et al. "Analysis of T Cell Receptor Variability in Tumor-infiltrating Lymphocytes from a Human Regressive Melanoma", *J. Clin. Invest.*, pp. 1183-1190 (1993).
Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Flaherty et al. "Ultrasensitive detection of rare mutations using next-generation targeted resequencing", *Nucleic Acids Research*, 40(1): e2, 12 pages (2012).
Flohr, T., et al. "Minimal residual disease-directed risk stratification using real-time quantitative PCT analysis of immunoglobulin and T-cell receptor gene rearrangements in the international multicenter trial AIEOP-BFM All 2000 for childhood acute lymphoblastic leukemia", *Leukemia*, 22:771-782 (2008).
Födinger et al., "Multiplex PCR for rapid detection of T-cell receptor-gamma chain gene rearrangements in patients with lymphoproliferative diseases." British Journal of Haematology (1996); 94(1): 136-139.
Frank. "BARCRAWL and BARTAB: software tools for the design and implementation of barcoded primers for highly multiplexed DNA sequencing," *BMC Bioinformatics*, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Freeman, J.D., et al. "Profiling the T-Cell Receptor Beta-Chain Repertoire by Massively Parallel Sequencing", *Genome Research*, 19(10):1817-1824 (2009). Epub Jun. 18, 2009.
Fridman, et al. "Prognostic and predictive impact of intra- and peritumoral immune infiltrates", *Cancer Research*, 71(17): 5601-5605 (2011). Epub Aug. 16, 2011.
Fritz et al. "Alterations in the spinal cord T cell repertoire during relapsing experimental autoimmune encephalomyelitis," *J Immunol*, 164:6662-6668 (2000).
Fu et al. "Counting individual DNA molecules by the stochastic attachment of diverse labels", *PNAS*, 108(22): 9026-9031 and Supporting Materials, 8 pages (2011).
Fuller, et al. "The challenges of sequencing by synthesis", *Nat Biotechnol.*, 7(11): 1013-1023 (2009) (Abstract only). Epub Nov. 6, 2009.
García-Castillo and Núñez, et al. "Detection of clonal immunoglobulin and T-cell receptor gene recombination in hematological malignancies: monitoring minimal residual disease", *Cardiovascular & Haematological Disorders-Drug Targets*, 9:124-135 (2009).
Gauss, et al. "Mechanistic constraints on diversity in human V(D)J recombination", *Mol Cell Biol.*, 16(1):258-269 (1996).

Gawad, et al. "Massive evolution of the immunoglobulin heavy chain locus in children with B precursor acute lymphoblastic leukemia", *Blood*, 120(22):4407-4417 (2012). Epub Aug. 28, 2012.
Georgiou, G., et al., "The promise and challenge of high-throughput sequencing of the antibody repertoire." Nat Biotechnol (2014); 32(2): 158-168.
Gerlinger and Swanton. "How Darwinian models inform therapeutic failure initiated by clonal heterogeneity in cancer medicine", *British Journal of Cancer*, 103(8):1139-1143 (2010). Epub Sep. 28, 2010.
Gerlinger, M. et al. "Ultra deep T cell receptor sequencing reveals the complexity and intratumour heterogeneity of T cell clones in renal cell carcinomas", *Journal of Pathology*, 231:424-432 (2013).
Germano, et al. "Clonality profile in relapsed precursor-B-All children by GeneScan and sequencing analyses. Consequences on minimal residual disease monitoring", *Leukemia*, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-1054 (2013). Epub Feb. 5, 2013.
Gilbert, et al. "The isolation of nucleic acids from fixed, paraffin-embedded tissues-which methods are useful when?", *PLoS One*, 2(6):e537, 12 pages (2007).
Giuggio, et al. "Evolution of the intrahepatic T cell repertoire during chronic hepatitis C virus infection", *Viral Immunology*, 18(1):179-189 (2005).
Gloor et al. "Microbiome profiling by Illumina sequencing of combinatorial sequence-tagged PCR products," *PLoS One*, 5(10): e15406, 15 pages (2010).
Godelaine, et al. "Polyclonal CTL responses observed in melanoma patients vaccinated with dendritic cells pulsed with a MAGE-3.A1 peptide", *J Immunol.*, 171(9):4893-4897 (2003).
Golembowski, et al. "Clonal evolution in a primary cutaneous follicle center B cell lymphoma revealed by single cell analysis in sequential biopsies", *Immunobiology*, 201(5):631-644 (2000).
Gonzalez et al., "Incomplete DJH rearrangements as a novel tumor target for minimal residual disease quantitation in multiple myeloma using real-time PCR", Leukemia, 17:1051-1057 (2003).
Gonzalez, et al. "Incomplete DJH rearrangements of the IgH gene are frequent in multiple myeloma patients: immunobiological characteristics and clinical implications", *Leukemia*, 17:1398-1403 (2003).
Gonzalez, S.F., et al. "Trafficking of B Cell Antigen in Lymph Nodes", *Ann. Rev. Immunol.*, 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", *J Immunol.*, 152(10):5109-5119 (1994).
Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008).
Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", *Nature*, 446(7132): 153-158 (2007).
Grupp, et al. "Chimeric antigen receptor-modified T cells for acute lymphoid leukemia", N. Engl J Med., 368(16):1509-1518 (2013). Epub Mar. 25, 2013.

(56) References Cited

OTHER PUBLICATIONS

Gulliksen, et al. "Real-time nucleic acid sequence-based amplification in nanoliter volumes", Anal Chem., 76(1): 9-14, Abstract Only (2004).
Gunderson et al. "Decoding Randomly Ordered DNA Arrays", Genome Research, 14: 870-877 (2004).
Guo, et al. "Sequence changes at the V-D junction of the $V_H1$ heavy chain of anti-phosphocholine antibodies alter binding to and protection against Streptococcus pneumoniae", Int Immunol., 9(5):665-677 (1997).
Gurrieri, et al. "Chronic lymphocytic leukemia B cells can undergo somatic hypermutation and intraclonal immunoglobulin $V_H DJ_H$ gene diversification", J Exp Med., 196(5):629-639 (2002).
Hadrup, et al. "Parallel detection of antigen-specific T-cell responses by multidimensional encoding of MHC multimers", Nat Methods, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", Leukemia & Lymphoma, 48(7): 1338-1343 (2007).
Hamady, et al. "Error-correcting barcoded primers for pyrosequencing hundreds of samples in multiplex", Nature Methods, 5(3):235-237 (2008). doi: 10.1038/nmeth.1184. Epub Feb. 10, 2010.
Han et al. "Immunorepertoire analysis by multiplex PCR amplification and high throughput sequencing", The Journal of Immunology, 182:42.6, 1 page (2009).
Han, et al., "Linking T-cell receptor sequence to functional phenotype at the single-cell level." Nat Biotechnol. (2014); 32 (7): 684-692. Epub Jun. 22, 2014.
Hanahan, et al. "Hallmarks of cancer: the next generation", Cell, 144(5): 646-674 (2011). doi: 10.1016/j.cell.2011.02.013.
Hanes and Plückthun, "In vitro selection and evolution of functional proteins by using ribosome display." Proc Natl Acad Sci U S A. (May 1997); 94(10): 4937-4942.
Harismendy et al. "Evaluation of next generation sequencing platforms for population targeted sequencing studies", Genome Biology, 10:R32, 13 pages (2009).
Hawkins, et al. "Whole genome amplification—applications and advances", Curr Opin Biotechnol., 13(1): 65-67 (2002).
He, et al. "IgH gene rearrangements as plasma biomarkers in Non-Hodgkin's lymphoma patients", Oncotarget, 2(3): 178-185 (2011).
Hedegaard and Klemm, "Type 1 fimbriae of Escherichia colias carriers of heterologous antigenic sequences." Gene (Dec. 1989); 85(1): 115-124.
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.
Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", Science, 269(5222): 400-403 (1995).
Hesse, et al., "V(D)J recombination: a functional definition of the joining signals." Genes Dev. (Jul. 1989); 3(7): 1053-1061.
Hill, et al. "Using ecological diversity measures with bacterial communities", FEMS Microbiol Ecol., 43(1):1-11 (2003). doi: 10.1111/j.1574-6941.2003.tb01040.x.
Hirohata, et al. "Regulation of human B cell function by sulfasalazine and its metabolites", Int Immunopharmacol., 2(5): 631-640, Abstract Only (2002).
Hodges, E. et al. "Diagnostic role of tests for T cell receptor (TCR) genes",J Clin Pathol., 56(1): 1-11 (2003).
Hofnung, M., "Chapter 4 Expression of Foreign Polypeptides at the Escherichia coliCell Surface." Methods in Cell Biology (1991); 34: 77-105.
Holmes and Al-Rubeai, "Improved cell line development by a high throughput affinity capture surface display technique to select for high secretors." J Immunol Methods. (Nov. 1999); 230(1-2): 141-147.
Holt and Jones. "The new paradigm of flow cell sequencing", Genome Research, 18:839-846 (2008).
Holt. "Q & A: BC cancer agency's Robert Holt on sequencing the immune repertoire in immune reconstitution," Genome Web (www.genomeweb.com) Jun. 30, 2009.
Hoogenboom, et al. "Multi-subunit proteins on the surface of filamentous phage: methodologies for displaying antibody (Fab) heavy and light chains", Nucleic Acids Res., 19(15): 4133-4137 (1991).
Hoogendoorn, et al. "Primary allogeneic T-cell responses against mantle cell lymphoma antigen-presenting cells for adoptive immunotherapy after stem cell transplantation", Clin Cancer Res., 11(14): 5310-5318 (2005).
Hoos, et al. "Improved endpoints for cancer immunotherapy trials", J Natl Cancer Inst., 102(18): 1388-1397 (2010). Epub Sep. 8, 2010.
Hosono, et al. "Unbiased whole-genome amplification directly from clinical samples", Genome Res., 13(5): 954-964 (2003). Epub Apr. 14, 2003.
Hoven, et al. "Detection and isolation of antigen-specific B cells by the fluorescence activated cell sorter (FACS)", J Immunol Methods, 117(2): 275-284, Abstract Only, 2 pages (1989).
Howe, et al. "T cell receptor clonotype analysis of T cell responses: Diagnostic application of a clonotypic database", Blood (2003); 102 (11): Abstract 3918, p. 54b, 1 page.
Howie, et al., "High throughput pairing of T cell receptor α and β sequences." Science Translational Medicine (2015); 7(301): 301ra131, and supplementary materials, 19 pages.
Huh, et al. "Microfluidics for flow cytometric analysis of cells and particles", Physiol Meas., 26(3): R73-98, Abstract Only (2005). Epub Feb. 1, 2005.
Huijsmans, et al. "Comparative analysis of four methods to extract DNA from paraffin-embedded tissues: effect on downstream molecular applications", BMC Res Notes, 3:239, 9 pages (2010).
Huse, et al. "Generation of a large combinatorial library of the immunoglobulin repertoire in phage lambda", Science, 246(4935): 1275-1281, Abstract Only (1989).
Hwang, H.Y. et al. "Identification of a Commonly used CDR3 Region of Infiltrating T Cells Expressing Vβ13 and Vβ15 Derived from Psoriasis Patients", The Journal of Investigative Dermatology, 120(3):359-364 (2003).
Iancu, et al. "Profile of a serial killer: cellular and molecular approaches to study individual cytotoxic T-cells following therapeutic vaccination", J Biomed Biotechnol., 2011: 452606 (2011). doi: 10.1155/2011/452606. Epub Nov. 14, 2010.
Ilakovac, V., "Statistical hypothesis testing and some pitfalls." Biochemia Medica (2009); 19(1): 10-16, 4 pages. [online]. [Retrieved on Apr. 12, 2013]. Retrieved from the Internet: <URL:http://www.biochemia-medica.com/contentlstatistical-hypothesis-testing-and-some-pitfalls>PDF.
Illumina Systems & Software, Technology Spotlight, DNA Sequencing with Solexa® Technology, Illumina, Inc., Pub. No. 770-2007-002, 4 pages (2007).
Illumina. "Technical Note: Systems and Software. Calling sequencing SNPs", 3 pages (2010).
Illumina. Data Sheet, "TruSeq™ exome enrichment kit", 5 pages (2011).
Illumina. Data Sheet: Sequencing. Genomic Sequencing. Pub. No. 770.2008-016 Reference states: "Current as of Jan. 30, 2009", 6 pages, Copyright 2010.
Illumina. TruSeq Sample Preparation Kit and Data Sheet. Illumina, Inc., San Diego, CA, 4 pages (2011).
Ishii et al. "Isolation and expression profiling of genes upregulated in the peripheral blood cells of systemic lupus erythematosus patients," DNA Research, 12:429-439 (2005).
Jabara et al. "Accurate sampling and deep sequencing of the HIV-1 protease gene using a Primer ID", PNAS, 108(50): 20166-20171 (2011).

(56) References Cited

OTHER PUBLICATIONS

Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).
Jacobi et al. "Correlation between circulating CD27$^{high}$ plasma cells and disease activity in patients with systemic lupus erythematosus" *Arthritis & Rheumatism*, 48(5):1332-1342 (2003).
Jaffe, et al. "Classification of lymphoid neoplasms: the microscope as a tool for disease discovery", *Blood*, 112(12): 4384-4399 (2008). doi: 10.1182/blood-2008-07-077982.
Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.
Jena, et al. "Amplification of genes, single transcripts and cDNA libraries from one cell and direct sequence analysis of amplified products derived from one molecule", *J. Immunol. Methods*, 190:199-213 (1996).
Jochems and Schlom. "Tumor-infiltrating immune cells and prognosis: the potential link between conventional cancer therapy and immunity", *Exp Biol Med*(Maywood), 236(5): 567-579 (2011). Epub Apr. 12, 2011.
Jung, et al. "Unraveling V(D)J recombination; insights into gene regulation", *Cell*, 116(2): 299-311 (2004).
Jurkat, Clone 6-1 (ATCC TIB-152) Webpage retrievable from the ATCC under http://www.lgcstandards-atcc.org/Products/ All MB-152.aspx#characteristics. Accessed Oct. 14, 2014.
Kanagawa, T., "Bias and artifacts in multitemplate polymerase chain reactions (PCR)." J Biosci Bioeng. (2003); 96(4): 317-323.
Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt.2012.06.005. Epub Jun. 12, 2012.
Kato et al. "Analysis of accumulated T cell clonotypes in patients with systemic lupus erythematosus," *Arthritis & Rheumatism*, 43(12):2712-2721 (2000).
Katz, S.C. et al. "T Cell Infiltrate Predicts Long-Term Survival Following Resection of Colorectal Cancer Liver Metastases," Ann. Surg. Oncol., 16:2524-2530 (2009).
Kedzierska, et al. "Tracking phenotypically and functionally distinct T cell subsets via T cell repertoire diversity", *Mol Immunol.*, 45(3): 607-618 (2008). Epub Aug. 24, 2007.
Kiianitsa, et al., "Development of Tools for T-Cell Repertoire Analysis (TCRB Spectratyping) for the Canine Model of Hematopoietic Cell Transplantation", *Blood*, ASH—Annual Meeting Abstracts, 110 (11): Abstract 4873, 2 pages (2007).
Kim, et al. "An efficient and reliable DNA extraction method for preimplantation genetic diagnosis: a comparison of allele drop out and amplification rates using different single cell lysis methods", *Fertility and Sterility*, 92: 814-818 (2009).
Kim, et al. "Polony multiplex analysis of gene expression (PMAGE) in mouse hypertrophic cardiomyopathy", *Science*, 316(5830):1481-1484 (2007).
Kinde et al. "Detection and quantification of rare mutations with massively parallel sequencing," *PNAS*, 108(23): 9530-9535 and Supporting Information, 16 pages (2011).
Kircher, et al. "Improved base calling for the Illumina Genome Analyzer using machine learning strategies", *Genome Biol.*, 10(8): R83, 9 pages (2009). doi: 10.1186/gb-2009-10-8-r83. Epub Aug. 14, 2009.
Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.
Kita, et al. "T cell receptor clonotypes in skin lesions from patients with systemic lupus erythematosus", *Journal of Investigative Dermatology*, 110(1): 41-46 (1988).
Kivioja et al. "Counting absolute numbers of molecules using unique molecular identifiers," *Nature Methods*, 9(1): 72-76 (2012).

Klarenbeek, P.L. et al. "Deep sequencing of antiviral T-cell responses to HCMV and EBV in humans reveals a stable repertoire that is maintained for many years." PLoS Pathogens (2012); 8.9: e1002889.
Klarenbeek, P.L. et al. "Human T-cell memory consists mainly of unexpanded clones", *Immunology Letters*, 133: 42-48 (2010).
Klauser, et al., "Extracellular transport of cholera toxin B subunit using Neisseria IgA protease beta-domain: conformation-dependent outer membrane translocation." The EMBO Journal (Jun. 1990); 9(6): 1991-1999.
Klenerman, et al. "Tracking T cells with tetramers: new tales from new tools", *Nat Rev Immunol.*, 2(4):263-272 (2002).
Klinger et al. "Combining next-generation sequencing and immune assays: a novel method for identification of antigen-specific T cells", PLoS One, 8(9): e74231, 1-9 (2013).
Kneba, et al. "Characterization of clone-specific rearrangement T-cell receptor gamma-chain genes in lymphomas and leukemias by the polymerase chain reaction and DNA sequencing", *Blood*, 84(2):574-581 (1994).
Kneba, M., et al. "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).
Kobari, et al. "T cells accumulating in the inflamed joints of a spontaneous murine model of rheumatoid arthritis become restricted to common clonotypes during disease progression", *Int Immunol.*, 16(1):131-138 (2004).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," *Ann Surg.*, 244(6): 986-992; discussion 992-993 (2006).
Kohlmann, et al. "Integration of next-generation sequencing into clinical practice: are we there yet?", *Semin Oncol.*, 39(1): 26-36, Abstract Only (2012).
Kojima et al. "PCR amplification from single DNA molecules on magnetic beads in emulsion: application for high-throughput screening of transcription factor targets", *Nucleic Acids Research*, 33: 17, e150, 9 pages (2005).
Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).
Krueger, et al. "Large scale loss of data in low-diversity illumina sequencing libraries can be recovered by deferred cluster calling", *PLoS One*, 6(1): e16607, 7 pages (2011).
Ku, et al. "Exome sequencing: dual role as a discovery and diagnostic tool", *Ann Neurol.*, 71(1):5-14, Abstract Only (2012). doi: 10.1002/ana.22647.
Kumar, et al. "PEG-labeled nucleotides and nanopore detection for single molecule DNA sequencing by synthesis", *Sci Rep.*, 2:684, 8 pages (2012). Epub Sep. 21, 2012.
Kwak, et al. "Induction of immune responses in patients with B-cell lymphoma against the surface-immunoglobulin idiotype expressed by their tumors", *N Engl J Med.*, 327(17):1209-1215 (1992).
Kyu et al. "Frequencies of human influenza-specific antibody secreting cells or plasmablasts post vaccination from fresh and frozen peripheral blood mononuclear cells", *Journal of Immunological Methods*, 340: 42-47 (2009).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", *Blood*, vol. 120 , No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", *Experimental Hematology*, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).

(56) References Cited

OTHER PUBLICATIONS

Langerak, et al. "Immunoglobulin/T-cell receptor clonality diagnostics", *Expert Opin. Med. Diagn.*, 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).
Laplaud et al. "Blood T-cell receptor β chain transcriptome in multiple sclerosis. Characterization of the T cells with altered CDR3 length distribution", *Brain*, 127:981-995 (2004).
Laplaud et al. "Serial blood T cell repertoire alterations in multiple sclerosis patients; correlation with clinical and MRI parameters", *Journal of Neuroimmunology*, 177(1-2):151-160 (2006).
Larijani, et al., "The role of components of recombination signal sequences in immunoglobulin gene segment usage: a V81x model." Nucleic Acids Research (Jan. 1999); 27(11): 2304-2309.
Larimore, K., et al. "Shaping of Human Germline IgH Repertoires Revealed by Deep Sequencing", *The Journal of Immunology*, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).
Lee, et al. "Characterization of circulating T cells specific for tumor-associated antigens in melanoma patients", *Nat Med.*, 5(6): 677-685, Abstract Only (1999).
Lee, et al. "Prognostic implications of type and density of tumour-infiltrating lymphocytes in gastric cancer", *Br J Cancer*, 99(10): 1704-1711 (2008). Epub Oct. 21, 2008.
Lee, et al., "A Functional Analysis of the Spacer of V(D)J Recombination Signal Sequences." PLoS Biology (2003); 1(1): el, pp. 056-059.
Lefranc. "IMGT, the international ImMunoGeneTics database", *Nucleic Acids Res.*, 31(1):307-310 (2003).
Leiden, J.M. et al. "The Complete Primary Structure of the T-Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", *PLoS One*, 3(2):e1678, 11 pages (2008).
Leone, et al. "Molecular beacon probes combined with amplification by NASBA enable homogeneous, real-time detection of RNA", *Nucleic Acids Research*, 26(9): 2150-2155 (1998).
Leproust, et al. "Synthesis of high-quality libraries of long (150mer) oligonucleotides by a novel depurination controlled process", *Nucleic Acids Res.*, 38(8): 2522-2540 (2010). Epub Mar. 22, 2010.
Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).
Li, et al. "An improved one-tube RT-PCR protocol for analyzing single-cell gene expression in individual mammalian cells", *Anal. Bioanal. Chem.*, 397: 1853-1859 (2010).
Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).
Li, et al. "Detailed clonality analysis of relapsing precursor B acute lymphoblastic leukemia: implications for minimal residual disease detection", *Leukemia Research*, 25:1033-1045 (2001).
Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).
Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).

Li, et al. "βcell-specific CD4+ T cell clonotypes in peripheral blood and the pancreatic islets are distinct", *J Immunol.*, 183(11): 7585-7591 (2009). Epub Nov. 16, 2009.
Liedtke, et al. "A comparison of methods for RNA extraction from lymphocytes for RT-PCR", *PCR Methods and Applications*, 4(3): 185-187 (1994).
Lin, et al. "Multiplex genotype determination at a large number of gene loci", *Proc Natl Acad Sci USA*, 93(6): 2582-2587 (1996).
Linnemann, et al., "High-throughput identification of antigen-specific TCRs by TCR gene capture." Nature Medicine (Nov. 2013); 19 (11): 1534-1541. Epub Oct. 13, 2013.
Linnemann, et al., "TCR repertoires of intratumoral T-cell subsets." Immunological Reviews (2014); 257 (1): 72-82.
Liu, et al. "CD127 expression inversely correlates with FoxP3 and suppressive function of human CD4+ T reg cells", *J Exp Med.*, 203(7): 1701-1711 (2006). Epub Jul. 3, 2006.
Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.
Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).
Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).
Lorimer, I. A., and Pastan, Ira. "Random recombination of antibody single chain Fv sequences after fragmentation with DNaseI in the presence of Mn2+." Nucleic Acids Research (1995); 23.15: 3067-3068.
Lossius, et al., "High-throughput sequencing of TCR repertoires in multiple sclerosis reveals intrathecal enrichment of EBV-reactive CD8+ T cells." European Journal of Immunology (Nov. 2014); 44 (11): 3439-3452. Epub Sep. 16, 2014.
Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.
Lovisa, et al. "IGH and IGK gene rearrangements as PCR targets for pediatric Burkitt's lymphoma and mature B-ALL MRD analysis", *Lab Invest.*, 89(10):1182-1186 (2009).
Lowe, T., et al., "A computer program for selection of oligonucleotide primers for polymerase chain reactions," Nucleic Acids Research (1990); 18(7):1757-1761.
Lowman, et al. "Monovalent phage display: a method for selecting variant proteins from random libraries", Methods: *A Companion to Methods in Enzymology*, 3: 205-216, Abstract Only (1991).
Lu, et al., "Expression of thioredoxin random peptide libraries on the *Escherichia coli* cell surface as functional fusions to flagellin: a system designed for exploring protein-protein interactions." Biotechnology (N Y). (Apr. 1995); 13(4): 366-372.
Lúcio, P. et al. "Flow cytometric analysis of normal B cell differentiation: a frame of reference for the detection of minimal residual disease in precursor-B-ALL", *Leukemia*, 13:419-427 (1999).
Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).
Lyamichev, et al. "Polymorphism identification and quantitative detection of genomic DNA by invasive cleavage of oligonucleotide probes", *Nat Biotechnol.*, 17(3): 292-396 (1999).
Mackay, et al. "Real-time PCR in virology", *Nucleic Acids Res.*, 30(6): 1292-1305 (2002).
Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3.

(56) References Cited

OTHER PUBLICATIONS

Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.
Mar et al. "Inferring steady state single-cell gene expression distributions from analysis of mesoscopic samples", *Genome Biology*, 7(12): R119, 12 pages (2006).
Mardis. "Next-generation DNA sequencing methods", *Annu. Rev. Genomics Hum. Genet.*, 9:387-402 (2008). doi:.
Margulies, et al. "Genome sequencing in microfabricated high-density picolitre reactors", *Nature*, 437(7057):376-380 (2005). Epub Jul. 31, 2005.
Mariani, S. et al., "Comprehensive assessment of the TCRBV repertoire in small T-cell samples by means of an improved and convenient multiplex PCR method," *Experimental Hematology*, 37(6):728-738 (2009).
Markoulatos, P. et al., "Multiplex Polymerase Chain Reaction: A Practical Approach", Journal of Clinical Laboratory Analysis, 16:47-51 (2002).
Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).
Mary et al. "Analysis of gene expression at the single-cell level using microdroplet-based microfluidic technology", *Biomicrofluidics*, 5: 024109-1-024109-10 (2011).
Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).
Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).
Mato et al. "Correlation of clonal T cell expansion with disease activity in systemic lupus erythematosus", *Int Immunol.*, 9(4):547-554 (1997).
Matolcsy, et al. "Clonal evolution of B cells in transformation from low-to high-grade lymphoma", *Eur. J. Immunol.*, 29(4):1253-1264 (1999).
Matsumoto et al. "CDR3 spectratyping analysis of the TCR repertoire in Myasthenia Gravis", *The Journal of Immunology*, 176:5100-5107 (2006).
Matsumoto et al. "Complementarity-determining region 3 spectratyping analysis of the TCR repertoire in multiple sclerosis", *The Journal of Immunology*, 170:4846-4853 (2003).
Mazor et al. "Antibody internalization studied using a novel IgG binding toxin fusion", *Journal of Immunological Methods*, 321: 41-59 (2007).
Mazumder, et al., "Detection of multiple myeloma cells in peripheral blood using high-throughput sequencing assay" *Blood*, vol. 120, No. 21, Abstract 321 (Conference Abstract), Entire Abstract (2012).
McCAFFERTY, et al., "Phage antibodies: filamentous phage displaying antibody variable domains." Nature (Dec. 1990); 348(6301): 552-554.
McCloskey et al. "Encoding PCR products with batch-stamps and barcodes," *Biochem. Genet.*, 45: 761-767 (2007).
McLean et al. "Recognition of human cytomegalovirus by human primary immunoglobulins identifies an innate foundation to an adaptive immune response", *J. Immunol.*, 174(8): 4768-4778 (2005).
Mei et al. "Blood-borne human plasma cells in steady state are derived from mucosal immune responses", *Blood*, 113(11): 2461-2469 (2009).
Meier et al. "Simultaneous evaluation of T-cell and B-cell clonality, t(11;14) and t(14;18), in a single reaction by a four-color multiplex polymerase chain reaction assay and automated High-Resolution fragment analysis", American Journal of Pathology, 159(6): 2031-2043 (2001).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier, et al. "The influence of different stimulation conditions on the assessment of antigen-induced CD154 expression on CD4+ T cells", *Cytometry A.*, (11):1035-1042 (2008). doi: 10.1002/cyto.a.20640.
Meijer et al. "Isolation of Human Antibody Repertoires with Preservation of the Natural Heavy and Light Chain Pairing", *J. Mol. Biol.*, 358: 764-772 (2006).
Meleshko, et al. "Rearrangements of IgH, TCRD and TCRG genes as clonality marker of childhood acute lymphoblastic leukemia", *Experimental Oncology*, 27(4):319-324 (2005).
Menezes et al. "A public T cell clonotype within a heterogeneous autoreactive repertoire is dominant in driving EAE", *J Clin Invest*, 117(8):2176-2185 (2007).
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", *Nature Reviews, Genetics*, 11:31-46 (2010).
Meyer et al. "Targeted high-throughput sequencing of tagged nucleic acid samples", *Nucleic Acids Research*, 35(15): e97, 5 pages (2007).
Miceli and Parnes. "The roles of CD4 and CD8 in T cell activation", *Seminars in Immunology*, 3(3): 133-141 (1991). Abstract only.
Michálek, et al. "Detection and long-term in vivo monitoring of individual tumor-specific T cell clones in patients with metastatic melanoma", *J Immunol.*, 178(11):6789-6795 (2007).
Michálek, et al. "Identification and monitoring of graft-versus-host specific T-cell clone in stem cell transplantation", *The Lancet*, 361(9364): 1183-1185 (2003).
Miller, et al., "Assembly algorithms for next-generation sequencing data", Genomics, 95(6): 315-327 (2010).
Miltenyi, et al. "High gradient magnetic cell separation with MACS", *Cytometry*, 11(2): 231-238 (1990).
Miner et al. "Molecular barcodes detect redundancy and contamination in hairpin-bisulfite PCR", *Nucleic Acids Research*, 32(17): e135, 4 pages (2004).
Miqueu, P. et al. "Statistical analysis of CDR3 length distributions for the assessment of T and B cell repertoire biases", *Molecular Immunology*, 44:1057-1064 (2007).
Miqueu, P., et al., "Analysis of the peripheral T-cell repertoire in kidney transplant patients." Eur J Immunol. (Nov. 2010 ); 40(11): 3280-3290. Epub Oct. 27, 2010.
Mitra, et al. "Fluorescent in situ sequencing on polymerase colonies", *Anal Biochem.*, 320(1): 55-65, Abstract Only (2003).
Miyashita, et al. "N-Methyl substituted 2',4'—BNANC: a highly nuclease-resistant nucleic acid analogue with high-affinity RNA selective hybridization", *Chem Commun* (Camb), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).
Molloy, et al. "Soluble T cell receptors: novel immunotherapies", *Curr Opin Pharmacol.*, 5(4): 438-443 (2005) (Abstract Only).
Monod, M.Y. et al. "IMGT/JunctionAnalysis: the first tool for the analysis of the immunoglobulin and T cell receptor complex V-J and V-D-J JUNCTIONs", *Bioinformatics*, 20(Suppl 1):i379-385 (2004).
Moody, et al. "Antigen-specific B cell detection reagents: use and quality control", *Cytometry A.*, 73(11): 1086-1092 (2008). doi: 10.1002/cyto.a.20599.
Morgan, et al. "Cancer regression in patients after transfer of genetically engineered lymphocytes", *Science*, 314(5796): 126-129 (2006). Epub Aug. 31, 2006.
Morozova et al. "Applications of New Sequencing Technologies for Transcriptome Analysis", *Annu. Rev. Genomics Hum. Genet.*, 10: 135-151 (2009).
Morrissy et al. "Next-generation tag sequencing for cancer gene expression profiling", *Genome Research*, 19: 1825-1835 (2009).

(56) References Cited

OTHER PUBLICATIONS

Moss, et al. "The human T cell receptor in health and disease", *Annu. Rev. Immunol.*, 10:71-96 (1992).

Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.

Müller, et al., "Random peptide libraries displayed on adeno-associated virus to select for targeted gene therapy vectors." Nat Biotechnol. (Sep. 2003); 21(9): 1040-1046. Epub Aug. 3, 2003.

Muraro et al. "Molecular tracking of antigen-specific T cell clones in neurological immune-mediated disorders", *Brain*, 126(Pt 1):20-31 (2003).

Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.

Nadel, et al., "Decreased Frequency of Rearrangement due to the Synergistic Effect of Nucleotide Changes in the Heptamer and Nonamer of the Recombination Signal Sequence of the Vκ Gene A2b, Which Is Associated with Increased Susceptibility of Navajos to Haemophilus influenzae Type b Disease." The Journal of Immunology (1998); 161(11): 6068-6073.

Nadel, et al., "Sequence of the Spacer in the Recombination Signal Sequence Affects V(D)J Rearrangement Frequency and Correlates with Nonrandom Vκ Usage in Vivo." Jornal of Experimental Medicine (1998); 187 (9): 1495-1503.

Naito, et al. "CD8+ T cells infiltrated within cancer cell nests as a prognostic factor in human colorectal cancer", *Cancer Research*, 58(16): 3491-3494 (1998).

Nakajima, et al., "Expression of random peptide fused to invasin on bacterial cell surface for selection of cell-targeting peptides." Gene (Dec. 2000); 260 (1-2): 121-131.

Nardi, et al. "Quantitative monitoring by polymerase colony assay of known mutations resistant to ABL kinase inhibitors", *Oncogene*, 27(6):775-782 (2008). Epub Aug. 6, 2007, 1-8.

Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Nelson. "CD20+ B cells: the other tumor-infiltrating lymphocytes", *The Journal of Immunology*, 185(9): 4977-4982 (2010). doi: 10.4049/jimmunol.1001323.

Newman, et al. "Identification of an antigen-specific B cell population", *J Immunol Methods*, 272(1-2): 177-187, Abstract Only (2003).

Newton, et al., "Immune response to cholera toxin epitope inserted in *Salmonella flagellin*." Science (Apr. 1989); 244(4900): 70-72.

Nguyen et al. "Identification of errors introduced during high throughput sequencing of the T cell receptor repertoire" *BMC Genomics*, 12: 106, 13 pages (2011).

Nielsen, et al. "Peptide nucleic acid (PNA). A DNA mimic with a pseudopeptide backbone", *Chem. Soc. Rev.*, 26:73-78, Abstract Only (1997).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Oble, et al. "Focus on TILs: prognostic significance of tumor infiltrating lymphocytes in human melanoma", *Cancer Immunity*, 9: 3, 20 pages (2009).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogino and Wilson., "Quantification of PCR Bias Caused by a Single Nucleotide Polymorphism in SMN Gene Dosage Analysis." *The Journal of Molecular Diagnostics* (Nov. 2002); 4(4): 185-190.

Ogle, et al. "Direct measurement of lymphocyte receptor diversity", *Nucleic Acids Research*, 31(22):e139, 6 pages (2003).

Ohlin, Mats, et al. "Light chain shuffling of a high affinity antibody results in a drift in epitope recognition." Molecular Immunology (1996); 33.1: 47-56.

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

Packer and Muraro. "Optimized clonotypic analysis of T-cell receptor repertoire in immune reconstitution", *Experimental Hematology*, 35(3):516-521 (2007).

Palmowski, et al. "The use of HLA class I tetramers to design a vaccination strategy for melanoma patients", *Immunol Rev.*, 188: 155-163 (2002) (Abstract Only).

Pan, et al. "A new FACS approach isolates hESC derived endoderm using transcription factors", *PLoS One*, 6(3): e17536, 9 pages (2011). doi: 10.1371/journal.pone.0017536.

Panzara, et al., "Analysis of the T cell repertoire using the PCR and specific oligonucleotide primers." Biotechniques (1992); 12(5): 728-735.

Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).

Parameswaran et al. "A pyrosequencing-tailored nucleotide barcode design unveils opportunities for large-scale sample multiplexing", *Nucleic Acids Research*, 35(19): e130, 9 pages (2007).

Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.

Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.

PCT/US2009/006053, International Preliminary Report on Patentability dated May 10, 2011, 5 pages.

PCT/US2009/006053, International Search Report dated Jun. 15, 2010, 6 pages.

PCT/US2009/006053, Written Opinion dated Jun. 15, 2010, 4 pages.

PCT/US2010/021264, International Preliminary Report on Patentability dated Jul. 19, 2011, 5 pages.

PCT/US2010/021264, International Search Report and Written Opinion dated Apr. 14, 2010, 7 pages.

PCT/US2010/037477, International Preliminary Report on Patentability dated Jan. 4, 2012, 7 pages.

PCT/US2010/037477, International Search Report and Written Opinion dated Sep. 24, 2010, 10 pages.

PCT/US2011/000791, International Preliminary Report on Patentability dated Nov. 6, 2012, 10 pages.

(56) References Cited

OTHER PUBLICATIONS

PCT/US2011/000791, International Search Report and Written Opinion dated Sep. 22, 2011, 13 pages.
PCT/US2011/049012, International Preliminary Report on Patentability dated Feb. 26, 2013, 5 pages.
PCT/US2011/049012, International Search Report and Written Opinion dated Apr. 10, 2012, 9 pages.
PCT/US2013/028942, International Preliminary Report on Patentability dated May 5, 2015, 9 pages.
PCT/US2013/028942, International Search Report and Written Opinion dated May 9, 2013, 10 pages.
PCT/US2013/035857, International Preliminary Report on Patentability dated Oct. 14, 2014, 8 pages.
PCT/US2013/035857, International Search Report and Written Opinion dated Aug. 7, 2013, 10 pages.
PCT/US2013/040221, International Preliminary Report on Patentability dated Apr. 24, 2014, 41 pages.
PCT/US2013/040221, International Search Report and Written Opinion dated Sep. 23, 2013, 15 pages.
PCT/US2013/045276, International Preliminary Report on Patentability dated Dec. 16, 2014, 2014, 7 pages.
PCT/US2013/045276, International Search Report and Written Opinion dated Jan. 29, 2014, 11 pages.
PCT/US2013/045994, International Preliminary Report on Patentability dated Dec. 16, 2014, 10 pages.
PCT/US2013/045994, International Search Report and Written Opinion dated Oct. 25, 2013, 15 pages.
PCT/US2013/051539, International Preliminary Report on Patentability dated Jan. 27, 2015, 7 pages.
PCT/US2013/051539, International Search Report and Written Opinion dated Nov. 27, 2013, 9 pages.
PCT/US2013/054189, International Preliminary Report on Patentability dated Feb. 10, 2015, 7 pages.
PCT/US2013/054189, International Search Report and Written Opinion dated Oct. 21, 2013, 10 pages.
PCT/US2014/030859, International Preliminary Report on Patentability dated Sep. 15, 2015, 8 pages.
PCT/US2014/030859, International Search Report and Written Opinion dated Jul. 18, 2014, 14 pages.
PCT/US2014/044971, International Preliminary Examination Report dated Jan. 6, 2016, 12 pages.
PCT/US2014/044971, International Search Report and Written Opinion dated Oct. 30, 2014, 14 pages.
PCT/US2015/018967, International Preliminary Report on Patentability dated Oct. 18, 2016, 11 pages.
PCT/US2015/018967, International Search Report and Written Opinion dated Jul. 30, 2015, 17 pages.
PCT/US2015/019029, International Preliminary Report on Patentability dated Sep. 6, 2016, 14 pages.
PCT/US2015/019029, International Search Report and Written Opinion dated Sep. 15, 2015, 19 pages.
PCT/US2015/023915, International Preliminary Report on Patentability dated Oct. 4, 2016, 7 pages.
PCT/US2015/023915, International Search Report and Written Opinion dated Aug. 26, 2015, 11 pages.
PCT/US2015/058035, International Preliminary Report on Patentability dated May 2, 2017, 8 pages.
PCT/US2015/058035, International Search Report and Written Opinion dated Jan. 29, 2016, 14 pages.
PCT/US2016/019343, International Preliminary Report on Patentability dated Aug. 29, 2017, 14 pages.
PCT/US2016/019343, International Search Report and Written Opinion dated Jul. 22, 2016, 23 pages.
PCT/US2016/025535, International Preliminary Report on Patentability dated Oct. 3, 2017, 7 pages.
PCT/US2016/025535, International Search Report and Written Opinion dated Jul. 11, 2016, 9 pages.
Peet. "The Measurement of Species Diversity", *Annual Review of Ecology and Systematics*, 5: 285-307, Abstract Only (1974).
Pekin, D. et al. "Quantitative and sensitive detection of rare mutations using droplet-based microfluidics", *Lab Chip*, 11(3): 2156-2166 (2011).
Pels et al. "Clonal evolution as pathogenetic mechanism in relapse of primary CNS lymphoma", *Neurology*, 63(1):167-169 (2004).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Pohl, G. And Shih. "Principle and applications of digital PCR", *Expert Rev. Mol. Diagn.*, 4(1):41-47 (2004).
Polz and Cavanaugh. "Bias in Template-to-Product Ratios in Multitemplate PCR", *Applied and Environmental Microbiology*, 64(10): 3724-3730 (1998).
Pop and Salzberg. "Bioinformatics challenges of new sequencing technology", *NIH, Trends Genet.*, 24(3): 142-149 (2008).
Porter, et al. "Chimeric antigen receptor-modified T cells in chronic lymphoid leukemia", N. Engl J Med., 365(8):725-33 (2011). doi: 10.1056/NEJMoa1103849. Epub Aug. 10, 2011.
Pourmand, et al. "Direct electrical detection of DNA synthesis", *PNAS*, 103(17): 6466-6470 (2006). Epub Apr. 13, 2006.
Prabakaran et al. "454 antibody sequencing—error characterization and correction", *BMC Research Notes*, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-3020 (2013). doi: 10.1111/ajt.12433. Epub Sep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Qu, et al., "Efficient frequency-based de novo short-read clustering for error trimming in next-generation sequencing", *Genome Research*, 19: 1309-1315 (2009).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Ramsden, et al., "Conservation of sequence in recombination signal sequence spacers." Nucleic Acids Res. (May 1994); 22(10): 1785-1796.
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy and Georgiou. "Systems analysis of adaptive immunity by utilization of high-throughput technologies", *Current Opinion in Biotechnology*, 22(4): 584-589 (2011).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reinartz et al. "Massively parallel signature sequencing (MPSS) as a tool for in-depth quantitative gene expression profiling in all organisms", *Brief Funct Genomic Proteomic.*, 1(1): 95-104 (2002).

(56) References Cited

OTHER PUBLICATIONS

Reischl and Kochanowski. "Quantitative PCR. A Survey of the Present Technology", *Molecular Biotechnology*, 3:55-71 (1995).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13/2648. Epub Feb. 28, 2014.
Robins et al. "Detecting and monitoring lymphoma with high-throughput sequencing" *Oncotarget*, 2:287-288 (2011).
Robins, et al. "CD4+ and CD8+ T cell β antigen receptors have different and predictable V and J gene usage and CDR3 lengths", *J. Immunol.*, 188: 115.10, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). Epub Oct. 16, 2013.
Robins, et al. "Overlap of the human CD8+ T cell receptor repertoire." Oct. 2010. Poster. 1 page.
Robins, et al. "Effects of aging on the human adaptive immune system revealed by high-throughput DNA sequencing of T cell receptors", *J Immunol.*, 188: 47.16, Abstract (2012).
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "The Computational Detection of Functional Nucleotide Sequence Motifs in the Coding Regions of Organisms", *Exp Biol Med*, 233(6): 665-673 (2008).
Robins, H. et al. "Ultra-sensitive detection of rare T cell clones", *Journal of Immunological Methods*, 375(1-2): 14-19 (2012). Epub Sep. 10, 2011.
Robins, H. et al. "Comprehensive assessment of T-cell receptor β-chain diversity in αβ T cells", *Blood*, 114(19):4099-4107 (and Supplemental Materials) (2009).
Robins, H. et al. "Overlap and Effective Size of the Human CD8+ T Cell Receptor Repertoire", *Science Transitional Medicine*, 2(47, 47ra64): and Supplemental Materials, 17 pages (2010).
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Roh, et al., "Comparing microarrays and next-generation sequencing technologies for microbial ecology research." Trends Biotechnol. (Jun. 2010); 28(6): 291-299. Epub Apr. 8, 2010.
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Rothberg, et al. "An integrated semiconductor device enabling non-optical genome sequencing", *Nature*, 475(7356): 348-352 (2011). doi: 10.1038/nature10242.
Rougemont, et al. "Probabilistic base calling of Solexa sequencing data", *BMC Bioinformatics*, 9:431, 12 pages (2008).
Ryan et al. "Clonal evolution of lymphoblastoid cell lines", *Laboratory Investigation*, 86(11):1193-1200 (2006). Epub Oct. 2, 2006.
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schlissel, M.S. et al. "Leukemia and lymphoma: a cost of doing business for adaptive immunity", *Genes Dev.*, 20(12): 1539-1544 (2006).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 0027310.
Schmitt et al. "Detection of ultra-rare mutations by next-generation sequencing," *PNAS*, 109(36): 14508-14513 and Supporting Information, 9 pages (2012).
Schøller et al. "Analysis of T cell receptor αβ variability in lymphocytes infiltrating melanoma primary tumours and metastatic lesions", *Cancer Immunol Immunother.* 39(4):239-248 (1994).
Schrappe, M. et al. "Late MRD response determines relapse risk overall and in subsets of childhood T-cell ALL: results of the AIEOP-BFM-ALL 2000 study", *Blood*, 118(8): 2077-2084 (2011).
Schreiber et al. "Cancer immunoediting: integrating immunity's roles in cancer suppression and promotion", *Science*, 331(6024): 1565-1570 (2011). doi: 10.1126/science.1203486.
Schwab et al. "CD8+ T-cell clones dominate brain infiltrates in Rasmussen encephalitis and persist in the periphery", *Brain*, 132:1236-1246 (2009).
Schwartzman, Armin. "Empirical null and false discovery rate inference for exponential families." The Annals of Applied Statistics (2008); 2(4): 1332-1359.
Schweiger et al. "Genome-wide massively parallel sequencing of formaldehyde fixed-paraffin embedded (FFPE) tumor tissues for copy-number-and mutation-analysis", *PLoS One*, 4(5): e5548, 7 pages (2009). doi: 10.1371/journal.pone.0005548. Epub May 14, 2009.
Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).

(56) References Cited

OTHER PUBLICATIONS

Seder and Ahmed, "Similarities and differences in CD4+ and CD8+ effector and memory T cell generation." Nat Immunol. (2003); 4 (9): 835-842.
Sehouli et al. "Epigenetic quantification of tumor-infiltrating T-lymphocytes" *Epigenetics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).
Seo, et al. "Four-color DNA sequencing by synthesis on a chip using photocleavable fluorescent nucleotides", *PNAS*, 102(17): 5926-5931 (2005). Epub Apr. 13, 2005.
Sfanos et al. "Human Prostate-Infiltrating CD8+ T Lymphocytes are Oligoclonal and PD-1+", *The Prostate*, 69(15): 1694-1703 (2009).
Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.
Shen et al. "Comparing platforms for *C. elegans* mutant identification using high-throughput whole-genome sequencing", *PLoS One*, 3(12):e4012, 6 pages (2008).
Shendure and Ji. "Next-generation DNA sequencing", *Nature Biotechnology*, 26(10):1135-1145 (2008).
Shendure, et al. "Advanced sequencing technologies: methods and goals", *Nat Rev Genet.*, 5(5): 335-344 (2004).
Sherwood, A. et al. "Deep Sequencing of the Human TCRγ and TCRβ Repertoires Suggests that TCR β Rearranges After αβ and γδ T Cell Commitment", Science Translational Medicine, *Sci. Transl. Med.*, 3(90): 1-7 (2011).
Sherwood, et al. "New Technologies for Measurements of Tumor Infiltrating Lymphocytes", Presented Nov. 7, 2012 Moscone Center, Exhibit Halls ABC.
Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", *The Journal of Heart and Lung Transplant*, 31: 996-1002 (2012).
Shiroguchi et al. "Digital RNA sequencing minimizes sequence-dependent bias and amplification noise with optimized single-molecule barcodes", *PNAS*, 109(4): 1347-1352 (2012).
Shoemaker et al. "Quantitative phenotypic analysis of yeast deletion mutants using a highly parallel molecular bar-coding strategy," *Nature Genetics*, 14(4): 450-456 (1996).
Shumaker, et al. "Mutation detection by solid phase primer extension", *Hum Mutat.*, 7(4): 346-354, Abstract Only (1996).
Sia, et al. "Microfluidic devices fabricated in poly(dimethylsiloxane) for biological studies", *Electrophoresis*, 24(21): 3563-3576, Abstract Only (2003).
Sims, et al. "Fluorogenic DNA sequencing in PDMS microreactors", *Nat Methods*, 8(7): 575-580 (2011). doi: 10.1038/nmeth.1629.
Sims, et al. "MHC-peptide tetramers for the analysis of antigen-specific T cells", *Expert Rev Vaccines*, 9(7): 765-774 (2010). doi: 10.1586/erv.10.66.
Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).
Singapore Application No. 11201407888R, Written Opinion dated Aug. 14, 2015, 12 pages.
Sint, D., et al. "Advances in multiplex PCR: balancing primer efficiencies and improving detection success", *Methods in Ecology and Evolution*, 3(5): 898-905 (2012).
Skulina et al. "Multiple Sclerosis: Brain-infiltrating CD8+ T cells persist as clonal expansions in the cerebrospinal fluid and blood", *PNAS*, 101(8):2428-2433 (2004).

Smith et al. "Rapid generation of fully human monoclonal antibodies specific to a vaccinating antigen", *Nature Protocols*, 4(3): 372-384 and Corrigenda (2009).
Smith et al. "Rapid whole-genome mutational profiling using next-generation sequencing technologies", *Genome Research*, 18: 1638-1642 (2008).
Smith, et al. "Comparison of biosequences", *Advances in Applied Mathematics*, 2: 482-489 (1981).
Smith, G.P., "Filamentous fusion phage: novel expression vectors that display cloned antigens on the virion surface." Science (Jun. 1985); 228(4705): 1315-1317.
Sobrino, et al. "SNPs in forensic genetics: a review on SNP typing methodologies", *Forensic Sci Int.*, 154(2-3): 181-194, Abstract Only (2005). Epub Jan. 11, 2005.
Sotomayor, et al., "Conversion of tumor-specific CD4+ T-cell tolerance to T-cell priming through in vivo ligation of CD40." Nature Medicine (Jul. 1999); 5(7): 780-787.
Spellman, et al., "Advances in the selection of HLA-compatible donors: refinements in HLA typing and matching over the first 20 years of the National Marrow Donor Program Registry." Biol Blood Marrow Transplant (2008); (9 Suppl):37-44. Epub Jun. 20, 2008.
Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].
Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).
Srinivasan et al. "Effect of fixatives and tissue processing on the content and integrity of nucleic acids", *Am J Pathol.*, 161(6): 1961-1971 (2002).
Srivastava and Robins. "Palindromic nucleotide analysis in human T cell receptor rearrangements", PLoS One, 7(12):e52250 (2012). doi: 10.1371/joumal.pone.0052250. Epub Dec. 21, 2012.
Steenbergen, et al. "Distinct ongoing Ig heavy chain rearrangement processes in childhood B-precursor acute lymphoblastic leukemia", *Blood*, 82(2):581-589 (1993).
Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).
Stemmer, et al. "Single-step assembly of a gene and entire plasmid from large numbers of oligodeoxyribonucleotides", *Gene*, 164(1): 49-53 (1995).
Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).
Stewart and Schwartz. "Immunoglobulin V regions and the B cell", *Blood*, 83(7): 1717-1730 (1994).
Stickler, et al. "An in vitro human cell-based assay to rank the relative immunogenicity of proteins", *Toxicol Sci.*, 77(2): 280-289 (2004). Epub Dec. 22, 2003.
Stiller et al. "Direct multiplex sequencing (DMPS)—a novel method for targeted high-throughput sequencing of ancient and highly degraded DNA", *Genome Research*, 19: 1843-849 (2009).
Straten, Per thor, et al. "T-cell clonotypes in cancer", *Journal of Translational Medicine*, 2(1): 11, 10 pages (2004).
Stratton. "Exploring the genomes of cancer cells: progress and promise", *Science*, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", *J Immunol.*, 161(8): 4428-4436 (1998).
Struyk et al. "T cell receptors in rheumatoid arthritis", *Arthritis & Rheumatism*, 38(5):577-589 (1995).
Sumida et al. "T cell receptor repertoire of infiltrating T cells in lips of Sjögren's syndrome patients", *J Clin Invest.*, 89:681-685 (1992).
Sumida et al. "T cell receptor Vα repertoire of infiltrating T cells in labial salivary glands from patients with Sjögren's syndrome", *J Rheumatol.*, 21:1655-1661 (1994).

(56) References Cited

OTHER PUBLICATIONS

Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szczepanski et al. "Why and how to quantify minimal residual disease in acute lymphoblastic leukemia?", *Leukemia*, 21(4):622-626 (2007). Epub Feb. 15, 2007.
Szczepanski et al., "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).
Szczepanski, T. et al. "Minimal residual disease in leukemia patients", *Lancet Oncology*, 2:409-417 (2001).
Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.
Tackenberg et al. "Clonal expansions of CD4+ β helper T cells in autoimmune myasthenia gravis", *European Journal of Immunology*, 37(3):849-863 (2007).
Tajiri et al. "Cell-microarray analysis of antigen-specific B-cells: single cell analysis of antigen receptor expression and specificity", *Cytometry Part A*, 71A: 961-967 (2007).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tam, James P. "Synthetic peptide vaccine design: synthesis and properties of a high-density multiple antigenic peptide system." Proceedings of the National Academy of Sciences (1988); 85.15: 5409-5413.
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes A γ Protein Expressed on the Majority of CD3+ T Cell Receptor -a/fr Circulating Lymphocytes", *J. Exp. Med.*, 167:694-699 (1988).
Tsai et al. "Discovery of rare mutations in populations: Tilling by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated May 27, 2011 for UK application No. GB1105068.9.
UK Combined Search Report and Office action dated Jun. 29, 2012 for UK application No. GB1209668.1.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Van Der Velden, V.H.J., et al. "Analysis of minimal residual disease by Ig/TCR gene rearrangements: guidelines for interpretation of real-time quantitative PCR data," *Leukemia*, 21:604-611 (2007).
Van Der Velden, V.H.J., et al. "Detection of minimal residual disease in hematologic malignancies by realtime quantitative PCR: principles, approaches, and laboratory aspects," *Leukemia*, 17:1013-1034 (2003).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMH4-CT98-3936", *Leukemia*, 17:2257-2317 (2003).
Van Dongen, J.J.M. et al. "Prognostic value of minimal residual disease in acute lymphoblastic leukaemia in childhood", *The Lancet*, 352:1731-1738 (1998).
Van Heijst, J.W.J., et al., "Quantitative assessment of T-cell repertoire recovery after hematopoietic stem cell transplantation." Nat Med. (2013); 19(3): 372-377.
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV[1]", *The Journal of Immunology*, 181:7853-7862 (2008).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.

(56) References Cited

OTHER PUBLICATIONS

Wang et al. "Immunorepertoire analysis by multiplex PCR amplification and high throughput sequencing", Poster-Program 42.6, the 96th Annual Meeting of the America Association of Immunologists, Seattle, USA, May 8-12, 2009, 1 page.
Wang, et al. "Balanced-PCR amplification allows unbiased identification of genomic copy changes in minute cell and tissue samples", Nucleic Acids Research, 32(9): e76, 10 pages (2004).
Wang, et al. "High throughput sequencing reveals a complex pattern of dynamic interrelationships among human T cell subsets", PNAS, 107(4): 1518-1528 (2010).
Wang, X. et al. "Quantitative Measurement of Pathogen Specific Human Memory T Cell Repertoire Diversity using a CDR3 B-Specific Microarray", BMC Genomics, 8(329): 1-13 (2007).
Warren et al. "Exhaustive T-cell repertoire sequencing of human peripheral blood samples reveals signatures of antigen selection and a directly measured repertoire size of at least 1 million clonotypes", Genome Res., 21(5): 790-797 (2011). Epub Feb. 24, 2011.
Warren et al. "Profiling model T-cell metagenomes with short reads", Bioinformatics, 25(4):458-464 (2009).
Weiss et al. "Clonal Rearrangements of T-Cell Receptor Genes in Mycosis Fungoides and Dermatopathic Lymphadenopathy", The New England Journal of Medicine, 313(9):539-544 (1985).
Welch and Link. "Genomics of AML: clinical applications of next-generation sequencing", American Society of Hematology, 2011: 30-35 (2011). doi: 10.1182/asheducation-2011.1.30.
Wells, et al. "Rapid evolution of peptide and protein binding properties in vitro", Curr Opin Biotechnol., 3(4): 355-362, Abstract Only (1992).
Wells, et al. "Strategies for preimplantation genetic diagnosis of single gene disorders by DNA amplification", Prenatal Diagnosis, 18(13):1389-1401 (1998).
Weng, et al. "Minimal residual disease monitoring with high-throughput sequencing of T cell receptors in cutaneous T cell lymphoma", Sci Transl Med., 5(214):214ra171 (2013).
Westermann and Pabst. "Distribution of lymphocyte subsets and natural killer cells in the human body", Clin Investig., 70(7): 539-544 (1992).
Wetmur and Chen. "An emulsion polymerase chain reaction-based method for molecular haplotyping", Methods in Molecular Biology, 410: 351-361 (1996).
Wetmur and Chen. "Linking emulsion PCR haplotype analysis", chapter 11, Park, D.J. (ed.), PCR Protocols, Methods in Molecular Biology, 687: 165-175 (2011).
Wetmur et al. "Molecular haplotyping by linking emulsion PCR: analysis of paraoxonase 1 haplotypes and phenotypes", Nucleic Acids Research, 33(8):2615-2619 (2005).
Weusten, et al. "Principles of quantitation of viral loads using nucleic acid sequence-based amplification in combination with homogeneous detection using molecular beacons", Nucleic Acids Res., 30(6): e26, 7 pages (2002).
White et al. "High-throughput microfluidic single-cell RT-qPCR", PNAS, 108(34): 13999-14004 (2011).
Whiteford, et al. "Swift: primary data analysis for the Illumina Solexa sequencing platform", Bioinformatics, 25(17): 2194-2199 (2009). doi: 10.1093/bioinformatics/btp383. Epub Jun. 23, 2009.
Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (May 2001); 158(5): 1851-1857.
Wilson, et al., "The use of mRNA display to select high-affinity protein-binding peptides." PNAS (Mar. 2001); 98 (7): 3750-3755.
Wilson-Lingardo et al., "Deconvolution of Combinatorial Libraries for Drug Discovery: Experimental Comparison of Pooling Strategies." J. Med. Chem., (1996); 39 (14): 2720-2726.
Wittrup, "Protein engineering by cell-surface display." Current Opinion in Biotechnology (Aug. 2001); 12(4): 395-399.

Wlodarski et al. "Molecular strategies for detection and quantitation of clonal cytotoxic T-cell responses in aplastic anemia and myelodysplastic syndrome", Blood, 108(8):2632-2641 (2006).
Wlodarski et al. "Pathologic clonal cytotoxic T-cell responses: nonrandom nature of the T-cell-receptor restriction in large granular lymphocyte leukemia", Blood, 106:2769-2779 (2005).
Wolfl, et al. "Activation-induced expression of CD137 permits detection, isolation, and expansion of the full repertoire of CD8+ T cells responding to antigen without requiring knowledge of epitope specificities", Blood, 110(1): 201-210 (2007). Epub Mar. 19, 2007.
Wolfl, et al. "Use of CD137 to study the full repertoire of CD8+ T cells without the need to know epitope specificities", Cytometry A., 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", Nucleic Acids Research, 38(14): e151, 11 pages (2010). doi: 10.1093/nar/gkq510. Epub Jun. 4, 2010.
Woodsworth, Daniel J., et al., "Sequence analysis of T-cell repertoires in health and disease." Genome Medicine (2013); 5: 98, 13 pages.
Wrammert et al. "Rapid cloning of high-affinity human monoclonal antibodies against influenza virus", Nature, 453: 667-672 (2008).
Wu et al. "Focused Evolution of HIV-1 Neutralizing Antibodies Revealed by Structures and Deep Sequencing", Science, 333: 1593-1602 (2011).
Wu, et al. "High-throughput sequencing detects minimal residual disease in acute T lymphoblastic leukemia", Sci Transl Med., 4 (134): 151-17, 134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, H.D. et al. "The Lymphocytic Infiltration in Calcific Aortic Stenosis Predominantly Consists of Clonally Expanded T Cells", The Journal of Immunology, 178(8): 5329-5339 (2007).
Wu, Y-C. et al. "High-throughput immunoglobulin repertoire analysis distinguishes between human IgM memory and switched memory B-cell populations", Blood Journal, 116(7): 1070-1078, 22 pages (2010).
Xie, Yang, et al., "A note on using permutation-based false discovery rate estimates to compare different analysis methods for microarray data." Bioinformatics (2005); 21.23: 4280-4288.
Xiong, et al. "Non-polymerase-cycling-assembly-based chemical gene synthesis: strategies, methods, and progress", Biotechnol Adv., 26(2): 121-134, Abstract Only (2008). Epub Nov. 7, 2007.
Xu, et al. "Simultaneous isolation of DNA and RNA from the same cell population obtained by laser capture microdissection for genome and transcriptome profiling", J Mol Diagn., 10(2):129-134 (2008). doi: 10.2353/jmoldx.2008.070131. Epub Feb. 7, 2008.
Xu, et al., "Viral immunology. Comprehensive serological profiling of human populations using a synthetic human virome." Science (Jun. 2015); 348(6239):aaa0698.
Xu, W. et al. "A Novel Universal Primer-Multiplex-PCR Method with Sequencing Gel Electrophoresis Analysis", PLoS One, 7(1): e22900, 10 pages (2012).
Yagi, et al., "Detection of clonotypic IGH and TCR rearrangements in the neonatal blood spots of infants and children with B-cell precursor acute lymphoblastic leukemia." Blood (2000); 96(1): 264-268.
Yao, et al. "Analysis of the CDR3 length repertoire and the diversity of TCRα chain in human peripheral blood T Lymphocytes", Cell Mol Immunol., 4(3): 215-220 (2007).
Yassai, M.B. et al. "A clonotype nomenclature for T cell receptors", Immunogenetics, 61:493-502 (2009).
Yeh, et al. "Regulating DNA translocation through functionalized soft nanopores", Nanoscale, 4(8): 2685-4693, Abstract Only (2012). doi: 10.1039/c2nr30102d. Epub Mar. 15, 2012.
Yin et al. "Antiretroviral therapy restores diversity in the T-cell receptor Vβ repertoire of CD4 T-cell subpopulations among human immunodeficiency virus type 1-infected children and adolescents", Clinical and Vaccine Immunology, 16(9):1293-1301 (2009).
Yon and Fried. "Precise gene fusion by PCR", Nucleic Acids Research, 17(12):4895, 1 page (1989).

(56) References Cited

OTHER PUBLICATIONS

Yonezawa, et al., "DNA display for in vitro selection of diverse peptide libraries." Nucleic Acids Res. (Oct. 2003); 31(19): e118.

York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.

Yu and Fu. "Tumor-infiltrating T lymphocytes: friends or foes?", *Lab Invest.*, 86(3): 231-245 (2006).

Zagnoni, et al. "Droplet Microfluidics for High-throughput Analysis of Cells and Particles", *Methods in Cell Biology*, Chapter 2, 102: 23-48 (2011).

Zaliova, et al. "Quantification of fusion transcript reveals a subgroup with distinct biological properties and predicts relapse in BCR/ABL-positive ALL: implications for residual disease monitoring", *Leukemia*, 23(5):944-951 (2009).

Zehentner et al. "Minimal Disease Detection and Confirmation in Hematologic Malignancies: Combining Cell Sorting with Clonality Profiling", *Clinical Chemistry*, 52(3): 430-437 (2006).

Zeng et al. "High-performance single cell genetic analysis using microfluidic emulsion generator arrays", *Anal. Chem.*, 82(8):3183-3190 (2010).

Zhong, Q. et al. "Multiplex digital PCR: breaking the one target per color barrier of quantitative PCR", Lab Chip, 11:2167-2174 (2011).

Zhou et al. "High throughput analysis of TCR-β rearrangement and gene expression in single cells", *Laboratory Investigation*, 86: 314-321 (2006).

Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.

Zimmerman and Mannhalter. "Technical aspects of quantitative competitive PCR", *Biotechniques*, 21: 268-279 (1996).

\* cited by examiner

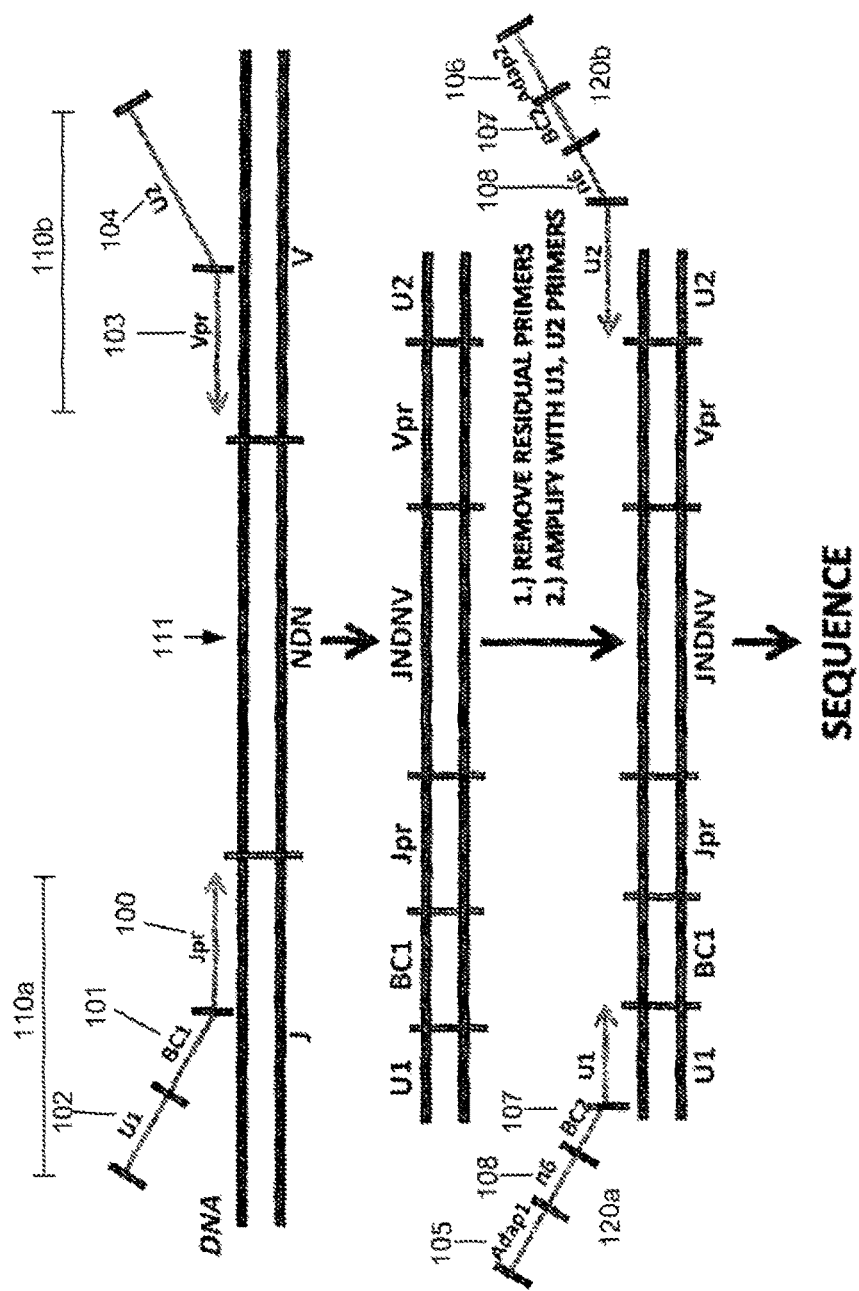

SEQUENCE LISTING

```
<160> NUMBER OF SEQ ID NOS: 132

<210> SEQ ID NO 1
<211> LENGTH: 18
<212> TYPE: DNA
<213> ORGANISM: Artificial Sequence
<220> FEATURE:
<223> OTHER INFORMATION: T7 Promotor adaptor sequence

<400> SEQUENCE: 1
aatacgactc actatagg                                                 18

<210> SEQ ID NO 2
<211> LENGTH: 19
<212> TYPE: DNA
<213> ORGANISM: Artificial Sequence
<220> FEATURE:
<223> OTHER INFORMATION: T7 Terminator adaptor sequence

<400> SEQUENCE: 2
gctagttatt gctcagcgg                                                19

<210> SEQ ID NO 3
<211> LENGTH: 18
<212> TYPE: DNA
<213> ORGANISM: Artificial Sequence
<220> FEATURE:
<223> OTHER INFORMATION: T3 adaptor sequence

<400> SEQUENCE: 3
attaaccctc actaaagg                                                 18

<210> SEQ ID NO 4
<211> LENGTH: 19
<212> TYPE: DNA
<213> ORGANISM: Artificial Sequence
<220> FEATURE:
<223> OTHER INFORMATION: SP6 adaptor sequence

<400> SEQUENCE: 4
```
gatttaggtg acactatag                                          19

<210> SEQ ID NO 5
<211> LENGTH: 18
<212> TYPE: DNA
<213> ORGANISM: Artificial Sequence
<220> FEATURE:
<223> OTHER INFORMATION: M13F(-21) adaptor sequence

<400> SEQUENCE: 5
tgtaaaacga cggccagt                                           18

<210> SEQ ID NO 6
<211> LENGTH: 17
<212> TYPE: DNA
<213> ORGANISM: Artificial Sequence
<220> FEATURE:
<223> OTHER INFORMATION: M13F(-40) adaptor sequence

<400> SEQUENCE: 6
gttttcccag tcacgac                                            17

<210> SEQ ID NO 7
<211> LENGTH: 18
<212> TYPE: DNA
<213> ORGANISM: Artificial Sequence
<220> FEATURE:
<223> OTHER INFORMATION: M13R Reverse adaptor sequence

<400> SEQUENCE: 7
caggaaacag ctatgacc                                           18

<210> SEQ ID NO 8
<211> LENGTH: 21
<212> TYPE: DNA
<213> ORGANISM: Artificial Sequence
<220> FEATURE:
<223> OTHER INFORMATION: AOX1 Forward adaptor sequence

<400> SEQUENCE: 8
gactggttcc aattgacaag c                                       21

<210> SEQ ID NO 9
<211> LENGTH: 21
<212> TYPE: DNA
<213> ORGANISM: Artificial Sequence
<220> FEATURE:
<223> OTHER INFORMATION: AOX1 Reverse adaptor sequence

<400> SEQUENCE: 9
gcaaatggca ttctgacatc c                                       21

<210> SEQ ID NO 10
<211> LENGTH: 23
<212> TYPE: DNA
<213> ORGANISM: Artificial Sequence
<220> FEATURE:
<223> OTHER INFORMATION: pGEX Forward (GST 5, pGEX 5') adaptor sequence

<400> SEQUENCE: 10
gggctggcaa gccacgtttg gtg                                     23

<210> SEQ ID NO 11
<211> LENGTH: 23
<212> TYPE: DNA
<213> ORGANISM: Artificial Sequence

```
<220> FEATURE:
<223> OTHER INFORMATION: pGEX Reverse (GST 3, pGEX 3') adaptor sequence

<400> SEQUENCE: 11
ccgggagctg catgtgtcag agg                                              23

<210> SEQ ID NO 12
<211> LENGTH: 22
<212> TYPE: DNA
<213> ORGANISM: Artificial Sequence
<220> FEATURE:
<223> OTHER INFORMATION: BGH Reverse adaptor sequence

<400> SEQUENCE: 12
aactagaagg cacagtcgag gc                                               22

<210> SEQ ID NO 13
<211> LENGTH: 20
<212> TYPE: DNA
<213> ORGANISM: Artificial Sequence
<220> FEATURE:
<223> OTHER INFORMATION: GFP (C' terminal, CFP, YFP or BFP) adaptor
      sequence

<400> SEQUENCE: 13
cactctcggc atggacgagc                                                  20

<210> SEQ ID NO 14
<211> LENGTH: 20
<212> TYPE: DNA
<213> ORGANISM: Artificial Sequence
<220> FEATURE:
<223> OTHER INFORMATION: GFP Reverse adaptor sequence

<400> SEQUENCE: 14
tggtgcagat gaacttcagg                                                  20

<210> SEQ ID NO 15
<211> LENGTH: 20
<212> TYPE: DNA
<213> ORGANISM: Artificial Sequence
<220> FEATURE:
<223> OTHER INFORMATION: GAG adaptor sequence

<400> SEQUENCE: 15
gttcgacccc gcctcgatcc                                                  20

<210> SEQ ID NO 16
<211> LENGTH: 21
<212> TYPE: DNA
<213> ORGANISM: Artificial Sequence
<220> FEATURE:
<223> OTHER INFORMATION: GAG Reverse adaptor sequence

<400> SEQUENCE: 16
tgacacacat tccacagggt c                                                21

<210> SEQ ID NO 17
<211> LENGTH: 19
<212> TYPE: DNA
<213> ORGANISM: Artificial Sequence
<220> FEATURE:
<223> OTHER INFORMATION: CYC1 Reverse adaptor sequence

<400> SEQUENCE: 17
gcgtgaatgt aagcgtgac                                                   19
```

```
<210> SEQ ID NO 18
<211> LENGTH: 20
<212> TYPE: DNA
<213> ORGANISM: Artificial Sequence
<220> FEATURE:
<223> OTHER INFORMATION: pFastBacF adaptor sequence

<400> SEQUENCE: 18
ggattattca taccgtccca                                              20

<210> SEQ ID NO 19
<211> LENGTH: 20
<212> TYPE: DNA
<213> ORGANISM: Artificial Sequence
<220> FEATURE:
<223> OTHER INFORMATION: pFastBacR adaptor sequence

<400> SEQUENCE: 19
caaatgtggt atggctgatt                                              20

<210> SEQ ID NO 20
<211> LENGTH: 20
<212> TYPE: DNA
<213> ORGANISM: Artificial Sequence
<220> FEATURE:
<223> OTHER INFORMATION: pBAD Forward adaptor sequence

<400> SEQUENCE: 20
atgccatagc atttttatcc                                              20

<210> SEQ ID NO 21
<211> LENGTH: 18
<212> TYPE: DNA
<213> ORGANISM: Artificial Sequence
<220> FEATURE:
<223> OTHER INFORMATION: pBAD Reverse adaptor sequence

<400> SEQUENCE: 21
gatttaatct gtatcagg                                                18

<210> SEQ ID NO 22
<211> LENGTH: 21
<212> TYPE: DNA
<213> ORGANISM: Artificial Sequence
<220> FEATURE:
<223> OTHER INFORMATION: CMV-Forward adaptor sequence

<400> SEQUENCE: 22
cgcaaatggg cggtaggcgt g                                            21

<210> SEQ ID NO 23
<211> LENGTH: 21
<212> TYPE: DNA
<213> ORGANISM: Artificial Sequence
<220> FEATURE:
<223> OTHER INFORMATION: Ck primer

<400> SEQUENCE: 23
gatgaagaca gatggtgcag c                                            21

<210> SEQ ID NO 24
<211> LENGTH: 17
<212> TYPE: DNA
<213> ORGANISM: Artificial Sequence
<220> FEATURE:
```

<223> OTHER INFORMATION: C1-1 primer

<400> SEQUENCE: 24
ggcgggaaca gagtgac                                                        17

<210> SEQ ID NO 25
<211> LENGTH: 19
<212> TYPE: DNA
<213> ORGANISM: Artificial Sequence
<220> FEATURE:
<223> OTHER INFORMATION: C1-2 primer

<400> SEQUENCE: 25
agggtgggaa cagagtgac                                                      19

<210> SEQ ID NO 26
<211> LENGTH: 19
<212> TYPE: DNA
<213> ORGANISM: Artificial Sequence
<220> FEATURE:
<223> OTHER INFORMATION: C1-3 primer

<400> SEQUENCE: 26
gcttgaagct cctcagagg                                                      19

<210> SEQ ID NO 27
<211> LENGTH: 17
<212> TYPE: DNA
<213> ORGANISM: Artificial Sequence
<220> FEATURE:
<223> OTHER INFORMATION: C1-4 primer

<400> SEQUENCE: 27
ggcgggaaca gagtgac                                                        17

<210> SEQ ID NO 28
<211> LENGTH: 17
<212> TYPE: DNA
<213> ORGANISM: Artificial Sequence
<220> FEATURE:
<223> OTHER INFORMATION: IgA primer

<400> SEQUENCE: 28
aggctcagcg ggaagac                                                        17

<210> SEQ ID NO 29
<211> LENGTH: 19
<212> TYPE: DNA
<213> ORGANISM: Artificial Sequence
<220> FEATURE:
<223> OTHER INFORMATION: IgD primer

<400> SEQUENCE: 29
gaacacatcc ggagccttg                                                      19

<210> SEQ ID NO 30
<211> LENGTH: 19
<212> TYPE: DNA
<213> ORGANISM: Artificial Sequence
<220> FEATURE:
<223> OTHER INFORMATION: IgE primer

<400> SEQUENCE: 30
ggtggcattg gagggaatg                                                      19

```
<210> SEQ ID NO 31
<211> LENGTH: 18
<212> TYPE: DNA
<213> ORGANISM: Artificial Sequence
<220> FEATURE:
<223> OTHER INFORMATION: IgG-1 primer

<400> SEQUENCE: 31
aagaccgatg ggcccttg                                                       18

<210> SEQ ID NO 32
<211> LENGTH: 18
<212> TYPE: DNA
<213> ORGANISM: Artificial Sequence
<220> FEATURE:
<223> OTHER INFORMATION: IgG-2 primer

<400> SEQUENCE: 32
ctctcggagg tgctcctg                                                       18

<210> SEQ ID NO 33
<211> LENGTH: 21
<212> TYPE: DNA
<213> ORGANISM: Artificial Sequence
<220> FEATURE:
<223> OTHER INFORMATION: IgM primer

<400> SEQUENCE: 33
aattctcaca ggagacgagg g                                                   21

<210> SEQ ID NO 34
<211> LENGTH: 30
<212> TYPE: DNA
<213> ORGANISM: Artificial Sequence
<220> FEATURE:
<223> OTHER INFORMATION: IgM_RACE primer

<400> SEQUENCE: 34
gatggagtcg ggaaggaagt cctgtgcgag                                          30

<210> SEQ ID NO 35
<211> LENGTH: 25
<212> TYPE: DNA
<213> ORGANISM: Artificial Sequence
<220> FEATURE:
<223> OTHER INFORMATION: IgG_RACE primer

<400> SEQUENCE: 35
gggaagacsg atgggccctt ggtgg                                               25

<210> SEQ ID NO 36
<211> LENGTH: 27
<212> TYPE: DNA
<213> ORGANISM: Artificial Sequence
<220> FEATURE:
<223> OTHER INFORMATION: IgA_RACE primer

<400> SEQUENCE: 36
caggcakgcg aygaccacgt tcccatc                                             27

<210> SEQ ID NO 37
<211> LENGTH: 34
<212> TYPE: DNA
<213> ORGANISM: Artificial Sequence
<220> FEATURE:
<223> OTHER INFORMATION: Ig kappa_RACE primer
```

```
<400> SEQUENCE: 37
catcagatgg cgggaagatg aagacagatg gtgc                          34

<210> SEQ ID NO 38
<211> LENGTH: 28
<212> TYPE: DNA
<213> ORGANISM: Artificial Sequence
<220> FEATURE:
<223> OTHER INFORMATION: Ig lambda_RACE primer

<400> SEQUENCE: 38
cctcagagga gggtgggaac agagtgac                                 28

<210> SEQ ID NO 39
<211> LENGTH: 30
<212> TYPE: DNA
<213> ORGANISM: Artificial Sequence
<220> FEATURE:
<223> OTHER INFORMATION: Smarter UAII primer

<400> SEQUENCE: 39
aagcagtggt atcaacgcag agtacggggg                               30

<210> SEQ ID NO 40
<211> LENGTH: 40
<212> TYPE: DNA
<213> ORGANISM: Artificial Sequence
<220> FEATURE:
<223> OTHER INFORMATION: Islam UAII primer
<220> FEATURE:
<221> NAME/KEY: misc_feature
<222> LOCATION: (32)..(37)
<223> OTHER INFORMATION: n is a, c, g, t
<220> FEATURE:
<221> NAME/KEY: misc_feature
<222> LOCATION: (38)..(40)
<223> OTHER INFORMATION: G is riboguanosine

<400> SEQUENCE: 40
aagcagtggt atcaacgcag agtgcagugc unnnnnnggg                    40

<210> SEQ ID NO 41
<211> LENGTH: 57
<212> TYPE: DNA
<213> ORGANISM: Artificial Sequence
<220> FEATURE:
<223> OTHER INFORMATION: Smarter CDS primer
<220> FEATURE:
<221> NAME/KEY: misc_feature
<222> LOCATION: (1)..(1)
<223> OTHER INFORMATION: A is biotinylated
<220> FEATURE:
<221> NAME/KEY: misc_feature
<222> LOCATION: (56)..(56)
<223> OTHER INFORMATION: n is A, G or C
<220> FEATURE:
<221> NAME/KEY: misc_feature
<222> LOCATION: (57)..(57)
<223> OTHER INFORMATION: n is A, C, G or T

<400> SEQUENCE: 41
aagcagtggt atcaacgcag agtacttttt tttttttttt tttttttttt tttttnn  57

<210> SEQ ID NO 42
<211> LENGTH: 23
<212> TYPE: DNA
<213> ORGANISM: Artificial Sequence
<220> FEATURE:
<223> OTHER INFORMATION: Smarter IS PCR primer
```

```
<220> FEATURE:
<221> NAME/KEY: misc_feature
<222> LOCATION: (1)..(1)
<223> OTHER INFORMATION: A is biotinylated

<400> SEQUENCE: 42
aagcagtggt atcaacgcag agt                                              23

<210> SEQ ID NO 43
<211> LENGTH: 45
<212> TYPE: DNA
<213> ORGANISM: Artificial Sequence
<220> FEATURE:
<223> OTHER INFORMATION: 5'RACE long primer

<400> SEQUENCE: 43
ctaatacgac tcactatagg gcaagcagtg gtatcaacgc agagt                      45

<210> SEQ ID NO 44
<211> LENGTH: 22
<212> TYPE: DNA
<213> ORGANISM: Artificial Sequence
<220> FEATURE:
<223> OTHER INFORMATION: 5'RACE short primer

<400> SEQUENCE: 44
ctaatacgac tcactatagg gc                                               22

<210> SEQ ID NO 45
<211> LENGTH: 23
<212> TYPE: DNA
<213> ORGANISM: Artificial Sequence
<220> FEATURE:
<223> OTHER INFORMATION: pGEXF primer

<400> SEQUENCE: 45
gggctggcaa gccacgtttg gtg                                              23

<210> SEQ ID NO 46
<211> LENGTH: 23
<212> TYPE: DNA
<213> ORGANISM: Artificial Sequence
<220> FEATURE:
<223> OTHER INFORMATION: pGEXR primer

<400> SEQUENCE: 46
ccgggagctg catgtgtcag agg                                              23

<210> SEQ ID NO 47
<211> LENGTH: 35
<212> TYPE: DNA
<213> ORGANISM: Artificial Sequence
<220> FEATURE:
<223> OTHER INFORMATION: pGEXF_IGK_V_01-05_F_D10 primer

<400> SEQUENCE: 47
tctgcatctg taggagacag agtcaccatc acttg                                 35

<210> SEQ ID NO 48
<211> LENGTH: 35
<212> TYPE: DNA
<213> ORGANISM: Artificial Sequence
<220> FEATURE:
<223> OTHER INFORMATION: pGEXF_IGK_V_01-08_F_D10 primer

<400> SEQUENCE: 48
```
tctgcatcta caggagacag agtcaccatc acttg    35

```
<210> SEQ ID NO 49
<211> LENGTH: 35
<212> TYPE: DNA
<213> ORGANISM: Artificial Sequence
<220> FEATURE:
<223> OTHER INFORMATION: pGEXF_IGK_V_01-35_P_D10 primer

<400> SEQUENCE: 49
```
ctgcatctgt aaggagacag tgtcaccatc acttg    35

```
<210> SEQ ID NO 50
<211> LENGTH: 35
<212> TYPE: DNA
<213> ORGANISM: Artificial Sequence
<220> FEATURE:
<223> OTHER INFORMATION: pGEXF_IGK_V_1D-08_F_D10 primer

<400> SEQUENCE: 50
```
tctgcatcta caggagacag agtcaccatc agttg    35

```
<210> SEQ ID NO 51
<211> LENGTH: 35
<212> TYPE: DNA
<213> ORGANISM: Artificial Sequence
<220> FEATURE:
<223> OTHER INFORMATION: pGEXF_IGK_V_1D-22_P_D10 primer

<400> SEQUENCE: 51
```
actgcatctg taggagagag agtcaccatc acttg    35

```
<210> SEQ ID NO 52
<211> LENGTH: 33
<212> TYPE: DNA
<213> ORGANISM: Artificial Sequence
<220> FEATURE:
<223> OTHER INFORMATION: pGEXF_IGK_V_1D-35_P_D10 primer

<400> SEQUENCE: 52
```
gcatctgtaa ggagacagcg tcaccatcac ttg    33

```
<210> SEQ ID NO 53
<211> LENGTH: 36
<212> TYPE: DNA
<213> ORGANISM: Artificial Sequence
<220> FEATURE:
<223> OTHER INFORMATION: pGEXF_IGK_V_1D-42_F_D10 primer

<400> SEQUENCE: 53
```
gtctgcatct gtaggagaca gagtcagtat catttg    36

```
<210> SEQ ID NO 54
<211> LENGTH: 23
<212> TYPE: DNA
<213> ORGANISM: Artificial Sequence
<220> FEATURE:
<223> OTHER INFORMATION: pGEXF_IGK_V_02-04_P_D10 primer

<400> SEQUENCE: 54
```
ggagagccgg cctccatctc ctg    23

```
<210> SEQ ID NO 55
<211> LENGTH: 26
<212> TYPE: DNA
<213> ORGANISM: Artificial Sequence
```

-continued

```
<220> FEATURE:
<223> OTHER INFORMATION: pGEXF_IGK_V_02-10_P_D10 primer

<400> SEQUENCE: 55
cctggagagc cagcctccat ctcctg                                              26

<210> SEQ ID NO 56
<211> LENGTH: 25
<212> TYPE: DNA
<213> ORGANISM: Artificial Sequence
<220> FEATURE:
<223> OTHER INFORMATION: pGEXF_IGK_V_02-18_P_D10 primer

<400> SEQUENCE: 56
ctggagagcc ggcctccatc tcttg                                               25

<210> SEQ ID NO 57
<211> LENGTH: 31
<212> TYPE: DNA
<213> ORGANISM: Artificial Sequence
<220> FEATURE:
<223> OTHER INFORMATION: pGEXF_IGK_V_02-19_P_D10 primer

<400> SEQUENCE: 57
tcttccttgg agagccatcc tccatttcct g                                        31

<210> SEQ ID NO 58
<211> LENGTH: 23
<212> TYPE: DNA
<213> ORGANISM: Artificial Sequence
<220> FEATURE:
<223> OTHER INFORMATION: pGEXF_IGK_V_02-24_F_D10 primer

<400> SEQUENCE: 58
ggacagccgg cctccatctc ctg                                                 23

<210> SEQ ID NO 59
<211> LENGTH: 24
<212> TYPE: DNA
<213> ORGANISM: Artificial Sequence
<220> FEATURE:
<223> OTHER INFORMATION: pGEXF_IGK_V_02-28_F_D10 primer

<400> SEQUENCE: 59
tggagagccg gcctccatct cctg                                                24

<210> SEQ ID NO 60
<211> LENGTH: 36
<212> TYPE: DNA
<213> ORGANISM: Artificial Sequence
<220> FEATURE:
<223> OTHER INFORMATION: pGEXF_IGK_V_02-38_P_D10 primer

<400> SEQUENCE: 60
ataatatttg tacataactt tgtacttcat ctcctg                                   36

<210> SEQ ID NO 61
<211> LENGTH: 28
<212> TYPE: DNA
<213> ORGANISM: Artificial Sequence
<220> FEATURE:
<223> OTHER INFORMATION: pGEXF_IGK_V_2D-14_P_D10 primer

<400> SEQUENCE: 61
cccctggaaa gccagcctct atctcctg                                            28
```

<210> SEQ ID NO 62
<211> LENGTH: 32
<212> TYPE: DNA
<213> ORGANISM: Artificial Sequence
<220> FEATURE:
<223> OTHER INFORMATION: pGEXF_IGK_V_2D-19_P_D10 primer

<400> SEQUENCE: 62
ctcttccttg gagagccatc ctccatttcc tg          32

<210> SEQ ID NO 63
<211> LENGTH: 23
<212> TYPE: DNA
<213> ORGANISM: Artificial Sequence
<220> FEATURE:
<223> OTHER INFORMATION: pGEXF_IGK_V_2D-24_O_D10 primer

<400> SEQUENCE: 63
ggacagccgg cctccatctc ctt          23

<210> SEQ ID NO 64
<211> LENGTH: 26
<212> TYPE: DNA
<213> ORGANISM: Artificial Sequence
<220> FEATURE:
<223> OTHER INFORMATION: pGEXF_IGK_V_2D-26_F_D10 primer

<400> SEQUENCE: 64
cctggagagc aggcctccat gtcctg          26

<210> SEQ ID NO 65
<211> LENGTH: 26
<212> TYPE: DNA
<213> ORGANISM: Artificial Sequence
<220> FEATURE:
<223> OTHER INFORMATION: pGEXF_IGK_V_03-07_F_D10 primer

<400> SEQUENCE: 65 ccagggaaa gagccaccct ctcctg          26

<210> SEQ ID NO 66
<211> LENGTH: 27
<212> TYPE: DNA
<213> ORGANISM: Artificial Sequence
<220> FEATURE:
<223> OTHER INFORMATION: pGEXF_IGK_V_03-07_P_D10 primer

<400> SEQUENCE: 66
tccaggggaa agagtcaccc tctcctg          27

<210> SEQ ID NO 67
<211> LENGTH: 35
<212> TYPE: DNA
<213> ORGANISM: Artificial Sequence
<220> FEATURE:
<223> OTHER INFORMATION: pGEXF_IGK_V_03-25_P_D10 primer

<400> SEQUENCE: 67
tctttgtctc tggagaaaaa agccaccctg acttg          35

<210> SEQ ID NO 68
<211> LENGTH: 29
<212> TYPE: DNA
<213> ORGANISM: Artificial Sequence
<220> FEATURE:
<223> OTHER INFORMATION: pGEXF_IGK_V_03-31_P_D10 primer

```
<400> SEQUENCE: 68
tctctagggg aaaaagccac cctcaccta                                        29

<210> SEQ ID NO 69
<211> LENGTH: 23
<212> TYPE: DNA
<213> ORGANISM: Artificial Sequence
<220> FEATURE:
<223> OTHER INFORMATION: pGEXF_IGK_V_03-34_P_D10 primer

<400> SEQUENCE: 69
ggggaaggag ccaccctcac ctg                                              23

<210> SEQ ID NO 70
<211> LENGTH: 24
<212> TYPE: DNA
<213> ORGANISM: Artificial Sequence
<220> FEATURE:
<223> OTHER INFORMATION: pGEXF_IGK_V_04-01_F_D10 primer

<400> SEQUENCE: 70
gggcgagagg gccaccatca actg                                             24

<210> SEQ ID NO 71
<211> LENGTH: 32
<212> TYPE: DNA
<213> ORGANISM: Artificial Sequence
<220> FEATURE:
<223> OTHER INFORMATION: pGEXF_IGK_V_05-02_F_D10 primer

<400> SEQUENCE: 71
gcgactccag gagacaaagt caacatctcc tg                                    32

<210> SEQ ID NO 72
<211> LENGTH: 34
<212> TYPE: DNA
<213> ORGANISM: Artificial Sequence
<220> FEATURE:
<223> OTHER INFORMATION: pGEXF_IGK_V_06-21_O_D10 primer

<400> SEQUENCE: 72
ctgtgactcc aaaggagaaa gtcaccatca cctg                                  34

<210> SEQ ID NO 73
<211> LENGTH: 29
<212> TYPE: DNA
<213> ORGANISM: Artificial Sequence
<220> FEATURE:
<223> OTHER INFORMATION: pGEXF_IGK_V_6D-41_F_D10 primer

<400> SEQUENCE: 73
actccagggg agaaagtcac catcacctg                                        29

<210> SEQ ID NO 74
<211> LENGTH: 25
<212> TYPE: DNA
<213> ORGANISM: Artificial Sequence
<220> FEATURE:
<223> OTHER INFORMATION: pGEXF_IGK_V_07-03_P_D10 primer

<400> SEQUENCE: 74
caggacagag ggccaccatc acctg                                            25

<210> SEQ ID NO 75
```

```
<211> LENGTH: 26
<212> TYPE: DNA
<213> ORGANISM: Artificial Sequence
<220> FEATURE:
<223> OTHER INFORMATION: pGEXF_IGL_V_01-36_F_D10 primer

<400> SEQUENCE: 75
cccaggcaga gggtcaccat ctcctg                                              26

<210> SEQ ID NO 76
<211> LENGTH: 26
<212> TYPE: DNA
<213> ORGANISM: Artificial Sequence
<220> FEATURE:
<223> OTHER INFORMATION: pGEXF_IGL_V_01-40_F_D10 primer

<400> SEQUENCE: 76
ccagggcaga gggtcaccat ctcctg                                              26

<210> SEQ ID NO 77
<211> LENGTH: 25
<212> TYPE: DNA
<213> ORGANISM: Artificial Sequence
<220> FEATURE:
<223> OTHER INFORMATION: pGEXF_IGL_V_01-44_F_D10 primer

<400> SEQUENCE: 77
ccgggcagag ggtcaccatc tcttg                                               25

<210> SEQ ID NO 78
<211> LENGTH: 28
<212> TYPE: DNA
<213> ORGANISM: Artificial Sequence
<220> FEATURE:
<223> OTHER INFORMATION: pGEXF_IGL_V_01-51_F_D10 primer

<400> SEQUENCE: 78
ccccaggaca gaaggtcacc atctcctg                                            28

<210> SEQ ID NO 79
<211> LENGTH: 28
<212> TYPE: DNA
<213> ORGANISM: Artificial Sequence
<220> FEATURE:
<223> OTHER INFORMATION: pGEXF_IGL_V_01-62_P_D10 primer

<400> SEQUENCE: 79
ccacaaggca gaggctcact gtctcctg                                            28

<210> SEQ ID NO 80
<211> LENGTH: 30
<212> TYPE: DNA
<213> ORGANISM: Artificial Sequence
<220> FEATURE:
<223> OTHER INFORMATION: pGEXF_IGL_V_02-08_F_D10 primer

<400> SEQUENCE: 80
gtctcctgga cagtcagtca ccatctcctg                                          30

<210> SEQ ID NO 81
<211> LENGTH: 30
<212> TYPE: DNA
<213> ORGANISM: Artificial Sequence
<220> FEATURE:
<223> OTHER INFORMATION: pGEXF_IGL_V_02-14_F_D10 primer

<400> SEQUENCE: 81
```
gtctcctgga cagtcgatca ccatctcctg                                        30

<210> SEQ ID NO 82
<211> LENGTH: 27
<212> TYPE: DNA
<213> ORGANISM: Artificial Sequence
<220> FEATURE:
<223> OTHER INFORMATION: pGEXF_IGL_V_02-33_O_D10 primer

<400> SEQUENCE: 82
tcctggacag tcggtcacca tctcctg                                           27

<210> SEQ ID NO 83
<211> LENGTH: 33
<212> TYPE: DNA
<213> ORGANISM: Artificial Sequence
<220> FEATURE:
<223> OTHER INFORMATION: pGEXF_IGL_V_02-34_P_D10 primer

<400> SEQUENCE: 83
ctgggacttg gggtaaacag tcaccatctt ctg                                    33

<210> SEQ ID NO 84
<211> LENGTH: 26
<212> TYPE: DNA
<213> ORGANISM: Artificial Sequence
<220> FEATURE:
<223> OTHER INFORMATION: pGEXF_IGL_V_03-01_F_D10 primer

<400> SEQUENCE: 84
ccaggacaga cagccagcat cacctg                                            26

<210> SEQ ID NO 85
<211> LENGTH: 28
<212> TYPE: DNA
<213> ORGANISM: Artificial Sequence
<220> FEATURE:
<223> OTHER INFORMATION: pGEXF_IGL_V_03-02_P_D10 primer

<400> SEQUENCE: 85
ctttgggacg tacggccagg atcatctg                                          28

<210> SEQ ID NO 86
<211> LENGTH: 28
<212> TYPE: DNA
<213> ORGANISM: Artificial Sequence
<220> FEATURE:
<223> OTHER INFORMATION: pGEXF_IGL_V_03-04_P_D10 primer

<400> SEQUENCE: 86
ctttgggaca gatggccagg atcacctg                                          28

<210> SEQ ID NO 87
<211> LENGTH: 26
<212> TYPE: DNA
<213> ORGANISM: Artificial Sequence
<220> FEATURE:
<223> OTHER INFORMATION: pGEXF_IGL_V_03-06_P_D10 primer

<400> SEQUENCE: 87
ccaggacagg cagccatgat cacctg                                            26

<210> SEQ ID NO 88
<211> LENGTH: 25
<212> TYPE: DNA

```
<213> ORGANISM: Artificial Sequence
<220> FEATURE:
<223> OTHER INFORMATION: pGEXF_IGL_V_03-07_P_D10 primer

<400> SEQUENCE: 88
tgggacagag ggccaggatc accta                                          25

<210> SEQ ID NO 89
<211> LENGTH: 24
<212> TYPE: DNA
<213> ORGANISM: Artificial Sequence
<220> FEATURE:
<223> OTHER INFORMATION: pGEXF_IGL_V_03-09_FP_D10 primer

<400> SEQUENCE: 89
gggacaggcg gccaggatta cctg                                           24

<210> SEQ ID NO 90
<211> LENGTH: 26
<212> TYPE: DNA
<213> ORGANISM: Artificial Sequence
<220> FEATURE:
<223> OTHER INFORMATION: pGEXF_IGL_V_03-10_F_D10 primer

<400> SEQUENCE: 90
ccaggacaaa cggccaggat cacctg                                         26

<210> SEQ ID NO 91
<211> LENGTH: 27
<212> TYPE: DNA
<213> ORGANISM: Artificial Sequence
<220> FEATURE:
<223> OTHER INFORMATION: pGEXF_IGL_V_03-12_F_D10 primer

<400> SEQUENCE: 91
cacagcacag atggccagga tcacctg                                        27

<210> SEQ ID NO 92
<211> LENGTH: 26
<212> TYPE: DNA
<213> ORGANISM: Artificial Sequence
<220> FEATURE:
<223> OTHER INFORMATION: pGEXF_IGL_V_03-13_P_D10 primer

<400> SEQUENCE: 92
ccaggacaga cagccaggat cagctg                                         26

<210> SEQ ID NO 93
<211> LENGTH: 28
<212> TYPE: DNA
<213> ORGANISM: Artificial Sequence
<220> FEATURE:
<223> OTHER INFORMATION: pGEXF_IGL_V_03-15_P_D10 primer

<400> SEQUENCE: 93
ccccaggaca gatgaccagg atcacctg                                       28

<210> SEQ ID NO 94
<211> LENGTH: 28
<212> TYPE: DNA
<213> ORGANISM: Artificial Sequence
<220> FEATURE:
<223> OTHER INFORMATION: pGEXF_IGL_V_03-16_F_D10 primer

<400> SEQUENCE: 94
ccctaggaca gatggccagg atcacctg                                       28
```

<210> SEQ ID NO 95
<211> LENGTH: 31
<212> TYPE: DNA
<213> ORGANISM: Artificial Sequence
<220> FEATURE:
<223> OTHER INFORMATION: pGEXF_IGL_V_03-17_P_D10 primer

<400> SEQUENCE: 95
gtgtctgtgg acagtcagca agggtaacct g                          31

<210> SEQ ID NO 96
<211> LENGTH: 30
<212> TYPE: DNA
<213> ORGANISM: Artificial Sequence
<220> FEATURE:
<223> OTHER INFORMATION: pGEXF_IGL_V_03-19_F_D10 primer

<400> SEQUENCE: 96
ggccttggga cagacagtca ggatcacatg                            30

<210> SEQ ID NO 97
<211> LENGTH: 28
<212> TYPE: DNA
<213> ORGANISM: Artificial Sequence
<220> FEATURE:
<223> OTHER INFORMATION: pGEXF_IGL_V_03-21_F_D10 primer

<400> SEQUENCE: 97
ccccaggaaa gacggccagg attacctg                              28

<210> SEQ ID NO 98
<211> LENGTH: 27
<212> TYPE: DNA
<213> ORGANISM: Artificial Sequence
<220> FEATURE:
<223> OTHER INFORMATION: pGEXF_IGL_V_03-22_FP_D10 primer

<400> SEQUENCE: 98
cccaggacag aaagccagga tcacctg                               27

<210> SEQ ID NO 99
<211> LENGTH: 34
<212> TYPE: DNA
<213> ORGANISM: Artificial Sequence
<220> FEATURE:
<223> OTHER INFORMATION: pGEXF_IGL_V_03-24_P_D10 primer

<400> SEQUENCE: 99
cagtagctcc aggacagatg actaggatca cctg                       34

<210> SEQ ID NO 100
<211> LENGTH: 25
<212> TYPE: DNA
<213> ORGANISM: Artificial Sequence
<220> FEATURE:
<223> OTHER INFORMATION: pGEXF_IGL_V_03-25_F_D10 primer

<400> SEQUENCE: 100
caggacagac ggccaggatc acctg                                 25

<210> SEQ ID NO 101
<211> LENGTH: 27
<212> TYPE: DNA
<213> ORGANISM: Artificial Sequence
<220> FEATURE:

```
<223> OTHER INFORMATION: pGEXF_IGL_V_03-26_P_D10 primer

<400> SEQUENCE: 101
cctgggacag tcagccaggg taacctg                                27

<210> SEQ ID NO 102
<211> LENGTH: 25
<212> TYPE: DNA
<213> ORGANISM: Artificial Sequence
<220> FEATURE:
<223> OTHER INFORMATION: pGEXF_IGL_V_03-27_F_D10 primer

<400> SEQUENCE: 102
cgggacagac agccaggatc acctg                                  25

<210> SEQ ID NO 103
<211> LENGTH: 27
<212> TYPE: DNA
<213> ORGANISM: Artificial Sequence
<220> FEATURE:
<223> OTHER INFORMATION: pGEXF_IGL_V_03-29_P_D10 primer

<400> SEQUENCE: 103
cccaggacag acacccagga tcacctg                                27

<210> SEQ ID NO 104
<211> LENGTH: 28
<212> TYPE: DNA
<213> ORGANISM: Artificial Sequence
<220> FEATURE:
<223> OTHER INFORMATION: pGEXF_IGL_V_03-30_P_D10 primer

<400> SEQUENCE: 104
ccccattaca gatggccagg atcacctg                               28

<210> SEQ ID NO 105
<211> LENGTH: 29
<212> TYPE: DNA
<213> ORGANISM: Artificial Sequence
<220> FEATURE:
<223> OTHER INFORMATION: pGEXF_IGL_V_03-31_P_D10 primer

<400> SEQUENCE: 105
gccttgggat agacagccag gatcacctg                              29

<210> SEQ ID NO 106
<211> LENGTH: 28
<212> TYPE: DNA
<213> ORGANISM: Artificial Sequence
<220> FEATURE:
<223> OTHER INFORMATION: pGEXF_IGL_V_03-32_O_D10 primer

<400> SEQUENCE: 106
ccttgggaca aatggccagg atcacctg                               28

<210> SEQ ID NO 107
<211> LENGTH: 26
<212> TYPE: DNA
<213> ORGANISM: Artificial Sequence
<220> FEATURE:
<223> OTHER INFORMATION: pGEXF_IGL_V_04-03_F_D10 primer

<400> SEQUENCE: 107
ctgggagcct cgatcaagct cacctg                                 26
```

```
<210> SEQ ID NO 108
<211> LENGTH: 27
<212> TYPE: DNA
<213> ORGANISM: Artificial Sequence
<220> FEATURE:
<223> OTHER INFORMATION: pGEXF_IGL_V_04-60_F_D10 primer

<400> SEQUENCE: 108
cctgggatcc tcggtcaagc tcacctg                                        27

<210> SEQ ID NO 109
<211> LENGTH: 24
<212> TYPE: DNA
<213> ORGANISM: Artificial Sequence
<220> FEATURE:
<223> OTHER INFORMATION: pGEXF_IGL_V_04-69_F_D10 primer

<400> SEQUENCE: 109
gggagcctcg gtcaagctca cctg                                           24

<210> SEQ ID NO 110
<211> LENGTH: 27
<212> TYPE: DNA
<213> ORGANISM: Artificial Sequence
<220> FEATURE:
<223> OTHER INFORMATION: pGEXF_IGL_V_05-37_F_D10 primer

<400> SEQUENCE: 110
tcctggagaa tccgccagac tcacctg                                        27

<210> SEQ ID NO 111
<211> LENGTH: 29
<212> TYPE: DNA
<213> ORGANISM: Artificial Sequence
<220> FEATURE:
<223> OTHER INFORMATION: pGEXF_IGL_V_05-39_F_D10 primer

<400> SEQUENCE: 111
tctcctggag catcagccag attcacctg                                      29

<210> SEQ ID NO 112
<211> LENGTH: 27
<212> TYPE: DNA
<213> ORGANISM: Artificial Sequence
<220> FEATURE:
<223> OTHER INFORMATION: pGEXF_IGL_V_05-45_F_D10 primer

<400> SEQUENCE: 112
tcctggagca tcagccagtc tcacctg                                        27

<210> SEQ ID NO 113
<211> LENGTH: 27
<212> TYPE: DNA
<213> ORGANISM: Artificial Sequence
<220> FEATURE:
<223> OTHER INFORMATION: pGEXF_IGL_V_05-48_O_D10 primer

<400> SEQUENCE: 113
tcctggagca tcagccagac tcacctg                                        27

<210> SEQ ID NO 114
<211> LENGTH: 32
<212> TYPE: DNA
<213> ORGANISM: Artificial Sequence
<220> FEATURE:
<223> OTHER INFORMATION: pGEXF_IGL_V_05-52_F_D10 primer
```

<400> SEQUENCE: 114
gcatcttctg gagcatcagt cagactcacc tg    32

<210> SEQ ID NO 115
<211> LENGTH: 27
<212> TYPE: DNA
<213> ORGANISM: Artificial Sequence
<220> FEATURE:
<223> OTHER INFORMATION: pGEXF_IGL_V_07-35_P_D10 primer

<400> SEQUENCE: 115
cccaggaggg acagtcactc tcaccta    27

<210> SEQ ID NO 116
<211> LENGTH: 27
<212> TYPE: DNA
<213> ORGANISM: Artificial Sequence
<220> FEATURE:
<223> OTHER INFORMATION: pGEXF_IGL_V_07-43_F_D10 primer

<400> SEQUENCE: 116
cccaggaggg acagtcactc tcacctg    27

<210> SEQ ID NO 117
<211> LENGTH: 28
<212> TYPE: DNA
<213> ORGANISM: Artificial Sequence
<220> FEATURE:
<223> OTHER INFORMATION: pGEXF_IGL_V_08-61_F_D10 primer

<400> SEQUENCE: 117
cccctggagg gacagtcaca ctcacttg    28

<210> SEQ ID NO 118
<211> LENGTH: 25
<212> TYPE: DNA
<213> ORGANISM: Artificial Sequence
<220> FEATURE:
<223> OTHER INFORMATION: pGEXF_IGL_V_09-49_F_D10 primer

<400> SEQUENCE: 118
tgggagcctc ggtcacactc acctg    25

<210> SEQ ID NO 119
<211> LENGTH: 27
<212> TYPE: DNA
<213> ORGANISM: Artificial Sequence
<220> FEATURE:
<223> OTHER INFORMATION: pGEXF_IGL_V_10-54_F_D10 primer

<400> SEQUENCE: 119
cttgagacag accgccacac tcacctg    27

<210> SEQ ID NO 120
<211> LENGTH: 37
<212> TYPE: DNA
<213> ORGANISM: Artificial Sequence
<220> FEATURE:
<223> OTHER INFORMATION: PGEXF_IGK_V_del_D10 primer

<400> SEQUENCE: 120
gtaaataatt gcattttta atgaccgtgg gtctgtg    37

<210> SEQ ID NO 121
<211> LENGTH: 32

<212> TYPE: DNA
<213> ORGANISM: Artificial Sequence
<220> FEATURE:
<223> OTHER INFORMATION: pGEXR_IGK_J_01_F_D10 primer

<400> SEQUENCE: 121
ttctactcac gtttgatttc caccttggtc cc                                    32

<210> SEQ ID NO 122
<211> LENGTH: 32
<212> TYPE: DNA
<213> ORGANISM: Artificial Sequence
<220> FEATURE:
<223> OTHER INFORMATION: pGEXr_IGK_J_02_F_D10 primer

<400> SEQUENCE: 122
aagtacttac gtttgatctc cagcttggtc cc                                    32

<210> SEQ ID NO 123
<211> LENGTH: 36
<212> TYPE: DNA
<213> ORGANISM: Artificial Sequence
<220> FEATURE:
<223> OTHER INFORMATION: pGEXr_IGK_J_03_F_D10 primer

<400> SEQUENCE: 123
acagatgtac ttacgtttga tatccacttt ggtccc                                36

<210> SEQ ID NO 124
<211> LENGTH: 29
<212> TYPE: DNA
<213> ORGANISM: Artificial Sequence
<220> FEATURE:
<223> OTHER INFORMATION: pGEXr_IGK_J_04_F_D10 primer

<400> SEQUENCE: 124
cacttacgtt tgatctccac cttggtccc                                        29

<210> SEQ ID NO 125
<211> LENGTH: 36
<212> TYPE: DNA
<213> ORGANISM: Artificial Sequence
<220> FEATURE:
<223> OTHER INFORMATION: pGEXr_IGK_J_05_F_D10 primer

<400> SEQUENCE: 125
gaaaaattac ttacgtttaa tctccagtcg tgtccc                                36

<210> SEQ ID NO 126
<211> LENGTH: 27
<212> TYPE: DNA
<213> ORGANISM: Artificial Sequence
<220> FEATURE:
<223> OTHER INFORMATION: pGEXr_IGL_J_01_F_D10 primer

<400> SEQUENCE: 126
cttacctagg acggtgacct tggtccc                                          27

<210> SEQ ID NO 127
<211> LENGTH: 24
<212> TYPE: DNA

```
<213> ORGANISM: Artificial Sequence
<220> FEATURE:
<223> OTHER INFORMATION: pGEXr_IGL_J_02_F_D10 primer

<400> SEQUENCE: 127
acctaggacg gtcagcttgg tccc                                              24

<210> SEQ ID NO 128
<211> LENGTH: 36
<212> TYPE: DNA
<213> ORGANISM: Artificial Sequence
<220> FEATURE:
<223> OTHER INFORMATION: pGEXr_IGL_J_04_O_D10 primer

<400> SEQUENCE: 128
aagaagagac tcatctaaaa tgatcagctg ggttcc                                 36

<210> SEQ ID NO 129
<211> LENGTH: 24
<212> TYPE: DNA
<213> ORGANISM: Artificial Sequence
<220> FEATURE:
<223> OTHER INFORMATION: pGEXr_IGL_J_05_O_D10 primer

<400> SEQUENCE: 129
atctaggacg gtcagctccg tccc                                              24

<210> SEQ ID NO 130
<211> LENGTH: 21
<212> TYPE: DNA
<213> ORGANISM: Artificial Sequence
<220> FEATURE:
<223> OTHER INFORMATION: pGEXr_IGL_J_06_F_D10 primer

<400> SEQUENCE: 130
gaggacggtc accttggtgc c                                                 21

<210> SEQ ID NO 131
<211> LENGTH: 20
<212> TYPE: DNA
<213> ORGANISM: Artificial Sequence
<220> FEATURE:
<223> OTHER INFORMATION: pGEXr_IGL_J_07_F_D10 primer

<400> SEQUENCE: 131
aggacggtca gctgggtgcc                                                   20

<210> SEQ ID NO 132
<211> LENGTH: 24
<212> TYPE: DNA
<213> ORGANISM: Artificial Sequence
<220> FEATURE:
<223> OTHER INFORMATION: pGEXr_IGK_J_del_F_D10 primer

<400> SEQUENCE: 132
ctgcagactc atgaggagtc gccc                                              24
```

IDENTIFICATION OF ANTIGEN-SPECIFIC B CELL RECEPTORS

REFERENCE TO RELATED APPLICATIONS

This application claims priority to U.S. Provisional Application No. 62/397,811, filed Sep. 21, 2016, the contents of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (file name: ADBS_033_02US_SeqList_ST25.txt; date recorded: Sep. 20, 2017; file size: 26.7 kilobytes).

BACKGROUND OF THE INVENTION

Immunoglobulins (Igs) expressed by B-cells, also referred to herein as B-cell receptors (BCR), are proteins consisting of four polypeptide chains, two heavy chains (H chains) from the IGH locus and two light chains (L chains) from either the IGK (kappa) or the IGL (lambda) locus, forming an $H_2L_2$ structure. Both H and L chains contain complementarity determining regions (CDR) involved in antigen recognition, and a constant domain. The H chains of Igs are initially expressed as membrane-bound isoforms using either the IgM or IgD constant region isoform, but after antigen recognition the H chain constant region can class switch to several additional isotypes, including IgG, IgE and IgA. The diversity of naïve Igs within an individual is mainly determined by the hypervariable complementarity determining regions (CDR). The CDR3 domain of IGH chains is created by the combinatorial joining of the $V_H$, $D_H$, and $J_H$ gene segments. Hypervariable domain sequence diversity is further increased by independent addition and deletion of nucleotides at the $V_H$-$D_H$, $D_H$-$J_H$, and $V_H$-$J_H$ junctions during the process of IG gene rearrangement. Ig sequence diversity is further augmented by somatic hypermutation (SHM) throughout the rearranged IG gene after a naïve B cell initially recognizes an antigen. The process of SHM is not restricted to CDR3, and therefore can introduce changes in the germline sequence in framework regions, CDR1 and CDR2, as well as in the somatically rearranged CDR3.

As the adaptive immune system functions in part by clonal expansion of cells expressing unique BCRs, accurately measuring the changes in total abundance of each clone is important to understanding the dynamics of an adaptive immune response. Utilizing advances in high-throughput sequencing, a new field of molecular immunology has recently emerged to profile the vast BCR repertoires. Compositions and methods for the sequencing of rearranged adaptive immune receptor gene sequences and for adaptive immune receptor clonotype determination are described, for example, in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. Patent Application Nos. 61/550,311 and 61/569,118; US Patent Application Publication Nos. US 2012-0058902 and US 2010-0330571; and International PCT Publication Nos. WO 2010/151416, WO 2011/106738, and WO 2012/027503, all of which are herein incorporated by reference.

The sequence of the BCR repertoire yields complex DNA samples in which accurate determination of the multiple distinct sequences contained therein is hindered by technical limitations on the ability to quantify a plurality of molecular species simultaneously using multiplexed amplification and high throughput sequencing. In addition, it is difficult from existing methodologies to sequence quantitatively DNA or RNA encoding both chains of a BCR heterodimer in a manner that permits determination that both chains originated from the same lymphoid cell.

One or more factors can give rise to artifacts that skew sequencing data outputs, compromising the ability to obtain reliable quantitative data from sequencing strategies that are based on multiplexed amplification of a highly diverse collection of IG gene templates. These artifacts often result from unequal use of diverse primers during the multiplexed amplification step. Such biased utilization of one or more oligonucleotide primers in a multiplexed reaction that uses diverse amplification templates may arise as a function of one or more of differences in the nucleotide base composition of templates and/or oligonucleotide primers, differences in template and/or primer length, the particular polymerase that is used, the amplification reaction temperatures (e.g., annealing, elongation and/or denaturation temperatures), and/or other factors (e.g., Kanagawa, 2003 *J. Biosci. Bioeng.* 96:317; Day et al., 1996 *Hum. Mol. Genet.* 5:2039; Ogino et al., 2002 *J. Mol. Diagnost.* 4:185; Barnard et al., 1998 *Biotechniques* 25:684; Aird et al., 2011 *Genome Biol.* 12:R18).

The identification of paired light and heavy chains from a single B-cell is only one half of the equation regarding immuno-surveillance of antigens/epitopes that are recognized by the adaptive immune system. In the absence of the ability to identify B-cell receptors in the diverse BCR repertoire that bind to corresponding epitopes/antigens, the sequenced BCR profile does not allow for the ability to draw direct correlations between the presence of a specific BCR sequence and the presence of a corresponding epitope/antigen of a pathogen or cancer.

A BCR-specific epitope display library or a BCR-specific antigen display library is the result of introducing B-cells with an extracellular BCR into a solution comprising a genetic conveyance of random or specific antigens to which the BCRs may bind to, and which the BCR heterodimers can be linked to a specific antigen, thus allowing for the correlation of specific BCR sequences to specific antigens. Methods of utilizing phage display for serological profiling are described in Xu et al. Science. 348(6239): aaa0698.

Conventional techniques have focused on determining antigen specificity using antibodies (soluble forms of BCRs), but have not been able to directly assess BCR specificity to antigens. Current methods are not able to simultaneously determine antigen-specific BCRs on a large scale. Antigen-specificity of rare B cells is also difficult to achieve using current techniques.

Clearly there remains a need for identifying antigen-specific BCRs in a high throughput and accurate method. In particular, there exists a need for (1) improved compositions and methods that will permit accurate quantification of adaptive immune receptor-encoding DNA and RNA sequence diversity in complex samples, in a manner that avoids skewed results, for example, from amplification bias, and in a manner that permits determination of the coding sequences for both chains of a BCR heterodimer that originate from the same lymphoid cell; and (2) matching the heterodimers to a corresponding epitope/antigen binding partner to identify BCRs that bind a particular epitope or antigen of interest. The presently described embodiments address this need and provide other related advantages.

SUMMARY OF THE INVENTION

The present invention is based, in part, on methods of identifying antigen-specific B-cell receptor (BCR) sequences with the use of antigen display libraries.

In some embodiments, the present invention provides a method for identifying antigen-specific BCR sequences comprising: (A) incubating a plurality of B-cells with an antigen library displayed by an organism capable of displaying antigens; (B) distributing the B-cells bound to antigens of the antigen library into a plurality of aliquots; (C) isolating nucleic acids from B-cells bound to antigens of the antigen library and from the organism displaying said antigens; sequencing the following elements from each of the aliquots; (i) B-cell heavy chain sequence, (ii) B-cell light chain sequence, and (iii) a nucleotide sequence encoding the antigen bound to the BCR; and (E) identifying the sequenced elements of (D) that occur together in more than one aliquot thereby identifying antigen-specific BCR sequences.

In some embodiments, (A) is immediately followed by enriching for B-cells bound to species of the antigen library. In some embodiments, the enriching of B-cells bound to species of the antigen library comprises flow cytometry.

In some embodiments, (C) is immediately followed by generating a library of amplicons by performing multiplex PCR on the isolated nucleic acids.

In some embodiments, the plurality of B-cells are isolated from a human. In some embodiments, the plurality of B-cells comprises at least $10^4$ cells. In some embodiments, the B-cells express B-cell receptors on the cell surface.

In some embodiments, the antigen library is a phage display library, a bacterial surface display library, or a yeast surface display library. In further embodiments, the antigen library comprises antigens selected from the group consisting of bacterial antigens, viral antigens, fungal antigens, protist antigens, plant antigens, vertebrate antigens, mammalian antigens, or any combination thereof. In some embodiments, the antigen library comprises a whole-genome library of an organism. In some embodiments, the organism is a mammalian pathogen. In further embodiments, the mammalian pathogen is a human pathogen.

In some embodiments, the antigen library comprises a plurality of antigens, and the nucleotide sequence encoding each antigen is flanked by a synthetic polynucleotide sequence. In further embodiments, the synthetic polynucleotide sequence comprises at least one barcode sequence. In further embodiments, the synthetic polynucleotide sequence comprises at least one universal adaptor sequence flanking the antigen. In further embodiments, the synthetic polynucleotide comprises at least one universal adaptor sequence, a sequencing platform tag sequence, and at least one barcode sequence.

In some embodiments, the nucleotide sequence encoding the antigen is a cDNA.

In some embodiments, the method further comprises: (i) for each aliquot, reverse transcribing mRNA comprising rearranged CDR3 regions of the B-cells using oligonucleotide reverse transcription primers that direct incorporation of an oligonucleotide barcode and a universal adapter resulting in cDNA from each of the light and heavy chain sequences comprising a barcode and a universal adaptor, such that amplicons in an aliquot comprises the same unique barcode; (ii) amplifying the cDNA using amplification primers to obtain amplification products; (iii) quantitatively sequencing the amplification products of (ii) to obtain a data set of sequences that includes the B-cell light and heavy chain sequences and associated barcodes for each aliquot; (iv) sorting amplification products based on the unique barcode to identify light and heavy chain sequences that were amplified from the same aliquot and determining an aliquot occupancy pattern for each unique light and heavy chain sequence; and (v) identifying light and heavy chain sequences as paired immune receptor chains based on whether the sequences occur together or do not occur together in a plurality of aliquots based on a statistical probability of observing said aliquot occupancy pattern.

In some embodiments, the oligonucleotide reverse transcription primers that are contacted with the contents of a single aliquot share a common barcode sequence. In some embodiments, the amplification primers further comprise an additional barcode, an n6 spacer, and/or a sequencing oligonucleotide. In some embodiments, the amplification primers specifically hybridize to the universal adapter added to the cDNA in step (ii). In some embodiments, the reverse transcription primers specifically hybridize to V, J, or C segments of each rearranged DNA sequence encoding a light chain and heavy chain polypeptide. In some embodiments, further comprising clustering the sorted amplification products in step (iv) based on the V, J, and/or C segments of each rearranged DNA sequence.

In some embodiments, the method for identifying antigen-specific BCR sequences comprises: (A) incubating a plurality of B-cells with a phage antigen display library; (B) distributing the B-cells bound to antigens of the antigen library into a plurality of aliquots; (C) isolating mRNA from B-cells bound to antigens of the antigen library and nucleic acids from the phage; (D) for each aliquot, reverse transcribing mRNA comprising rearranged CDR3 regions of the B-cells using oligonucleotide reverse transcription primers that direct incorporation of an oligonucleotide barcode and a universal adapter resulting in cDNA from each of the light and heavy chain sequences comprising a barcode and a universal adaptor, wherein each of the oligonucleotide reverse transcription primers that are contacted with the contents of a single aliquot share a common barcode sequence; (E) amplifying the light and heavy chain cDNA sequences using amplification primers to obtain amplification products; (F) quantitatively sequencing the amplification products of (E) to obtain a data set of sequences that includes the B-cell light and heavy chain sequences and associated barcodes for each aliquot; (G) sorting amplification products based on the unique barcode to identify light and heavy chain sequences that were amplified from the same aliquot and determining an aliquot occupancy pattern for each unique light and heavy chain sequence; (H) identifying light and heavy chain sequences as paired immune receptor chains based on whether the sequences occur together or do not occur together in a plurality of aliquots based on a statistical probability of observing said aliquot occupancy pattern; (I) generating a library of amplicons by performing PCR on the isolated nucleic acids from the phage, followed by sequencing the library of amplicons; and (J) identifying the paired immune receptor chains in (H) and the nucleic acids in (I) based on whether the sequences occur together or do not occur together in a plurality of aliquots.

In some embodiments, the amplification primers further comprise an additional barcode, an n6 spacer, and/or a sequencing oligonucleotide.

In some embodiments, the amplification primers specifically hybridize to the universal adapter added to the cDNA in (E).

In some embodiments, the the reverse transcription primers specifically hybridize to V, J, or C segments of each rearranged DNA sequence encoding a light chain and heavy chain polypeptide. In some embodiments, the method further comprises clustering the sorted amplification products in (G) based on the V, J, and/or C segments of each rearranged DNA sequence.

In some embodiments, the isolated nucleic acids from the phage comprise RNA, step (I) is immediately preceded by reverse transcribing RNA comprising antigens of the antigen display library.

BRIEF DESCRIPTION OF THE DRAWINGS

FIG. 1 depicts a schematic depicts a schematic representation of certain herein described compositions and methods. U1 and U2 represent universal adaptor oligonucleotides. BC1 and BC2 represent barcode oligonucleotides. J represents an adaptive immune receptor joining (J) region gene and Jpr represents a region of such a gene to which a J-specific oligonucleotide primer specifically anneals. V represents an adaptive immune receptor variable (V) region gene and Vpr represents a region of such a gene to which a V-specific oligonucleotide primer specifically anneals. NDN represents the diversity (D) region found in some adaptive immune receptor encoding genes, flanked on either side by junctional nucleotides (N) which may include non-templated nucleotides. Adap1 and Adap2 represent sequencing platform-specific adapters. The segment shown as "n6" represents a spacer nucleotide segment of any nucleotide sequence, in this case, a spacer of six randomly selected nucleotides.

DETAILED DESCRIPTION OF THE INVENTION

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

The term "isolated" means that the material is removed from its original environment (e.g., the natural environment if it is naturally occurring). For example, a naturally occurring tissue, cell, nucleic acid or polypeptide present in its original milieu in a living animal is not isolated, but the same tissue, cell, nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

The terms "bacteriophage" and "phage" are used interchangeably herein and refer to viruses which infect bacteria. By the use of the terms "bacteriophage library" or "phage library" as used herein, is meant a population of bacterial viruses comprising heterologous DNA, i.e., DNA which is not naturally encoded by the bacterial virus.

A polynucleotide is "heterologous" to an organism or a second polynucleotide sequence if it originates from a foreign species, or, if from the same species, is modified from its original (native or naturally occurring) form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

Unless the context requires otherwise, throughout the present specification and claims, the word "comprise" and variations thereof, such as, "comprises" and "comprising" are to be construed in an open, inclusive sense, that is, as "including, but not limited to." By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub ranges subsumed therein. For example, a stated range of from "1 to 10" should be considered to include any and all sub ranges between the minimum value of 1 and the maximum value of 10. Exemplary sub ranges of the range "1 to 10" include, but are not limited to, 1 to 6.1, 3.5 to 7.8, and 5.5 to 10.

Cells and Vectors

Any cell into which a construct of the disclosure may be introduced and expressed is useful according to the disclosure. That is, because of the wide variety of uses for the constructs of the disclosure, any cell in which a construct of the disclosure may be expressed, and optionally detected, is a suitable host. The construct may exist in a host cell as an extrachromosomal element or be integrated into the host genome.

A host cell may be prokaryotic, such as any of a number of bacterial strains, or may be eukaryotic, such as yeast or other fungal cells, insect, plant, amphibian, or mammalian cells including, for example, rodent, simian or human cells. A host cell may be a primary cultured cell, for example a primary human fibroblast or a keratinocyte, or may be an established cell line, such as NIH3T3, 293T or CHO among others. Further, a mammalian cell useful for expression of the constructs may be phenotypically normal or oncogenically transformed. It is assumed that one skilled in the art can readily establish and maintain a chosen host cell type in culture.

For large scale production of the protein, a unicellular organism, such as *E. coli, B. subtilis, S. cerevisiae*, an insect cell in combination with one or more baculovirus vectors, or a cell of a higher organism such as a vertebrate, e.g., COS 7, HEK 293, CHO, *Xenopus* oocyte, etc., may be used as the expression host cell. In some situations, it is desirable to express the construct in a eukaryotic cell, where the expressed protein will benefit from native folding and post-translational modifications. Small peptides may also be synthesized in the laboratory. Polypeptides that are subsets of the complete protein sequence may be used to identify and investigate parts of the protein important for function. Specific expression systems of interest include bacterial, yeast, insect cell, and mammalian cell derived expression systems such as those described in U.S. Pat. No. 6,969,597 and incorporated herein by reference.

When a host cell is used to replicate or express the polynucleotides or nucleic acids of the disclosure, the resulting replicated nucleic acid, RNA, expressed protein or polypeptide, is within the scope of the disclosure as a product of the host cell or organism. The product may be recovered by any appropriate means known in the art.

A bacterial host cell may be selected from phyla of Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, and Thermotogae. In some embodiments the host cell is a Firmicute selected from *Bacillus, Listeria, Staphylococcus*. In some embodiments the host cell is from Proteobacteria selected from *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio*, and *Xanthomonas*. In some embodiments the host cell is from Tenericutes selected from *Mycoplasma, Spiroplasma*, and *Ureaplasma*.

The present disclosure provides compositions and methods for introducing constructs or vectors into host cells. Constructs provided by the disclosure, including vectors, plasmids, and expression cassettes containing polynucleotides of the disclosure, may be introduced to selected host cells by any of a number of suitable methods known to those skilled in the art. Constructs may be inserted into mammalian host cells by methods including, but not limited to, electroporation, transfection, microinjection, micro-vessel transfer, particle bombardment, biolistic particle delivery, liposome mediated transfer and other methods described in Current Protocols in Cell Biology, Unit 20, pub. John Wiley & Sons, Inc., 2004 and incorporated herein by reference.

For example, for the introduction of a construct containing vectors into yeast or other fungal cells, chemical transformation methods are generally used (as described by Rose et al., 1990, Methods in Yeast Genetics, Cold Spring Harbor Laboratory Press, Cold Spring Harbor, N.Y. and incorporated herein by reference). For transformation of *S. cerevisiae*, for example, the cells are treated with lithium acetate. Transformed cells are then isolated on selective media appropriate to the selectable marker used.

Constructs may be introduced to appropriate bacterial cells by infection, as in the case of *E. coli* bacteriophage particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y., incorporated herein by reference), electroporation may also be used (Current Protocols in Molecular Biology, pub. John Wiley & Sons, Inc., 1993 and incorporated herein by reference).

The present disclosure provides compositions and methods for the introduction of vectors into host cells.

Methods for introducing a DNA sequence into eukaryotic cells are known in the art and typically include the use of a DNA vector or plasmid. There are many vectors known and available in the art that are useful for the polynucleotides of the disclosure. One of skill in the art will recognize that the selection of a particular vector depends upon the intended use of the polynucleotide. In one aspect, the DNA sequences are introduced by a vector or plasmid, capable of transforming and driving the expression of the components of the construct in the desired cell type, whether that cell type is prokaryotic or eukaryotic. Many vectors comprise sequences allowing both prokaryotic vector replication and eukaryotic expression of operably linked gene sequences.

Vectors useful according to the disclosure may be autonomously replicating, that is, the vector exists extrachromosomally, and its replication is not necessarily directly linked to the replication of the host genome. Alternatively, the replication of the vector may be linked to the replication of the host chromosomal DNA. For example, the vector may be integrated into a chromosome of the host cell as achieved by retroviral vectors.

A vector will comprise sequences operably linked to the coding sequence of the subject polypeptide that permit the transcription and translation of the components when appropriate. Within the expression vector, a subject polynucleotide is linked to a regulatory sequence as appropriate to obtain the desired expression properties. These regulatory sequences may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as environment specific promoters. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Numerous phage vectors are disclosed in Kieser et al. (*Practical Streptomyces Genetics*. 2000. John Innes Foundation. 613p). These vectors may include previously describe vectors like KC304 or, like KC304, may be a derivative of ΦC31 which contains a repressor gene (c) to establish and maintain lysogeny, a specific site (attP) in its DNA for integration into the host chromosome, cohesive ends to its DNA, deletion of inessential regions of DNA, one or more drug-selectable markers, comprise combinations of promoters, operators, ribosome binding sites, and signal sequences, and one or more restriction sites to facilitate cloning of a polynucleotide sequence encoding a transcription factor using ligation or other cloning techniques in the art.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as is known in the art.

A skilled artisan will recognize that the choice of vector for use with the disclosure is dependent on the host with which the disclosure will be utilized. Suitable vectors include, but are not limited to, bacteriophage-derived vectors, viral vectors, retroviral vectors, adenoviral vectors, adeno-associated viral vectors, herpes virus vectors, and insect vector systems. Such vectors are well known in the art.

Samples

The subject or biological source, from which a test biological sample may be obtained, may be a human or non-human animal, or a transgenic or cloned or tissue-engineered (including through the use of stem cells) organism. In certain preferred embodiments of the invention, the subject or biological source may be known to have, or may be suspected of having or being at risk for having, a circulating or solid tumor or other malignant condition, or an autoimmune disease, or an inflammatory condition, and in certain preferred embodiments of the invention the subject or biological source may be known to be free of a risk or presence of such disease.

Certain preferred embodiments contemplate a subject or biological source that is a human subject such as a patient that has been diagnosed as having or being at risk for developing or acquiring cancer according to art-accepted clinical diagnostic criteria, such as those of the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, New York); Pizzo and Poplack, *Principles and Practice of Pediatric Oncology* (Fourth edition, 2001, Lippincott, Williams and Wilkins, Philadelphia/ Ovid, New York); and Vogelstein and Kinzler, *The Genetic Basis of Human* Cancer (Second edition, 2002, McGraw Hill Professional, New York); certain embodiments contemplate a human subject that is known to be free of a risk for having, developing or acquiring cancer by such criteria.

Certain other embodiments contemplate a non-human subject or biological source, for example a non-human primate such as a macaque, chimpanzee, gorilla, vervet, orangutan, baboon or other non-human primate, including such non-human subjects that may be known to the art as preclinical models, including preclinical models for solid tumors and/or other cancers. Certain other embodiments contemplate a non-human subject that is a mammal, for example, a mouse, rat, rabbit, pig, sheep, horse, bovine, goat, gerbil, hamster, guinea pig or other mammal; many such mammals may be subjects that are known to the art as preclinical models for certain diseases or disorders, including circulating or solid tumors and/or other cancers (e.g., Talmadge et al., 2007 *Am. J. Pathol.* 170:793; Kerbel, 2003 *Canc. Biol. Therap.* 2(4 Suppl 1):S134; Man et al., 2007 *Canc. Met. Rev.* 26:737; Cespedes et al., 2006 *Clin. Transl. Oncol.* 8:318). The range of embodiments is not intended to be so limited, however, such that there are also contemplated other embodiments in which the subject or biological source may be a non-mammalian vertebrate, for example, another higher vertebrate, or an avian, amphibian or reptilian species, or another subject or biological source.

Biological samples may be provided by obtaining a blood sample, biopsy specimen, tissue explant, organ culture, biological fluid or any other tissue or cell preparation from a subject or a biological source. Preferably the sample comprises DNA or mRNA from lymphoid cells of the subject or biological source, which, by way of illustration and not limitation, may contain rearranged DNA at one or more BCR loci (or mRNA transcribed from one or more BCR loci). In certain embodiments a test biological sample may be obtained from a solid tissue (e.g., a solid tumor), for example by surgical resection, needle biopsy or other means for obtaining a test biological sample that contains a mixture of cells.

According to certain embodiments it may be desirable to isolate lymphoid cells (e.g., T cells and/or B cells) according to any of a large number of established methodologies, where isolated lymphoid cells are those that have been removed or separated from the tissue, environment or milieu in which they naturally occur. B cells and T cells can thus be obtained from a biological sample, such as from a variety of tissue and biological fluid samples including bone marrow, thymus, lymph glands, lymph nodes, peripheral tissues and blood, but peripheral blood is most easily accessed. Any peripheral tissue can be sampled for the presence of B and T cells and is therefore contemplated for use in the methods described herein. Tissues and biological fluids from which adaptive immune cells, may be obtained include, but are not limited to skin, epithelial tissues, colon, spleen, a mucosal secretion, oral mucosa, intestinal mucosa, vaginal mucosa or a vaginal secretion, cervical tissue, ganglia, saliva, cerebrospinal fluid (CSF), bone marrow, cord blood, serum, serosal fluid, plasma, lymph, urine, ascites fluid, pleural fluid, pericardial fluid, peritoneal fluid, abdominal fluid, culture medium, conditioned culture medium or lavage fluid. In certain embodiments, adaptive immune cells may be isolated from an apheresis sample. Peripheral blood samples may be obtained by phlebotomy from subjects. Peripheral blood mononuclear cells (PBMC) are isolated by techniques known to those of skill in the art, e.g., by Ficoll-Hypaque® density gradient separation. In certain embodiments, whole PBMCs are used for analysis.

For nucleic acid extraction, total genomic DNA may be extracted from cells using methods known in the art and/or commercially available kits, e.g., by using the QIAamp® DNA blood Mini Kit (QIAGEN®). The approximate mass of a single haploid genome is 3 pg. Preferably, at least 100,000 to 200,000 cells are used for analysis, i.e., about 0.6 to 1.2 µg DNA from diploid B cells. Using PBMCs as a source, the number of B cells can be estimated to be about 30% of total cells. The number of B cells can also be estimated to be about 30% of total cells in a PBMC preparation.

In some embodiments, a plurality of B-cells are isolated, wherein said plurality comprises at least $10^2$, $10^3$, $10^4$, $10^5$, $10^6$, $10^7$, $10^8$, or $10^9$ B-cells. In some embodiments, said plurality of isolated B-cells comprises at least $10^2$-$10^3$, $10^2$-$10^4$, $10^2$-$10^5$, $10^2$-$10^6$, $10^2$-$10^7$, $10^2$-$10^8$, $10^2$-$10^9$, $10^3$-$10^4$, $10^3$-$10^5$, $10^3$-$10^6$, $10^3$-$10^7$, $10^3$-$10^8$, $10^3$-$10^9$, $10^4$-$10^5$, $10^4$-$10^6$, $10^4$-$10^7$, $10^4$-$10^8$, $10^4$-$10^9$, $10^5$-$10^6$, $10^5$-$10^7$, $10^5$-$10^8$, $10^5$-$10^9$, $10^6$-$10^7$, $10^6$-$10^8$, $10^6$-$10^9$, $10^7$-$10^8$, $10^7$-$10^9$, or $10^8$-$10^9$ B-cells. In some embodiments, the B-cell receptors are extracellular, and in further embodiments the B-cell receptors are intracellular.

The BCR gene loci contain many different variable (V), diversity (D), and joining (J) gene segments, which are subjected to rearrangement processes during early lymphoid differentiation. BCR V, D and J gene segment sequences are known in the art and are available in public databases such as GENBANK. The V-D-J rearrangements are mediated via a recombinase enzyme complex in which the RAG1 and RAG2 proteins play a key role by recognizing and cutting the DNA at the recombination signal sequences (RSS), which are located downstream of the V gene segments, at both sides of the D gene segments, and upstream of the J gene segments. Inappropriate RSS reduce or even completely prevent rearrangement. The recombination signal sequence (RSS) consists of two conserved sequences (heptamer, 5'-CACAGTG-3', and nonamer, 5'-ACAAAAACC-3'), separated by a spacer of either 12+/−1 bp ("12-signal") or 23+/−1 bp ("23-signal").

A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et al., 1994 *Nucl. Ac. Res.* 22:1785; Akamatsu et al., 1994 *J. Immunol.* 153:4520; Hesse et al., 1989 *Genes Dev.* 3:1053). Mutations of other nucleotides have minimal or inconsistent effects. The spacer, although more variable, also has an impact on recombination, and single-nucleotide replacements have been shown to significantly impact recombination efficiency (Fanning et al., 1996 *Cell. Immunol. Immunopath.* 79:1, Larijani et al., 1999 *Nucl. Ac. Res.* 27:2304; Nadel et al., 1998 *J. Immunol.* 161:6068; Nadel et al., 1998 *J. Exp. Med.* 187:1495). Criteria have been described for identifying RSS polynucleotide sequences having significantly different recombination efficiencies (Ramsden et al., 1994 *Nucl. Ac. Res.* 22:1785; Akamatsu et al. 1994 *J. Immunol.* 153:4520; Hesse et al. 1989 *Genes Dev.* 3:1053, and Lee et al., 2003 *PLoS* 1(1):E1).

The rearrangement process generally starts with a D to J rearrangement followed by a V to D-J rearrangement in the case of IG heavy chain (IGH) genes or concerns direct V to J rearrangements in case of IG kappa (IGK), or IG lambda (IGL) genes. The sequences between rearranging gene segments are generally deleted in the form of a circular excision product, also called B cell receptor excision circle (BREC).

The many different combinations of V, D, and J gene segments represent the so-called combinatorial repertoire, which is estimated to be ~$2\times10^6$ for Ig molecules. At the junction sites of the V, D, and J gene segments, deletion and random insertion of nucleotides occurs during the rearrangement process, resulting in highly diverse junctional regions, which significantly contribute to the total repertoire of Ig molecules, estimated to be >$10^{12}$.

Mature B-lymphocytes further extend their Ig repertoire upon antigen recognition in follicle centers via somatic hypermutation, a process, leading to affinity maturation of the Ig molecules. The somatic hypermutation process focuses on the V- (D-) J exon of IGH and IG light chain genes and concerns single nucleotide mutations and sometimes also insertions or deletions of nucleotides. Somatically-mutated IG genes are also found in mature B-cell malignancies of follicular or post-follicular origin.

In certain embodiments described herein, V-segment and J-segment primers may be employed in a PCR reaction to amplify rearranged BCR CDR3-encoding DNA regions in a test biological sample, wherein each functional Ig V-encoding gene segment comprises a V gene recombination signal sequence (RSS) and each functional Ig J-encoding gene segment comprises a J gene RSS. In these and related embodiments, each amplified rearranged DNA molecule may comprise (i) at least about 10, 20, 30, 40, 50, 60, 70, 80, 90, 100, 200, 300, 400, 500, 600, 700, 800, 900, 1000 (including all integer values therebetween) or more contiguous nucleotides of a sense strand of the Ig V-encoding gene segment, with the at least about 10, 20, 30, 40, 50, 60, 70, 80, 90, 100, 200, 300, 400, 500, 600, 700, 800, 900, 1000 or more contiguous nucleotides being situated 5' to the V gene RSS and/or each amplified rearranged DNA molecule may comprise (ii) at least about 10, 20, 30, 40, 50, 60, 70, 80, 90, 100, 200, 300, 400, 500 (including all integer values therebetween) or more contiguous nucleotides of a sense strand of the Ig J-encoding gene segment, with the at least about 10, 20, 30, 40, 50, 60, 70, 80, 90, 100, 200, 300, 400, 500 or more contiguous nucleotides being situated 3' to the J gene RSS.

In some embodiments, the present invention will employ, unless indicated specifically to the contrary, conventional methods in microbiology, molecular biology, biochemistry, molecular genetics, cell biology, virology and immunology techniques that are within the skill of the art, and reference to several of which is made below for the purpose of illustration. Such techniques are explained fully in the literature. See, e.g., Sambrook, et al., *Molecular Cloning: A Laboratory Manual* (3$^{rd}$ Edition, 2001); Sambrook, et al., *Molecular Cloning: A Laboratory Manual* (2$^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Antigen Display Library

In some embodiments, antigen display libraries are used to present potential antigenic epitopes to BCRs in a method for identifying antigen-specific BCR sequences. In some embodiments, antigenic epitopes, also known as antigenic determinants, is the portion of an antigen that is recognized by components of the immune system, e.g., antibodies, B-cells, T-cells, etc. In some embodiments, an antigen is any structural substance that serves as a target for receptors of an adaptive immune response, such as BCRs.

In some embodiments, antigen display libraries comprise whole antigens or fragments thereof. In some embodiments, the antigens or fragments thereof may be selected from bacteria, viruses, fungi, protists, plants, vertebrates, mammals, fish, or any combination thereof. In some embodiments, the antigens may be from pathogens or cancerous cells. In some embodiments, the displayed antigen is 9, 10, 11, 12 or more amino acids in length. Preferably the displayed antigen is 9-12 amino acids in length.

In some embodiments, antigen display libraries are selected from phage display libraries, yeast display libraries, bacterial display libraries, and eukaryotic virus display libraries.

Antigen display methodologies have proven invaluable for the discovery, production, and optimization of proteins and peptides in a variety of biotechnological applications. Various approaches including phage display (Smith, G. P. (1985) *Science*, 228, 1315-1317), mRNA (Wilson et al. (2001)*Proc. Natl. Acad. Sci. USA*, 98, 3750-3755) and DNA display (Yonezawa et al. (2003) *Nucleic Acids Res.*, 31, e118), ribosome display (Hanes, J. & Pluckthun, A. (1997) *Proc. Natl. Acad. Sci. USA*, 94, 4937-42), eukaryotic virus display (Bupp, K. & Roth, M. J. (2002) *Mol. Ther.*, 5, 329-335; Muller et al. (2003) *Nat. Biotechnol.*, 21:1040-1046), yeast display (Boder, E. T. & Wittrup, K. D. (1997) *Nat. Biotechnol.*, 15, 553-557), and bacterial display (Lu et al. (1995) *Biotechnology* (N Y), 13, 366-372) have been developed to screen diverse molecular repertoires. In particular, bacterial display libraries have enabled antibody affinity maturation (Daugherty et al. (2000) *Proc. Natl. Acad. Sci. USA*, 97, 2029-2034), the discovery of protein binding peptides (Bessette et al. (2004) *Protein Eng. Des. Sel.*, 17, 731-739), cell-specific ligands (Dane et al. (2006)*J. Immunol. Methods*, 309, 120-129; Nakajima et al. (2000) *Gene*, 260, 121-131), and the identification of optimal protease substrates (Boulware, K. T. & Daugherty, P. S. (2006) *Proc. Natl. Acad. Sci. USA*, 103, 7583-7588).

In one embodiment, phage display libraries are utilized. Phage display libraries may be constructed on the surface of phages, e.g. a bacteriophage such as fd (McCafferty et al, 1990, Nature, 348, 552-554) or M13 (Barbas III et al, 1991, PNAS, 8ji, 7978-7982). Phage display libraries are constructed following essentially the same principles as antibody libraries, e.g. peptide libraries on the surface of bacteriophage (Smith, 1985, Science, 228, 1315-1317).

In some embodiments of this disclosure, phage for use within the scope of this disclosure include, but are not limited to, A11, R4, A118, C31, C62, C43, AE2, Acm7, BL8, BL9, BK5, Bf42, BN1, BT11, ΦBT1, C2121, Chp1, CTXΦ, D37, DAV1, Deβ, EΦB, EΦ-y, EC1, Erh1, FP1, Min1, Plot, SV1, TG1, R4, TJE1, TPA2, PhiSAV, p1.1, B22, P105, PhiAsp2, ArV2, ArV1, GTE2, GTES. GRU1, TA17A, T7, T3, T4, DD5, PAD20, PA6, K29, P58, PM4, PYO6, RP10, Qβ, SAV1, SD1, SP1, SST, SsV, Tm10, Tull*, V40, λ, ΦXo, ΦC31, ΨM1, SV1, ΦC44, Ω8, M13, fd, f1, or variants thereof.

In one embodiment, bacterial surface display libraries are utilized. One of the key advantages of bacterial surface display is the ability to use flow cytometry for quantitative screening of the libraries, allowing for real-time analysis of binding affinity and specificity to optimize the screening process (Wittrup, K. D. (2001) *Curr. Opin. Biotechnol.*, 12, 395-399). Additionally, the ease of genetic manipulation, high transformation efficiency, and rapid growth rate make *E. coli* a well-suited host for display. A broad range of bacterial surface display systems have been developed allowing for insertional or terminally fused peptides and proteins to be displayed on the cell surface.

Expression of antigens on the surface of bacteria has been demonstrated by fusions to LamB (Charbit et al, 1988, Gene, 7_0, 181-189 and Bradbury et al, 1993, Bio/Technology, 1565-1568), Omp A (Pistor and Hobom, 1989, Klin. Wochenschr., £6, 110-116), fimbriae (Hedegaard and Klemm, 1989, Gene, J35, 115-124 and Hofnung, 1991, Methods Cell Biol., 34, 77-105), IgA protease β domain (Klauser et al, 1990, EMBO J., 9, 1991-1999) and flagellae (Newton et al, 1989, Science, 244, 70-72).

In one embodiment, cell display combinatorial libraries are disclosed, for example, U.S. Pat. No. 6,214,613 to K. Higuchi et al. "Expression Screening Vector". For example, the display of proteins on cell surfaces can provide a support, similar to the immobilization of a protein on, for example, sepharose. Rather than covalently link a soluble protein to an inert support matrix, an expressed protein can be displayed on a cell surface. Hence, cell surface display can be used to circumvent separate expression, purification, and immobilization of binding proteins and enzymes. In addition, the biomolecules can be secreted from the cell rather than displayed on the surface.

In one embodiment, eukaryotic cell display libraries can be used in the practice of the present invention, wherein the library comprises a plurality of expressed biomolecules. Eukaryotic cell display libraries include, for example, yeast, insect, plant, and mammalian libraries. Cells can be in a cell line or can be a primary culture cell type.

Methods of modifying mammalian cells for surface display are known including cell surface display procedures. See, for example, U.S. Pat. No. 6,255,071 to Beach et al. (Jul. 3, 2001); U.S. Pat. No. 6,207,371 to Zambrowicz et al. (Mar. 27, 2001); and U.S. Pat. No. 6,136,566 to Sands et al. (Oct. 24, 2000). See also, for example, Holmes et al., *J. Immunol. Methods,* 1999, 230: 141-147; Chesnut et al. *J. Immunol. Methods,* 1996, 193: 17-27; Chou et al., *Biotechnol Bioeng,* 1999, 65: 160-169.

In one embodiment, yeast surface display libraries are utilized. Yeast surface display libraries and the methods of creating said libraries are described in, for example, U.S. Pat. No. 6,300,065 to Kieke et al. (Oct. 9, 2001); U.S. Pat. No. 6,331,391 to Wittrup et al. (Dec. 18, 2001); U.S. Pat. Nos. 6,423,538 and 6,300,065.

Yeast surface display libraries are further presented in Bhatia et al., *Biotechnol Prog.* Jun. 6, 2003; 19(3):1033-1037; and Feldhaus et al., *Nat Biotechnol.* February 2003; 21(2):163-70.

Primers and Amplification

The nucleic acids of the present embodiments, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an immunoglobulin or a region thereof (e.g., a V region, a D segment, a J region, a C region, etc.) for use according to the present embodiments may be identical to the coding sequence known in the art for any given immunoglobulin gene regions or polypeptide domains (e.g., V-region domains, CDR3 domains, etc.), or may be a different coding sequence, which, as a result of the redundancy or degeneracy of the genetic code, encodes the same immunoglobulin region or polypeptide.

In some embodiments, oligonucleotide primers are provided in an oligonucleotide primer set that comprises a plurality of V-segment primers and a plurality of J-segment primers, where the primer set is capable of amplifying rearranged DNA encoding adaptive immune receptors in a biological sample that comprises lymphoid cell DNA. Suitable primer sets are known in the art and disclosed herein.

In certain embodiments the primer set is designed to include a plurality of V sequence-specific primers that includes, for each unique V region gene (including pseudogenes) in a sample, at least one primer that can specifically anneal to a unique V region sequence; and for each unique J region gene in the sample, at least one primer that can specifically anneal to a unique J region sequence.

Primer design may be achieved by routine methodologies in view of known BCR genomic sequences. Accordingly, the primer set is preferably capable of amplifying every possible V-J combination that may result from DNA rearrangements in the BCR locus. As also described below, certain embodiments contemplate primer sets in which one or more V primers may be capable of specifically annealing to a unique sequence that may be shared by two or more V regions but that is not common to all V regions, and/or in which one or more J primers may be capable of specifically annealing to a unique sequence that may be shared by two or more J regions but that is not common to all J regions, and/or in which one or more C primers may be capable of specifically annealing to a unique sequence that may be shared by two or more C regions but that is not common to all C regions.

In particular embodiments, oligonucleotide primers for use in the compositions and methods described herein may comprise or consist of a nucleic acid of at least about 15 nucleotides long that has the same sequence as, or is complementary to, a 15 nucleotide long contiguous sequence of the target V-, C-, or J-segment (i.e., portion of genomic polynucleotide encoding a V-region, C-region, or J-region polypeptide). Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, or 50, nucleotides long that have the same sequence as, or sequence complementary to, a contiguous sequence of the target V-, C-, or J-region encoding polynucleotide segment, will also be of use in certain embodiments. All intermediate lengths of the presently described oligonucleotide primers are contemplated for use herein. As would be recognized by the skilled person, the primers may have additional sequence added (e.g., nucleotides that may not be the same as or complementary to the target V-, or C-, or J-region encoding polynucleotide segment), such as restriction enzyme recognition sites, adaptor sequences for sequencing, barcode sequences, and the like (see e.g., primer sequences provided in the Tables). Therefore, the length of the primers may be longer, such as about 55, 56, 57, 58, 59, 60, 61, 62, 63, 64, 65, 66, 67, 68, 69, 70, 71, 72, 73, 74, 75, 80, 85, 90, 95, 100 or more nucleotides in length or more, depending on the specific use or need.

Also contemplated for use in certain embodiments are adaptive immune receptor V-segment, C-segment, or J-segment oligonucleotide primer variants that may share a high degree of sequence identity to the oligonucleotide primers for which nucleotide sequences are presented herein. Thus, in these and related embodiments, adaptive immune receptor V-segment, C-segment, or J-segment oligonucleotide primer variants may have substantial identity to the adaptive immune receptor V-segment, C-segment, or J-segment oligonucleotide primer sequences disclosed herein, for example, such oligonucleotide primer variants may comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like.

Typically, oligonucleotide primer variants will contain one or more substitutions, additions, deletions and/or insertions, preferably such that the annealing ability of the variant oligonucleotide is not substantially diminished relative to that of an adaptive immune receptor V-segment or J-segment oligonucleotide primer sequence that is specifically set forth herein.

In certain preferred embodiments, the V-segment, C-segment, and J-segment oligonucleotide primers as described herein are designed to include nucleotide sequences such that adequate information is present within the sequence of an amplification product of a rearranged adaptive immune receptor (e.g., BCR) gene to identify uniquely the specific V, specific C, and the specific J genes that give rise to the amplification product in the rearranged adaptive immune receptor locus (e.g., at least 1, 2, 3, 4, 5, 6, 7, 8, 9, 10, 11, 12, 13, 14, 15, 16, 17, 18, 19 or 20 base pairs of sequence upstream of the V gene recombination signal sequence (RSS), preferably at least about 22, 24, 26, 28, 30, 32, 34, 35, 36, 37, 38, 39 or 40 base pairs of sequence upstream of the V gene recombination signal sequence (RSS), and in certain preferred embodiments greater than 40 base pairs of sequence upstream of the V gene recombination signal sequence (RSS); and at least 1, 2, 3, 4, 5, 6, 7, 8, 9, 10, 11, 12, 13, 14, 15, 16, 17, 18, 19 or 20 base pairs downstream of the J gene RSS, preferably at least about 22, 24, 26, 28 or 30 base pairs downstream of the J gene RSS, and in certain preferred embodiments greater than 30 base pairs downstream of the J gene RSS); and at least 1, 2, 3, 4, 5, 6, 7, 8, 9, 10, 11, 12, 13, 14, 15, 16, 17, 18, 19 or 20 base pairs downstream or upstream of the C gene RSS, preferably at least about 22, 24, 26, 28 or 30 base pairs downstream or upstream of the C gene RSS, and in certain preferred embodiments greater than 30 base pairs downstream or upstream of the C gene RSS).

This feature stands in contrast to oligonucleotide primers described in the art for amplification of Ig-encoding gene sequences, which rely primarily on the amplification reaction merely for detection of presence or absence of products of appropriate sizes for V, C, and J segments (e.g., the presence in PCR reaction products of an amplicon of a particular size indicates presence of a V, C, or J segment but fails to provide the sequence of the amplified PCR product and hence fails to confirm its identity, such as the common practice of spectratyping).

Oligonucleotides (e.g., primers) can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Lett.* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference. IG primers and methods of using said primers are described in U.S. Patent Application Publication Nos. US 2012-0058902 and US 2010-0330571, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature.

A primer is preferably a single-stranded DNA. The appropriate length of a primer depends on the intended use of the primer but typically ranges from 6 to 50 nucleotides, or in certain embodiments, from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

As described herein, primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning, detection, or sequencing of the amplified product. The region of the primer which is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites.

In some embodiments, primers for use in amplifying the phage-containing nucleic acid sequence encoding the antigen hybridize to one or more synthetic polynucleotide sequences flanking said nucleic acid sequence encoding the antigen.

In particular embodiments, primers for use in the methods described herein comprise or consist of a nucleic acid of at least about 15 nucleotides long that has the same sequence as, or is complementary to, a 15 nucleotide long contiguous sequence of the target V, C, or J segment. Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, or 50, nucleotides long that have the same sequence as, or sequence complementary to, a contiguous sequence of the target V, C, or J segment, will also be of use in certain embodiments. All intermediate lengths of the aforementioned primers are contemplated for use herein. As would be recognized by the skilled person, the primers may have additional sequence added (e.g., nucleotides that may not be the same as or complementary to the target V, C, or J segment), such as restriction enzyme recognition sites, adaptor sequences for sequencing, barcode sequences, and the like (see e.g., primer sequences provided herein). Therefore, the length of the primers may be longer, such as 55, 56, 57, 58, 59, 60, 65, 70, 75, nucleotides in length or more, depending on the specific use or need. For example, in one embodiment, the forward and reverse primers are both modified at the 5' end with the universal forward primer sequence compatible with a DNA sequencer.

Also contemplated for use in certain embodiments are adaptive immune receptor V-segment, C-segment, or J-segment oligonucleotide primer variants that may share a high degree of sequence identity to the oligonucleotide primers for which nucleotide sequences are presented herein. Thus, in these and related embodiments, adaptive immune receptor V-segment, C-segment, or J-segment oligonucleotide primer variants may have substantial identity to the adaptive immune receptor V-segment, C-segment, or J-segment oligonucleotide primer sequences disclosed herein, for example, such oligonucleotide primer variants may comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like.

Typically, oligonucleotide primer variants will contain one or more substitutions, additions, deletions and/or insertions, preferably such that the annealing ability of the variant oligonucleotide is not substantially diminished relative to that of an adaptive immune receptor V-segment, C-segment, or J-segment oligonucleotide primer sequence that is specifically set forth herein. As also noted elsewhere herein, in preferred embodiments adaptive immune receptor V-segment, C-segment, and J-segment oligonucleotide primers are designed to be capable of amplifying a rearranged BCR sequence that includes the coding region for CDR3.

In some embodiments, the primers for use in the multiplex PCR methods of the present disclosure may be functionally blocked to prevent non-specific priming of non-T or B cell sequences. For example, the primers may be blocked with chemical modifications as described in U.S. Patent Application Publication No. US 2010-0167353. According to certain herein disclosed embodiments, the use of such blocked primers in the present multiplex PCR reactions involves primers that may have an inactive configuration wherein DNA replication (i.e., primer extension) is blocked, and an activated configuration wherein DNA replication proceeds. The inactive configuration of the primer is present when the primer is either single-stranded, or when the primer is specifically hybridized to the target DNA sequence of interest but primer extension remains blocked by a chemical moiety that is linked at or near to the 3' end of the primer.

The activated configuration of the primer is present when the primer is hybridized to the target nucleic acid sequence of interest and is subsequently acted upon by RNase H or another cleaving agent to remove the 3' blocking group, thereby allowing an enzyme (e.g., a DNA polymerase) to catalyze primer extension in an amplification reaction. Without wishing to be bound by theory, it is believed that the kinetics of the hybridization of such primers are akin to a second order reaction, and are therefore a function of the B cell gene sequence concentration in the mixture. Blocked primers minimize non-specific reactions by requiring hybridization to the target followed by cleavage before primer extension can proceed. If a primer hybridizes incorrectly to a sequence that is related to the desired target sequence but which differs by having one or more non-complementary nucleotides that result in base-pairing mismatches, cleavage of the primer is inhibited, especially when there is a mismatch that lies at or near the cleavage site. This strategy to improve the fidelity of amplification reduces the frequency of false priming at such locations, and thereby increases the specificity of the reaction. As would be recognized by the skilled person, reaction conditions, particularly the concentration of RNase H and the time allowed for hybridization and extension in each cycle, can be optimized to maximize the difference in cleavage efficiencies between highly efficient cleavage of the primer when it is correctly hybridized to its true target sequence, and poor cleavage of the primer when there is a mismatch between the primer and the template sequence to which it may be incompletely annealed.

As described in U.S. Patent Application Publication No. US 2010-0167353, a number of blocking groups are known in the art that can be placed at or near the 3' end of the oligonucleotide (e.g., a primer) to prevent extension. A primer or other oligonucleotide may be modified at the 3'-terminal nucleotide to prevent or inhibit initiation of DNA synthesis by, for example, the addition of a 3' deoxyribonucleotide residue (e.g., cordycepin), a 2',3'-dideoxyribonucleotide residue, non-nucleotide linkages or alkane-diol modifications (U.S. Pat. No. 5,554,516). Alkane diol modifications which can be used to inhibit or block primer extension have also been described by Wilk et al., (1990 Nucleic Acids Res. 18 (8):2065), and by Arnold et al. (U.S. Pat. No. 6,031,091). Additional examples of suitable blocking groups include 3' hydroxyl substitutions (e.g., 3'-phosphate, 3'-triphosphate or 3'-phosphate diesters with alcohols such as 3-hydroxypropyl), 2'3'-cyclic phosphate, 2' hydroxyl substitutions of a terminal RNA base (e.g., phosphate or sterically bulky groups such as triisopropyl silyl (TIPS) or tert-butyl dimethyl silyl (TBDMS)). 2'-alkyl silyl groups such as TIPS and TBDMS substituted at the 3'-end of an oligonucleotide are described by Laikhter et al., U.S. Patent Application Publication No. US 2007-0218490, which is incorporated herein by reference. Bulky substituents can also be incorporated on the base of the 3'-terminal residue of the oligonucleotide to block primer extension.

In some embodiments, the oligonucleotide may comprise a cleavage domain that is located upstream (e.g., 5' to) of the blocking group used to inhibit primer extension. As examples, the cleavage domain may be an RNase H cleavage domain, or the cleavage domain may be an RNase H2 cleavage domain comprising a single RNA residue, or the oligonucleotide may comprise replacement of the RNA base with one or more alternative nucleosides. Additional illustrative cleavage domains are described in U.S. Patent Application Publication No. US 2010-0167353.

In one embodiment, a multiplex PCR system may use 40, 45, 50, 55, 60, 65, 70, 75, 80, 85, or more forward primers, wherein each forward primer is complementary to a single functional BCR V segment or a small family of functional BCR V segments; and, for example, thirteen reverse primers, each specific to a BCR J segment. In another embodiment, a multiplex PCR reaction may use four forward primers each specific to one or more functional BCR V segments and four reverse primers each specific for one or more BCR J segments. In another embodiment, a multiplex PCR reaction may use 84 forward primers each specific to one or more functional V segments and six reverse primers each specific for one or more J segments.

Thermal cycling conditions may follow methods of those skilled in the art. For example, using a PCR Express™ thermal cycler (Hybaid, Ashford, UK), the following cycling conditions may be used: 1 cycle at 95° C. for 15 minutes, 25 to 40 cycles at 94° C. for 30 seconds, 59° C. for 30 seconds and 72° C. for 1 minute, followed by one cycle at 72° C. for 10 minutes. As will be recognized by the skilled person, thermal cycling conditions may be optimized, for example, by modifying annealing temperatures, annealing times, number of cycles and extension times. As would be recognized by the skilled person, the amount of primer and other PCR reagents used, as well as PCR parameters (e.g., annealing temperature, extension times and cycle numbers), may be optimized to achieve desired PCR amplification efficiency.

Alternatively, in certain related embodiments also contemplated herein, "digital PCR" methods can be used to quantitate the number of target genomes in a sample, without the need for a standard curve. In digital PCR, the PCR reaction for a single sample is performed in a multitude of more than 100 microcells or droplets, such that each droplet either amplifies (e.g., generation of an amplification product provides evidence of the presence of at least one template molecule in the microcell or droplet) or fails to amplify (evidence that the template was not present in a given microcell or droplet). By simply counting the number of positive microcells, it is possible directly to count the number of target genomes that are present in an input sample. Digital PCR methods typically use an endpoint readout, rather than a conventional quantitative PCR signal that is measured after each cycle in the thermal cycling reaction (see, e.g., Pekin et al., 2011 *Lab. Chip* 11(13):2156; Zhong et al., 2011 *Lab. Chip* 11(13):2167; Tewhey et al., 2009 *Nature Biotechnol.* 27:1025; 2010 *Nature Biotechnol.* 28:178). Accordingly, any of the herein described compositions (e.g., adaptive immune receptor gene-specific oligonucleotide primer sets) and methods may be adapted for use in such digital PCR methodology, for example, the ABI QuantStudio™ 12K Flex System (Life Technologies, Carlsbad, Calif.), the QuantaLife™ digital PCR system (BioRad, Hercules, Calif.) or the RainDance™ microdroplet digital PCR system (RainDance Technologies, Lexington, Mass.).

Synthetic Polynucleotides

In one embodiment, synthetic polynucleotides may comprise at least a barcode sequence, an adaptor sequence, and a sequencing platform tag sequence. In some embodiments, the synthetic polynucleotides comprise at least one barcode sequence, at least one adaptor sequence, and at least one sequencing platform tag sequence. In some embodiments, the synthetic polynucleotides flank nucleotide sequences that encode the antigens or epitopes of the antigen display library.

In one embodiment, the synthetic polynucleotide sequences comprise primer hybridization sites that allow for the amplification of the entire nucleic acid sequence encoding the antigen.

Adaptors

The herein described oligonucleotides may in certain embodiments comprise first (U1) and second (U2) (and optionally third (U3) and fourth (U4)) universal adaptor oligonucleotide sequences, or may lack either or both of U1 and U2 (or U3 or U4). A universal adaptor oligonucleotide U thus may comprise either nothing or an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence, and U2 may comprise either nothing or an oligonucleotide having a sequence that is selected from (i) a second universal adaptor oligonucleotide sequence, and (ii) a second sequencing platform-specific oligonucleotide sequence that is linked to and positioned 5' to a second universal adaptor oligonucleotide sequence. A similar relationship pertains for U3 and U4.

U1 and/or U2 may, for example, comprise universal adaptor oligonucleotide sequences and/or sequencing platform-specific oligonucleotide sequences that are specific to a single-molecule sequencing technology being employed, for example the HiSeq™ or GeneAnalyzer™-2 (GA-2) systems (Illumina, Inc., San Diego, Calif.) or another suitable sequencing suite of instrumentation, reagents and software. Inclusion of such platform-specific adaptor sequences permits direct quantitative sequencing of the presently described dsDNA amplification products into which U has been incorporated as described herein, using a nucleotide sequencing methodology such as the HiSeq™ or GA2 or equivalent. This feature therefore advantageously permits qualitative and quantitative characterization of the dsDNA composition.

For example, dsDNA amplification products may be generated that have universal adaptor sequences at both ends, so that the adaptor sequences can be used to further incorporate sequencing platform-specific oligonucleotides at each end of each template.

Without wishing to be bound by theory, platform-specific oligonucleotides may be added onto the ends of such dsDNA using 5' (5'-platform sequence-universal adaptor-1 sequence-3') and 3' (5'-platform sequence-universal adaptor-2 sequence-3') oligonucleotides in three cycles of denaturation, annealing and extension, so that the relative representation in the dsDNA composition of each of the component dsDNAs is not quantitatively altered. Unique identifier sequences (e.g., barcode sequences B that are associated with and thus identify individual V and/or J regions, or sample-identifier barcodes as described herein) are placed adjacent to the adaptor sequences, thus permitting quantitative sequencing in short sequence reads, in order to characterize the DNA population by the criterion of the relative amount of each unique sequence that is present.

Non-limiting examples of additional adaptor sequences are shown in Table 1 and set forth in SEQ ID NOs: 1-22.

TABLE 1

Exemplary Adaptor Sequences

| Adaptor (primer) name | Sequence | SEQ ID NO: |
|---|---|---|
| T7 Promotor | AATACGACTCACTATAGG | 1 |
| T7 Terminator | GCTAGTTATTGCTCAGCGG | 2 |
| T3 | ATTACCCTCAACTAAAGG | 3 |
| SP6 | GATTTAGGTGACACTATAG | 4 |
| M13F(-21) | TGTAAAACGACGGCCAGT | 5 |
| M13F(-40) | GTTTTCCCAGTCACGAC | 6 |
| M13R Reverse | CAGGAAACAGCTATGACC | 7 |
| AOX1 Forward | GACTGGTTCCAATTGACAGC | 8 |
| AOX1 Reverse | GCAAATGGCATTCTGACATCC | 9 |
| pGEX Forward (GST 5, pGEX 5') | GGGCTGGCAGCCACGTTTGGTG | 10 |
| pGEX Reverse (GST 3, pGEX 3') | CCGGGAGCTGCATGTGTCAGAGG | 11 |
| BGH Reverse | AACTAGAAGGCACAGTCGAGGC | 12 |
| GFP (C' terminal, CFP, YFP or BFP) | CACTCTCGGCATGGACGAGC | 13 |

TABLE 1-continued

Exemplary Adaptor Sequences

| Adaptor (primer) name | Sequence | SEQ ID NO: |
|---|---|---|
| GFP Reverse | TGGTGCAGATGAACTTCAGG | 14 |
| GAG | GTTCGACCCCGCCTCGATCC | 15 |
| GAG Reverse | TGACACACATTCCACAGGGTC | 16 |
| CYC1 Reverse | GCGTGAATGTAAGCGTGAC | 17 |
| pFastBacF* | 5'-d(GGATTATTCATACCGTCCCA)-3' | 18 |
| pFastBacR* | 5'-d(CAAATGTGGTATGGCTGATT)-3' | 19 |
| pBAD Forward* | 5'-d(ATGCCATAGCATTTTTATCC)-3' | 20 |
| pBAD Reverse* | 5'-d(GATTTATCTGTATCAGG)-3' | 21 |
| CMV-Forward* | 5'-d(CGCAAATGGGCGGTAGGCGTG)-3' | 72 |

*d = deoxy

Barcodes

As described herein, certain embodiments contemplate designing oligonucleotide sequences to contain short signature sequences that permit unambiguous identification of the polynucleotide sequence into which they are incorporated, and hence of at least one primer responsible for amplifying that product, without having to sequence the entire amplification product. In the herein described oligonucleotides, such barcodes B (e.g., B1, B2) are each either nothing or each comprise an oligonucleotide B that comprises an oligonucleotide barcode sequence of 3, 4, 5, 6, 7, 8, 9, 10, 11, 12, 13, 14, 15, 16, 17, 18, 19, 20, 25, 30, 35, 40, 45, 50 or more contiguous nucleotides (including all integer values therebetween), wherein in each of the plurality of oligonucleotide sequences B comprises a unique oligonucleotide sequence which uniquely identifies a particular V and/or J oligonucleotide primer sequence.

Exemplary barcodes may comprise a first barcode oligonucleotide of 5, 6, 7, 8, 9, 10, 11, 12, 13, 14, 15 or 16 nucleotides that uniquely identifies each oligonucleotide primer (e.g., a V or a J primer) in the primer composition, and optionally in certain embodiments a second barcode oligonucleotide of 5, 6, 7, 8, 9, 10, 11, 12, 13, 14, 15 or 16 nucleotides that uniquely identifies each partner primer in a primer set (e.g., a J or a V primer), to provide barcodes of, respectively, 5, 6, 7, 8, 9, 10, 11, 12, 13, 14, 15, 16, 17, 18, 19, 20, 21, 22, 23, 24, 25, 26, 27, 28, 29, 30, 31 or 32 nucleotides in length, but these and related embodiments are not intended to be so limited. Barcode oligonucleotides may comprise oligonucleotide sequences of any length, so long as a minimum barcode length is obtained that precludes occurrence of a given barcode sequence in two or more product polynucleotides having otherwise distinct sequences (e.g., V and J sequences).

Thus, the minimum barcode length, to avoid such redundancy amongst the barcodes that are used to uniquely identify different V-J sequence pairings, is X nucleotides, where $4^x$ is greater than the number of distinct template species that are to be differentiated on the basis of having non-identical sequences. In practice, barcode oligonucleotide sequence read lengths may be limited only by the sequence read-length limits of the nucleotide sequencing instrument to be employed. For certain embodiments, different barcode oligonucleotides that will distinguish individual species of template oligonucleotides should have at least two nucleotide mismatches (e.g., a minimum hamming distance of 2) when aligned to maximize the number of nucleotides that match at particular positions in the barcode oligonucleotide sequences.

The skilled artisan will be familiar with the design, synthesis, and incorporation into a larger oligonucleotide or polynucleotide construct, of oligonucleotide barcode sequences of, for instance, at least 3, 4, 5, 6, 7, 8, 9, 10, 11, 12, 13, 14, 15, 16, 17, 18, 19, 20, 21, 22, 23, 24, 25, 30, 35 or more contiguous nucleotides, including all integer values therebetween. For non-limiting examples of the design and implementation of oligonucleotide barcode sequence identification strategies, see, e.g., de Carcer et al., 2011 Adv. Env. Microbiol. 77:6310; Parameswaran et al., 2007 Nucl. Ac. Res. 35(19):330; Roh et al., 2010 Trends Biotechnol. 28:291.

Typically, barcodes are placed in oligonucleotides at locations where they are not found naturally, i.e., barcodes comprise nucleotide sequences that are distinct from any naturally occurring oligonucleotide sequences that may be found in the vicinity of the sequences adjacent to which the barcodes are situated (e.g., V and/or J sequences). Such barcode sequences may be included, according to certain embodiments described herein, as elements B1 and/or B2 of the presently disclosed oligonucleotides. Accordingly, certain of the herein described oligonucleotide compositions may in certain embodiments comprise one, two or more barcodes, while in certain other embodiments some or all of these barcodes may be absent. In certain embodiments all barcode sequences will have identical or similar GC content (e.g., differing in GC content by no more than 20%, or by no more than 19, 18, 17, 16, 15, 14, 13, 12, 11 or 10%).

Sequencing

Sequencing may be performed using any of a variety of available high through-put single molecule sequencing machines and systems. Illustrative sequence systems include sequence-by-synthesis systems such as the Illumina Genome Analyzer and associated instruments (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), Ion Torrent™ (ThermoFisher Scientific, Waltham, Mass.), or other systems having similar capabilities. Sequencing is achieved using a set of sequencing oligonucleotides that hybridize to a defined region within the amplified DNA molecules. The sequencing oligonucleotides are designed such that the V- and J-encoding gene segments can be uniquely identified by the sequences that are generated, based on the present disclosure and in view of known adaptive immune receptor gene sequences that appear in publicly available databases.

The term "gene" means the segment of DNA involved in producing a polypeptide chain such as all or a portion of an Ig polypeptide (e.g., a CDR3-containing polypeptide); it includes regions preceding and following the coding region "leader and trailer" as well as intervening sequences (introns) between individual coding segments (exons), and may also include regulatory elements (e.g., promoters, enhancers, repressor binding sites and the like), and may also include recombination signal sequences (RSSs) as described herein.

In certain embodiments, the amplified J-region or C-region encoding gene segments may each have a unique sequence-defined identifier tag of 2, 3, 4, 5, 6, 7, 8, 9, 10 or about 15, 20 or more nucleotides, situated at a defined position relative to a RSS site. However, these and related embodiments need not be so limited and also contemplate other relatively short nucleotide sequence-defined identifier tags that may be detected in J-region encoding gene segments and defined based on their positions relative to an RSS site. These may vary between different adaptive immune receptor encoding loci.

The recombination signal sequence (RSS) consists of two conserved sequences (heptamer, 5'-CACAGTG-3', and nonamer, 5'-ACAAAAACC-3'), separated by a spacer of either 12+/−1 bp ("12-signal") or 23+/−1 bp ("23-signal"). A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et. al 1994; Akamatsu et. al. 1994; Hesse et. al. 1989). Mutations of other nucleotides have minimal or inconsistent effects. The spacer, although more variable, also has an impact on recombination, and single-nucleotide replacements have been shown to significantly impact recombination efficiency (Fanning et. al. 1996; Larijani et. al 1999; Nadel et. al. 1998). Criteria have been described for identifying RSS polynucleotide sequences having significantly different recombination efficiencies (Ramsden et. al 1994; Akamatsu et. al. 1994; Hesse et. al. 1989; and Cowell et. al. 1994). Accordingly, the sequencing oligonucleotides may hybridize adjacent to a four base tag within the amplified J-encoding gene segments at positions +11 through +14 downstream of the RSS site. For example, sequencing oligonucleotides for BCRs may be designed to anneal to a consensus nucleotide motif observed just downstream of this "tag", so that the first four bases of a sequence read will uniquely identify the J-encoding gene segment (see, e.g., International PCT Publication No. WO 2012/027503).

The average length of the CDR3-encoding region, for the BCR, defined as the nucleotides encoding the BCR polypeptide between the second conserved cysteine of the V segment and the conserved phenylalanine of the J segment, is 35+/−3 nucleotides. Accordingly and in certain embodiments, PCR amplification using V-segment oligonucleotide primers with J-segment oligonucleotide primers that start from the J segment tag of a particular BCR J region (e.g., BCR JH as described herein) will nearly always capture the complete V-D-J junction in a 50 base pair read. The average length of the IGH CDR3 region, defined as the nucleotides between the conserved cysteine in the V segment and the conserved phenylalanine in the J segment, is less constrained than at the TCRβ locus, but will typically be between about 10 and about 70 nucleotides. Accordingly and in certain embodiments, PCR amplification using V-segment oligonucleotide primers with J-segment oligonucleotide primers that start from the IGH J segment tag will capture the complete V-D-J junction in a 100 base pair read.

PCR primers that anneal to and support polynucleotide extension on mismatched template sequences are referred to as promiscuous primers. In certain embodiments, the IG J-segment reverse PCR primers may be designed to minimize overlap with the sequencing oligonucleotides, in order to minimize promiscuous priming in the context of multiplex PCR. In one embodiment, the IG J-segment reverse primers may be anchored at the 3' end by annealing to the consensus splice site motif, with minimal overlap of the sequencing primers. Generally, the IG V and J-segment primers may be selected to operate in PCR at consistent annealing temperatures using known sequence/primer design and analysis programs under default parameters.

Disclosed herein are unexpectedly advantageous approaches for uniquely and unambiguously labeling individual, sequence-distinct Ig encoding gene segments or mRNA transcripts thereof, or cDNA that has been reverse transcribed from such mRNA transcripts, by performing such labeling prior to conventional steps of expanding a population of such gene segments or transcripts thereof (including reverse transcripts) through established nucleic acid amplification techniques. Without wishing to be bound by theory, by labeling individual Ig encoding gene segments or transcripts thereof (including complementary DNA generated by reverse transcription) as described herein, prior to commonly practiced amplification steps which are employed to generate DNA copies in sufficient quantities for sequencing, the present embodiments offer unprecedented sensitivity in the detection and quantification of diverse Ig encoding sequences, while at the same time avoiding misleading, inaccurate or incomplete results that may occur due to biases in oligonucleotide primer utilization during multiple rounds of nucleic acid amplification from an original sample, using a sequence-diverse set of amplification primers.

Also described herein, in certain embodiments, are unprecedented compositions and methods that permit quantitative determination of the sequences encoding both polypeptides in an adaptive immune receptor heterodimer from a single cell, such as both IGH and IGL from a B cell. By providing the ability to obtain such information from a complex sample such as a sample containing a heterogeneous mixture of T and/or B cells from a subject, these and related embodiments permit more accurate determination of the relative representation in a sample of particular T and/or B cell clonal populations than has previously been possible.

Certain embodiments contemplate modifications as described herein to oligonucleotide primer sets that are used in multiplexed nucleic acid amplification reactions to generate a population of amplified rearranged DNA molecules from a biological sample containing rearranged genes encoding adaptive immune receptors, prior to quantitative high throughput sequencing of such amplified products. Multiplexed amplification and high throughput sequencing of rearranged BCR encoding DNA sequences are described, for example, in Robins et al., 2009 *Blood* 114:4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. Patent Application Nos. 61/550,311 and 61/569,118; US Patent Application Publication Nos. US 2012-0058902 and US 2010-0330571; International PCT Publication Nos. WO 2010/151416, WO 2011/106738, and WO 2012/027503; accordingly these disclosures are incorporated by reference and may be adapted for use according to the embodiments described herein.

According to certain embodiments, in a sample containing a plurality of sequence-diverse Ig encoding gene segments, such as a sample comprising DNA (or mRNA transcribed therefrom or cDNA reverse-transcribed from such mRNA) from lymphoid cells in which DNA rearrangements have taken place to encode functional Ig heterodimers (or in which non-functional IG pseudogenes have been involved in DNA rearrangements), a plurality of individual Ig encoding sequences may each be uniquely tagged with a specific oligonucleotide barcode sequence as described herein, through a single round of nucleic acid amplification (e.g., polymerase chain reaction PCR). The population of tagged polynucleotides can then be amplified to obtain a library of tagged molecules, which can then be quantitatively sequenced by existing procedures such as those described, for example, in U.S. Patent Application Nos. 61/550,311 and 61/569,118; US Patent Application Publication Nos. US 2012-0058902 and US 2010-0330571; International PCT Publication Nos. WO 2010/151416, WO 2011/106738, and WO 2012/027503, each of which is incorporated by reference in their entireties.

In the course of these sequence reads, the incorporated barcode tag sequence is sequenced and can be used as an identifier in the course of compiling and analyzing the sequence data so obtained. In certain embodiments, it is contemplated that for each barcode tag sequence, a consensus sequence for the associated IG sequences may be determined. A clustering algorithm can then be applied to identify molecules generated from the same original clonal cell population. By such an approach, sequence data of high quality can be obtained in a manner that overcomes inaccuracies associated with sequencing artifacts.

An exemplary embodiment is depicted in FIG. 1, according to which from a starting template population of genomic DNA or cDNA from a lymphoid cell-containing population, two or more cycles of PCR are performed using an oligonucleotide primer composition that contains primers having the general formula U1-B1$_n$-X as described herein. As shown in FIG. 1, the J-specific primer 110a contains a J primer sequence 100 that is complementary to a portion of the J segment, a barcode tag (BC1) 101 in FIG. 1, or B1$_n$ in the generic formula) and also includes a first external universal adaptor sequence (U1) 102, while the V-specific primer 110b includes a V primer sequence 103 that is complementary to a portion of the V segment and a second external universal adaptor sequence (U2) 104.

The invention need not be so limited, however, and also contemplates related embodiments, such as those where the barcode may instead or may in addition be present as part of the V-specific primer and is situated between the V-sequence and the second universal adaptor. It will be appreciated that based on the present disclosure, those skilled in the art can design other suitable primers by which to introduce the herein described barcode tags to uniquely label individual IG encoding gene segments. For example, in FIG. 1, the V and J primers can each comprise a barcode (BC1, BC2) and a universal adaptor sequence (U1, U2). U1 and U2 may be the same or a different universal adaptor sequence.

As described herein, a large number (up to 4$^n$ where n is the length of the barcode sequence) of different barcode sequences are present in the oligonucleotide primer composition that contains primers having the general formula U1-B1$_n$-X as described herein, such that the PCR products of the large number of different amplification events following specific annealing of appropriate V- and J-specific primers are differentially labeled. In some embodiments, the number of barcode sequences is up to or smaller than 4$^n$. In one embodiment, a barcode of length n=8 is used. The length of the barcode "n" determines the possible number of barcodes (4$^n$ as described herein), but in some embodiments, a smaller subset is used to avoid closely related barcodes or barcodes with different annealing temperatures. In other embodiments, as described herein, sets of m and n barcode sequences are used in subsequent amplification steps (e.g., to individually label each rearranged IG sequence and then to uniformly label ("tailing") a set of sequences obtained from the same source, or sample In preferred embodiments, the V and J primers 100 and 103 are capable of promoting the amplification of an Ig encoding sequence that includes the CDR3 encoding sequence, which in FIG. 1 includes the NDN region 111. As also indicated in FIG. 1, following no more than two amplification cycles, the first amplification primer set 110a, 110b is separated from the double-stranded DNA product. By such a step, it is believed according to non-limiting theory that contamination of the product preparation by subsequent rounds of amplification is avoided, where contaminants could otherwise be produced by amplifying newly formed double-stranded DNA molecules with amplification primers that are present in the complex reaction but which are primers other than those used to generate the double-stranded DNA in the first one or two amplification cycles. A variety of chemical and biochemical techniques are known in the art for separating double-stranded DNA from oligonucleotide amplification primers.

Once the first amplification primer set 110a, 110b is removed, by which the unique barcode tag sequences have been introduced, the tagged double-stranded DNA (dsDNA) products can be amplified using a second amplification primer set 120a, 120b as described herein and depicted in FIG. 1, to obtain a DNA library suitable for sequencing. The second amplification primer set advantageously exploits the introduction, during the preceding step, of the universal adaptor sequences 102, 104 (e.g., U1 and U2 in FIG. 1) into the dsDNA products. Accordingly, because these universal adaptor sequences have been situated external to the unique barcode tags (BC1) 101 in FIG. 1, the amplification products that comprise the DNA library to be sequenced retain the unique barcode identifier sequences linked to each particular rearranged V-J gene segment combination, whilst being amenable to amplification via the universal adaptors.

In preferred embodiments and as also depicted in FIG. 1, the second amplification primer set 120a, 120b may introduce sequencing platform-specific oligonucleotide sequences (Adap1 105 and Adap2 106 in FIG. 1), however these are not necessary in certain other related embodiments. The second amplification primer set 120a, 120b may also optionally introduce a second oligonucleotide barcode identifier tag (BC2 107 in FIG. 1), such as a single barcode sequence that may desirably identify all products of the amplification from a particular sample (e.g., as a source subject-identifying code) and ease multiplexing multiple samples to allow for higher throughput. The barcode (BC2; 107 in FIG. 1) is a modification that increases the throughput of the assay (e.g., allows samples to be multiplexed on the sequencer), but is not required. Alternatively, a universal primer without adaptors can be used to amplify the tagged molecules. After amplification, the molecules can be additionally tagged with platform specific oligonucleotide sequences. Such inclusion of a second, sample-identifying barcode, may beneficially aid in the identification of sample origins when samples from several different subjects are mixed, or in the identification of inadvertent contamination of one sample preparation with material from another sample preparation. The second amplification primer set may also, as shown in FIG. 1, optionally include a spacer nucleotide ("n6"; 108 in FIG. 1), which may facilitate the operation of the sequencing platform-specific sequences. The spacer improves the quality of the sequencing data, but is not required or present in certain embodiments. The spacer is specifically added to increase the number of random base pairs during the first 12 cycles of the sequencing step of the method. By increasing the diversity of the first 12 cycles, cluster definition and base calling is improved. The spacer nucleotide 108 may be 0, 1, 2, 3, 4, 5, 6, 7, 8, 9, 10, 11-20, 21-30 or more nucleotides of any sequence, typically a randomly generated sequence. Where it may be of concern that the presence of such random sequences will result in uneven annealing rates amongst the oligonucleotide primers containing such sequences, it may be preferred to perform a relatively small number of amplification cycles, typically three, four or five cycles, or optionally 1-6 or no more than eight cycles, to reduce the potential for unevenness in amplification that could skew downstream results.

The resulting DNA library can then be sequenced according to standard methodologies and using available instrumentation as provided herein and known in the art. Where a second, sample-identifying barcode (BC2 107 in FIG. 1) is present, sequencing that includes reading both such barcodes is performed, with the sequence information (V-J junction including CDR3 encoding sequence, along with the first oligonucleotide barcode BC1 101 that uniquely tags each distinct sequence) between the two occurrences of the sample-identifying barcode 107 also being read. Sequencing primers may include, for instance, and with reference to FIG. 1, the universal primer 102 on the J side of NDN 111 for the first read, followed by a barcode sequence BC1 101, a J primer sequence 100 and CDR3 sequences. The second set of amplification primers include a forward primer comprising the platform-specific primer (Adap1 105) on the J side, a spacer sequence comprising random nucleotides (labeled "n6"; 108 in FIG. 1), and BC2 sample-identifying barcodes 107. The reverse primer in the second set of amplification primers includes the universal primer 104 on the V side of NDN 111, a spacer sequence 108 comprising random nucleotides, and a BC2 sample-identifying barcode sequence 107, and optionally a paired-end read using the reverse second sequencing platform-specific primer (Adap2 106). The second sequencing platform-specific primer (Adap2 106) is used to sequence and "read" the spacer sequence 108, the sample-identifying barcode sequence BC2 107, the universal adaptor sequence 104, the V sequence 103, and NDN 111. To capture the CDR3 sequence, one can use J amplification primers, C amplification primers or the V amplification primers.

Sequence data may be sorted using the BC2 sample-identifying barcodes 107 and then further sorted according to sequences that contain a common first barcode BC1 101. Within such sorted sequences, CDR3 sequences may be clustered to determine whether more than one sequence cluster is present using any of a known variety of algorithms for clustering (e.g., BLASTClust, UCLUST, CD-HIT, or others, or as described in Robins et al., 2009 *Blood* 114: 4099). Additionally or alternatively, sequence data may be sorted and selected on the basis of those sequences that are found at least twice. Consensus sequences may then be determined by sequence comparisons, for example, to correct for sequencing errors. Where multiple unique identifier barcode tags (BC1 101) are detected among sequences that otherwise share a common consensus sequence, the number of such barcode tags that is identified may be regarded as reflective of the number of molecules in the sample from the same T cell or B cell clone.

Identifying Both Chains of an Ig Heterodimer from a Single Adaptive Immune Cell

As also noted above, in certain other embodiments there is provided herein a method for determining rearranged DNA sequences (or mRNA sequences transcribed therefrom or cDNA that has been reverse transcribed from such mRNA) encoding first and second polypeptide sequences of an adaptive immune receptor heterodimer in a single lymphoid cell. The method includes uniquely labeling each rearranged DNA sequence with a unique barcode sequence for identifying a particular cell and/or sample, as presented in U.S. Patent Application No. 61/606,617; International PCT Publication No. WO 2014/145992; and US Patent Application Publication No. US 2015-0031043A1.

Non-limiting examples of BCR C-segment primers for 1$^{st}$ cDNA strand synthesis are shown in Table 2 and set forth in SEQ ID NOs. 23-44.

Non-limiting examples of BCR IGH and IGKL primer sequences are shown in Table 3, and set forth in SEQ ID NOs. 45-132. In one embodiment, the pGEXF sequence, SEQ ID NO: 45, and the pGEXR sequence, SEQ ID NO: 46, are added to the 5' position of primers of the present disclosure. In some embodiments, additional primer sequences are contemplated for adding to the 5' position of primers of the present disclosure, such as CMV early promoter, LKO.1, LucNrev, M13, MSCV, pBABE, SP6, T3, and T7.

TABLE 2

List of BCR C-segment primers for 1$^{st}$ cDNA strand synthesis:

| Name | Sequence | SEQ ID NO: |
|---|---|---|
| Ck | GATGAAGACAGATGGTGCAGC | 23 |
| Cl-1 | GGCGGGAACAGAGTGAC | 24 |
| Cl-2 | AGGGTGGGAACAGAGTGAC | 25 |
| Cl-3 | GCTTGAAGCTCCTCAGAGG | 26 |
| Cl-4 | GGCGGGAACAGAGTGAC | 27 |
| IgA | AGGCTCAGCGGGAAGAC | 28 |
| IgD | GAACACATCCGGAGCCTTG | 29 |
| IgE | GGTGGCATTGGAGGGAATG | 30 |
| IgG-1 | AAGACCGATGGGCCCTTG | 31 |
| IgG-2 | CTCTCGGAGGTGCTCCTG | 32 |
| IgM | AATTCTCACAGGAGACGAGGG | 33 |
| Primers from Glanville et al., PNAS 2011 | | |
| IgM_RACE | 5'-GATGGAGTCGGGAAGGAAGTCCTGTGCGAG-3' | 34 |
| IgG_RACE | 5'-GGGAAGACSGATGGGCCCTTGGTGG-3' | 35 |
| IgA_RACE | 5'-CAGGCAKGCGAYGACCACGTTCCCATC-3' | 36 |
| Igκ_RACE | 5'-CATCAGATGGCGGGAAGATGAAGACAGATGGTGC-3' | 37 |
| Igλ_RACE | 5'-CCTCAGAGGAGGGTGGGAACAGAGTGAC-3' | 38 |
| Clontech Smarter primers | | |
| Smarter UAII* | 5'-AAGCAGTGGTATCAACGCAGAGTACrGrGrGrGrG-P-3 | 39 |
| Islam UAII** | 5'-AAGCAGTGGTATCAACGCAGAGTGCAGUGCU XXXXXXrGrGrG-3' | 40 |
| Smarter CDS# | 5'-Bio-AAGCAGTGGTATCAACGCAGAGTACT (30)N$_{-1}$-N-3' | 41 |
| Smarter IS PCR# | 5'-Bio-AAGCAGTGGTATCAACGCAGAGT-3' | 42 |
| 5'RACE long | 5'-CTAATACGACTCACTATAGGGCAAGCAGTG GTATCAACGCAGAGT-3' | 43 |
| 5'RACE short | 5'-CTAATACGACTCACTATAGGGC-3' | 44 | rG = riboguanosine
N$_{-1}$ = A, C, G, or T; N = A, G, or C
X = any nucleotide
Bio = biotinylated

TABLE 3

BCR IGH and IGKL primer sequences

| Name | Sequence | SEQ ID NO: |
|---|---|---|
| pGEXF | GGGCTGGCAAGCCACGTTTGGTG | 45 |
| pGEXR | CCGGGAGCTGCATGTGTCAGAGG | 46 |
| pGEXF_IGK_V_01-05_F_D10 | TCTGCATCTGTAGGAGACAGAGTCACCATCACTTG | 47 |
| pGEXF_IGK_V_01-08_F_D10 | TCTGCATCTACAGGAGACAGAGTCACCATCACTTG | 48 |
| pGEXF_IGK_V_01-35_P_D10 | CTGCATCTGTAAGGAGACAGTGTCACCATCACTTG | 49 |
| pGEXF_IGK_V_1D-08_F_D10 | TCTGCATCTACAGGAGACAGAGTCACCATCAGTTG | 50 |
| pGEXF_IGK_V_1D-22_P_D10 | ACTGCATCTGTAGGAGAGAGAGTCACCATCACTTG | 51 |
| pGEXF_IGK_V_1D-35_P_D10 | GCATCTGTAAGGAGACAGCGTCACCATCACTTG | 52 |
| pGEXF_IGK_V_1D-42_F_D10 | GTCTGCATCTGTAGGAGACAGAGTCAGTATCATTTG | 53 |
| pGEXF_IGK_V_02-04_P_D10 | GGAGAGCCGGCCTCCATCTCCTG | 54 |
| pGEXF_IGK_V_02-10_P_D10 | CCTGGAGAGCCAGCCTCCATCTCCTG | 55 |
| pGEXF_IGK_V_02-18_P_D10 | CTGGAGAGCCGGCCTCCATCTCTTG | 56 |
| pGEXF_IGK_V_02-19_P_D10 | TCTTCCTTGGAGAGCCATCCTCCATTTCCTG | 57 |
| pGEXF_IGK_V_02-24_F_D10 | GGACAGCCGGCCTCCATCTCCTG | 58 |
| pGEXF_IGK_V_02-28_F_D10 | TGGAGAGCCGGCCTCCATCTCCTG | 59 |
| pGEXF_IGK_V_02-38_P_D10 | ATAATATTTGTACATAACTTTGTACTTCATCTCCTG | 60 |
| pGEXF_IGK_V_2D-14_P_D10 | CCCCTGGAAAGCCAGCCTCTATCTCCTG | 61 |
| pGEXF_IGK_V_2D-19_P_D10 | CTCTTCCTTGGAGAGCCATCCTCCATTTCCTG | 62 |
| pGEXF_IGK_V_2D-24_O_D10 | GGACAGCCGGCCTCCATCTCCTT | 63 |
| pGEXF_IGK_V_2D-26_F_D10 | CCTGGAGAGCAGGCCTCCATGTCCTG | 64 |
| pGEXF_IGK_V_03-07_F_D10 | CCAGGGGAAAGAGCCACCCTCTCCTG | 65 |
| pGEXF_IGK_V_03-07_P_D10 | TCCAGGGGAAAGAGTCACCCTCTCCTG | 66 |
| pGEXF_IGK_V_03-25_P_D10 | TCTTTGTCTCTGGAGAAAAAAGCCACCCTGACTTG | 67 |
| pGEXF_IGK_V_03-31_P_D10 | TCTCTAGGGAAAAAGCCACCCTCACCTA | 68 |
| pGEXF_IGK_V_03-34_P_D10 | GGGGAAGGAGCCACCCTCACCTG | 69 |
| pGEXF_IGK_V_04-01_F_D10 | GGGCGAGAGGGCCACCATCAACTG | 70 |
| pGEXF_IGK_V_05-02_F_D10 | GCGACTCCAGGAGACAAAGTCAACATCTCCTG | 71 |
| pGEXF_IGK_V_06-21_O_D10 | CTGTGACTCCAAAGGAGAAAGTCACCATCACCTG | 72 |
| pGEXF_IGK_V_6D-41_F_D10 | ACTCCAGGGGAGAAAGTCACCATCACCTG | 73 |
| pGEXF_IGK_V_07-03_P_D10 | CAGGACAGAGGGCCACCATCACCTG | 74 |
| pGEXF_IGL_V_01-36_F_D10 | CCCAGGCAGAGGGTCACCATCTCCTG | 75 |
| pGEXF_IGL_V_01-40_F_D10 | CCAGGGCAGAGGGTCACCATCTCCTG | 76 |
| pGEXF_IGL_V_01-44_F_D10 | CCGGGCAGAGGGTCACCATCTCTTG | 77 |
| pGEXF_IGL_V_01-51_F_D10 | CCCCAGGACAGAAGGTCACCATCTCCTG | 78 |
| pGEXF_IGL_V_01-62_P_D10 | CCACAAGGCAGAGGCTCACTGTCTCCTG | 79 |
| pGEXF_IGL_V_02-08_F_D10 | GTCTCCTGGACAGTCAGTCACCATCTCCTG | 80 |
| pGEXF_IGL_V_02-14_F_D10 | GTCTCCTGGACAGTCGATCACCATCTCCTG | 81 |
| pGEXF_IGL_V_02-33_O_D10 | TCCTGGACAGTCGGTCACCATCTCCTG | 82 |

TABLE 3-continued

BCR IGH and IGKL primer sequences

| Name | Sequence | SEQ ID NO: |
|---|---|---|
| pGEXF_IGL_V_02-34_P_D10 | CTGGGACTTGGGGTAAACAGTCACCATCTTCTG | 83 |
| pGEXF_IGL_V_03-01_F_D10 | CCAGGACAGACAGCCAGCATCACCTG | 84 |
| pGEXF_IGL_V_03-02_P_D10 | CTTTGGGACGTACGGCCAGGATCATCTG | 85 |
| pGEXF_IGL_V_03-04_P_D10 | CTTTGGGACAGATGGCCAGGATCACCTG | 86 |
| pGEXF_IGL_V_03-06_P_D10 | CCAGGACAGGCAGCCATGATCACCTG | 87 |
| pGEXF_IGL_V_03-07_P_D10 | TGGGACAGAGGGCCAGGATCACCTA | 88 |
| pGEXF_IGL_V_03-09_FP_D10 | GGGACAGGCGGCCAGGATTACCTG | 89 |
| pGEXF_IGL_V_03-10_F_D10 | CCAGGACAAACGGCCAGGATCACCTG | 90 |
| pGEXF_IGL_V_03-12_F_D10 | CACAGCACAGATGGCCAGGATCACCTG | 91 |
| pGEXF_IGL_V_03-13_P_D10 | CCAGGACAGACAGCCAGGATCAGCTG | 92 |
| pGEXF_IGL_V_03-15_P_D10 | CCCCAGGACAGATGACCAGGATCACCTG | 93 |
| pGEXF_IGL_V_03-16_F_D10 | CCCTAGGACAGATGGCCAGGATCACCTG | 94 |
| pGEXF_IGL_V_03-17_P_D10 | GTGTCTGTGGACAGTCAGCAAGGGTAACCTG | 95 |
| pGEXF_IGL_V_03-19_F_D10 | GGCCTTGGGACAGACAGTCAGGATCACATG | 96 |
| pGEXF_IGL_V_03-21_F_D10 | CCCCAGGAAAGACGGCCAGGATTACCTG | 97 |
| pGEXF_IGL_V_03-22_FP_D10 | CCCAGGACAGAAAGCCAGGATCACCTG | 98 |
| pGEXF_IGL_V_03-24_P_D10 | CAGTAGCTCCAGGACAGATGACTAGGATCACCTG | 99 |
| pGEXF_IGL_V_03-25_F_D10 | CAGGACAGACGGCCAGGATCACCTG | 100 |
| pGEXF_IGL_V_03-26_P_D10 | CCTGGGACAGTCAGCCAGGGTAACCTG | 101 |
| pGEXF_IGL_V_03-27_F_D10 | CGGGACAGACAGCCAGGATCACCTG | 102 |
| pGEXF_IGL_V_03-29_P_D10 | CCCAGGACAGACACCCAGGATCACCTG | 103 |
| pGEXF_IGL_V_03-30_P_D10 | CCCCATTACAGATGGCCAGGATCACCTG | 104 |
| pGEXF_IGL_V_03-31_P_D10 | GCCTTGGGATAGACAGCCAGGATCACCTG | 105 |
| pGEXF_IGL_V_03-32_O_D10 | CCTTGGGACAAATGGCCAGGATCACCTG | 106 |
| pGEXF_IGL_V_04-03_F_D10 | CTGGGAGCCTCGATCAAGCTCACCTG | 107 |
| pGEXF_IGL_V_04-60_F_D10 | CCTGGGATCCTCGGTCAAGCTCACCTG | 108 |
| pGEXF_IGL_V_04-69_F_D10 | GGGAGCCTCGGTCAAGCTCACCTG | 109 |
| pGEXF_IGL_V_05-37_F_D10 | TCCTGGAGAATCCGCCAGACTCACCTG | 110 |
| pGEXF_IGL_V_05-39_F_D10 | TCTCCTGGAGCATCAGCCAGATTCACCTG | 111 |
| pGEXF_IGL_V_05-45_F_D10 | TCCTGGAGCATCAGCCAGTCTCACCTG | 112 |
| pGEXF_IGL_V_05-48_O_D10 | TCCTGGAGCATCAGCCAGACTCACCTG | 113 |
| pGEXF_IGL_V_05-52_F_D10 | GCATCTTCTGGAGCATCAGTCAGACTCACCTG | 114 |
| pGEXF_IGL_V_07-35_P_D10 | CCCAGGAGGGACAGTCACTCTCACCTA | 115 |
| pGEXF_IGL_V_07-43_F_D10 | CCCAGGAGGGACAGTCACTCTCACCTG | 116 |
| pGEXF_IGL_V_08-61_F_D10 | CCCCTGGAGGGACAGTCACACTCACTTG | 117 |
| pGEXF_IGL_V_09-49_F_D10 | TGGGAGCCTCGGTCACACTCACCTG | 118 |
| pGEXF_IGL_V_10-54_F_D10 | CTTGAGACAGACCGCCACACTCACCTG | 119 |

TABLE 3-continued

BCR IGH and IGKL primer sequences

| Name | Sequence | SEQ ID NO: |
|---|---|---|
| PGEXF_IGK_V_del_D10 | GTAAATAATTGCATTTTTTAATGACCGTGGGTCTGTG | 120 |
| pGEXR_IGK_J_01_F_D10 | TTCTACTCACGTTTGATTTCCACCTTGGTCCC | 121 |
| pGEXr_IGKJ_02_F_D10 | AAGTACTTACGTTTGATCTCCAGCTTGGTCCC | 122 |
| pGEXr_IGK_J_03_F_D10 | ACAGATGTACTTACGTTTGATATCCACTTTGGTCCC | 123 |
| pGEXr_IGK_J_04_F_D10 | CACTTACGTTTGATCTCCACCTTGGTCCC | 124 |
| pGEXr_IGK_J_05_F_D10 | GAAAAATTACTTACGTTTAATCTCCAGTCGTGTCCC | 125 |
| pGEXr_IGL_J_01_F_D10 | CTTACCTAGGACGGTGACCTTGGTCCC | 126 |
| pGEXr_IGL_J_02_F_D10 | ACCTAGGACGGTCAGCTTGGTCCC | 127 |
| pGEXr_IGL_J_04_O_D10 | AAGAAGAGACTCATCTAAAATGATCAGCTGGGTTCC | 128 |
| pGEXr_IGL_J_05_O_D10 | ATCTAGGACGGTCAGCTCCGTCCC | 129 |
| pGEXr_IGL_J_06_F_D10 | GAGGACGGTCACCTTGGTGCC | 130 |
| pGEXr_IGL_J_07_F_D10 | AGGACGGTCAGCTGGGTGCC | 131 |
| pGEXr_IGK_del_F_D10 | CTGCAGACTCATGAGGAGTCGCCC | 132 |

High-Throughput Pairing of Rearranged Nucleic Acid Sequences Encoding Adaptive Immune Receptor Heterodimer Polypeptides In certain embodiments, the methods of the present invention include the step of determining from the combined population of cells, a plurality of cognate pairs of first and second rearranged nucleic acid sequences encoding first and second polypeptides of the adaptive immune receptor heterodimers. The present invention is not intended to be limited to any one pairing method and contemplates that many methods known in the art, including those herein disclosed, may be suitable for practicing the claimed invention.

In a preferred embodiment, the methods for determining pairs of BCR heterodimers are those described in International PCT Publication No. WO 2014/145992 which is incorporated by reference in its entirety. Other methods for pairing polypeptide chains of BCR heterodimers are described in International PCT Publication No. WO 2013/188831, which is incorporated by reference in its entirety. By way of illustration, but not limitation, one exemplary embodiment of the methods of the invention is summarized herein as follows.

The method of the invention relies on the observation that rearranged first and second nucleotide sequences are nearly unique for each clonal population of adaptive immune cells. Distinctive first and second sequences arise through recombination of gene segments and template-independent deletion or insertion of nucleotides at the V-J, V-D, and D-J junctions in somatic cells during lymphocyte development. This extraordinary diversity means that mRNAs encoding the heterodimeric polypeptide chains of a specific adaptive immune cell clone will usually be present only in sets of cells that include that clone. This extreme diversity may be leveraged by splitting a sample of adaptive immune cells into multiple subsets and then sequencing the first and second mRNA molecules to determine the presence or absence of each polypeptide chain in each subset. The first and second sequences from a clone should be seen in the same subsets of adaptive immune cells, and only those subsets.

In some embodiments, the method can involve extracting genomic DNA, rather than mRNA from cells in a sample, to amplify up the polypeptide chains of a specific adaptive immune receptor heterodimer.

Pairing the heterodimeric polypeptide chains then becomes a statistical problem: to declare a unique pairing, one must show that it is highly improbable for a given clone to occupy the same collection of adaptive immune cell subsets as another clone. The probability that a given clone occupies the same collection of adaptive immune cell subsets as another clone is close to zero for thousands of clones in an experiment using the methods of the invention.

In other embodiments, the method of the invention can be tuned to pair cognate adaptive immune receptor chains in any desired frequency range simply by changing the number of input adaptive immune cells per well. Other embodiments can also assay cognate pairs from multiple frequency bands in a single experiment by stratifying the number of input adaptive immune cells into subsets.

As described above, the method can be used to accurately pair BCR sequences at high-throughput. For example, the methods of the invention can be used to pair a first polypeptide chain of an adaptive immune receptor heterodimer comprising a BCR light chain and a second polypeptide of the adaptive immune receptor heterodimer comprising a BCR heavy chain. In another example, the methods of the invention can be used to pair a first polypeptide of an adaptive immune receptor heterodimer comprising an immunoglobulin heavy (IGH) chain and a second polypeptide of the adaptive immune receptor heterodimer that is selected from an immunoglobulin light IGL or an IGK chain.

The method provides steps for identifying a plurality of cognate pairs comprising a first polypeptide and a second polypeptide that form an adaptive immune receptor heterodimer, said adaptive immune receptor heterodimer comprising a B cell receptor (BCR) from a single clone in a sample, the sample comprising a plurality of lymphoid cells from a mammalian subject. As described above, the method includes steps for distributing a plurality of lymphoid cells among a plurality of containers, each container comprising a plurality of lymphoid cells; generating a library of amplicons in the plurality of containers by performing multiplex PCR of cDNA molecules that have been reverse-transcribed from mRNA molecules obtained from the plurality of lymphoid cells. The library of amplicons include: i) a plurality of first adaptive immune receptor amplicons encoding the first polypeptide, each comprising a unique variable (V) region encoding sequence, a unique J region encoding sequence or both a unique J region encoding sequence and a unique C region encoding sequence, at least one barcode sequence, at least one universal adaptor sequence, and a sequencing platform tag sequence, and ii) a plurality of second adaptive immune receptor amplicons encoding the second polypeptide, each comprising a unique V region encoding sequence, a unique J region encoding sequence or both a unique J region encoding sequence and a unique C region encoding sequence, at least one barcode sequence, at least one universal adaptor sequence, and a sequencing platform tag sequence. The method also includes steps for performing high-throughput sequencing of the library of amplicons to obtain a data set of a plurality of first and second adaptive immune receptor amplicon sequences.

In addition, the method includes determining a container occupancy pattern for each unique first adaptor immune receptor amplicon sequence by assigning each unique first adaptor immune receptor amplicon sequence to one or more containers, and a container occupancy pattern for each unique second adaptor immune receptor amplicon sequence by assigning each unique second adaptor immune receptor amplicon sequence to one or more containers, wherein each barcode sequence in the unique first or second adaptor immune receptor amplicon sequences is associated with a particular container.

For each possible pairing of a unique first and second adaptive immune receptor amplicon sequence to form a putative cognate pair, the method involves calculating a statistical probability of observing the container occupancy patterns, or observing any larger proportion of shared containers than expected by chance, given that the first and second adaptor immune receptor amplicon sequences do not originate from the same clonal population of lymphoid cells, and identifying a plurality of a putative cognate pairs based on the statistical probability having a score lower than a predetermined likelihood cutoff.

Then, for each identified putative cognate pair, a false discovery rate estimation can be determined for a possible false pairing of the unique first adaptor immune receptor amplicon sequence and the unique second adaptor immune receptor amplicon sequence. The method includes steps for identifying a plurality of cognate pairs of unique first and second adaptive immune receptor sequences as true cognate pairs that encode said adaptive immune receptors in said sample based on said statistical probability and said false discovery rate estimation.

In some embodiments, the statistical score can be a p-value calculated for pairing each putative cognate pair of unique first and second adaptive immune receptor amplicon sequences. In one embodiment, calculating the statistical score comprises calculating a probability that the unique first and second adaptive immune receptor amplicon sequences should jointly occupy as many or more containers than they are observed to jointly occupy, assuming no true cognate pairing and given the number of containers occupied by said unique first adaptive immune receptor amplicon sequence and the number of containers occupied by the unique second adaptive immune receptor amplicon sequence.

Essentially, given any two adaptive immune receptor sequences, the method analyzes whether the two sequences co-occur in more containers than would be expected by chance. Given a total of N containers, a first adaptive immune receptor sequence (A) observed in a total of X containers, a second adaptive immune receptor sequence (B) observed in a total of Y containers, and Z containers in which both adaptive immune receptor sequences (A) and (B) are observed, the method provides that given sequence (A) is found in X out of N containers (X I N) and sequence (B) is found in Y out of N (Y I N) containers, a calculation of the probability that both sequences are found in Z or more containers.

In some embodiments, the lower the probability that the observed number of overlapping containers between A and B sequences could occur by chance, the more highly likely that their co-occurrence is not by chance, but is instead due to true cognate pairing.

Next, identifying a plurality of a putative cognate pairs that have a high likelihood of pairing based on the statistical probability can comprise for each unique first adaptor immune receptor amplicon sequence identifying the unique second adaptor immune receptor amplicon sequence that has the lowest p-value score of matching, or for each unique second adaptor immune receptor amplicon sequence finding the unique first adaptor immune receptor amplicon sequence that has the lowest p-value score of matching.

In other embodiments, determining a false discovery rate estimation comprises: calculating p-values for each of the plurality of putative cognate pairs identified in the sample; comparing the p-values for all of the plurality of putative cognate pairs with an expected p-value distribution, said expected p-value distribution calculated to represent an experiment where no true cognate pairs are present; and determining for each putative cognate pair, an expected proportion of false positive results such that all p-values at or below the p-value of the putative cognate pair are determined to represent a true cognate pairing.

In certain embodiments, calculating the expected p-value distribution comprises: permuting the containers in which each first and second adaptive immune receptor sequence has been observed in an otherwise-identical experiment with no true cognate pairs, and calculating the distribution of p-values associated with each putative cognate pair.

The method includes identifying a plurality of cognate pairs of unique first and second adaptive immune receptor sequences as true cognate pairs by selecting a plurality of putative cognate pairs that have p-values below a threshold calculated based on the false discovery rate estimation.

In one embodiment, the identified cognate pair of unique first and second adaptive immune receptor amplicon sequences has a false discovery rate estimation of less than 1%. In other embodiments, the identified cognate pair of unique first and second adaptive immune receptor amplicon sequences has a false discovery rate estimation of less than 2%, 3%, 4%, 5%, 6%, 7%, 8%, 9%, or 10%.

The method can also include contacting each of said plurality of containers, under conditions and for a time sufficient to promote reverse transcription of mRNA molecules obtained from said plurality of lymphoid cells, with a first reverse transcription primer set. In certain embodiments, the (A) first oligonucleotide reverse transcription primer set comprises primers capable of reverse transcribing a plurality of mRNA sequences encoding the plurality of first and second adaptive immune receptor polypeptides for generating a plurality of first and second reverse-transcribed adaptive immune receptor cDNA amplicons, wherein the plurality of first reverse-transcribed adaptive immune receptor cDNA amplicons encoding the first adaptive immune receptor polypeptide comprise 1) a unique V region encoding gene sequence, and 2) a unique J region encoding gene sequence or both a unique J region encoding gene sequence and a unique C region encoding gene sequence, and wherein the plurality of second reverse-transcribed adaptive immune receptor cDNA amplicons encoding the second adaptive immune receptor polypeptide comprise 1) a unique V region encoding gene sequence, and 2) a unique J region encoding gene sequence or both a unique J region encoding gene sequence and a unique C region encoding gene sequence.

The first and second reverse-transcribed adaptive immune receptor cDNA amplicons are then amplified in a second reaction. The reaction begins by contacting each of said plurality of containers, under conditions and for a time sufficient to promote a multiplex PCR amplification of the first and second reverse-transcribed adaptive immune receptor cDNA amplicons with a second (B) and third (C) oligonucleotide primer sets. In some aspects, the (B) second oligonucleotide primer set comprises forward and reverse primers capable of amplifying the plurality of first reverse-transcribed adaptor immune receptor cDNA amplicons, wherein said forward and reverse primers each are capable of hybridizing to the first reverse-transcribed adaptive immune receptor cDNA amplicons.

Each pair of forward and reverse primers in the second oligonucleotide primer set is capable of amplifying the first reverse-transcribed adaptive immune receptor cDNA amplicons. The forward primers in the second oligonucleotide primer set comprise a first universal adaptor sequence and a region complementary to the V region encoding gene sequence. The reverse primers in the second oligonucleotide primer set comprise a second universal adaptor sequence and a region complementary to the J region encoding gene sequence or the C region encoding gene sequence.

The (C) third oligonucleotide primer set comprises forward and reverse primers capable of amplifying the plurality of reverse-transcribed second adaptive immune receptor cDNA amplicons. Each pair of forward and reverse primers in the third oligonucleotide primer set is capable of amplifying the second reverse-transcribed adaptive immune receptor cDNA amplicons. In one aspect, the forward primers in the third oligonucleotide primer set comprise a first universal adaptor sequence and a region complementary to the V region encoding gene sequence. The reverse primers in the third oligonucleotide primer set comprise a second universal adaptor sequence and a region complementary to the J region encoding gene sequence or complementary to the C region encoding gene sequence.

The method also includes generating i) a plurality of third adaptive immune receptor amplicons each comprising a unique V region encoding gene sequence, or complement thereof, a unique J region encoding gene sequence or both a unique J region encoding gene sequence and a unique C region encoding gene sequence, or complement thereof, and the first and second universal adaptor sequences, and ii) a plurality of fourth adaptive immune receptor amplicons each comprising a unique V region encoding gene sequence, or complement thereof, a unique J region encoding gene sequence or both a unique J region encoding gene sequence and a unique C region encoding gene sequence, or complement thereof, and the first and second universal adaptor sequences.

The plurality of third adaptive immune receptor amplicons and the plurality of fourth adaptive immune receptor amplicons are then amplified with additional primers. The method includes contacting each of the plurality of containers, under conditions and for a time sufficient to promote a second multiplex PCR amplification of the plurality of third and fourth adaptive immune receptor amplicons with a fourth (D) oligonucleotide primer set and fifth (E) oligonucleotide primer set.

In one embodiment, the (D) fourth oligonucleotide primer set comprises forward and reverse primers capable of amplifying the plurality of third adaptor immune receptor amplicons, wherein the forward and reverse primers each are capable of hybridizing to the third adaptive immune receptor amplicons. Each pair of forward and reverse primers in the fourth oligonucleotide primer set is capable of amplifying said third adaptor immune receptor amplicons.

The forward primer in the fourth oligonucleotide primer set comprises a sequencing platform tag sequence and a region complementary to the first universal adaptor sequence in the plurality of third adaptive immune receptor amplicon and the reverse primer comprises a sequencing platform tag sequence and a region complementary to the second universal adaptor sequence in the plurality of third adaptive immune receptor amplicons. In another embodiment, either one or both of the forward and reverse primers in the fourth oligonucleotide primer set comprises a unique barcode sequence associated with the container in which the fourth oligonucleotide primer set is introduced.

The (E) fifth oligonucleotide primer set comprises forward and reverse primers capable of amplifying the plurality of fourth adaptor immune receptor amplicons, wherein the forward and reverse primers each are capable of hybridizing to the fourth adaptive immune receptor amplicons. Each pair of forward and reverse primers in said fourth oligonucleotide primer set is capable of amplifying said plurality of fourth adaptor immune receptor amplicons. The forward primer in the fifth oligonucleotide primer set comprises a sequencing platform tag sequence and a region complementary to the first universal adaptor sequence in the plurality of fourth adaptive immune receptor amplicons, and the reverse primer in the fifth oligonucleotide primer set comprises a sequencing platform tag sequence and a region complementary to the second universal adaptor sequence in the plurality of fourth adaptive immune receptor amplicons.

Either one or both of the forward and reverse primers of the fourth oligonucleotide primer set comprises a unique barcode sequence associated with the container in which the fourth oligonucleotide primer set is introduced, thereby generating the library of amplicons comprising the plurality of first adaptive immune receptor amplicons and the plurality of second adaptive immune receptor amplicons.

Next, the method includes combining the library of amplicons from the plurality of containers into a mixture for sequencing. Methods for high-throughput sequencing are described in detail above and in U.S. Patent Application Publication Nos. US 2012-0058902 and US 2010-0330571; and International PCT Publication Nos. WO 2011/106738 and WO 2012/027503, each of which are incorporated by reference in their entireties.

In one aspect, the plurality of first adaptive immune receptor amplicons comprise a C region encoding sequence. In some aspects, the plurality of second adaptive immune receptor amplicons comprise a C region encoding sequence.

In some cases, the sample comprises a blood sample. In another embodiment, the sample comprises a tissue sample. In certain embodiments, the sample comprises a sample purified or cultured human lymphoid cells. In other embodiments, the container comprises at least 104 lymphoid cells. In another embodiment, the sample comprises at least 104 cells.

The method is applicable to various adaptive immune receptor loci, as described above, such as pairing of a BCR heavy chain and a BCR light chain, or an IGK chain.

Where the first polypeptide of the adaptive immune receptor heterodimer is an IGH chain and the second polypeptide of the adaptive immune receptor heterodimer is both IGL and IGK, then three different amplification primer sets are used comprising: a first oligonucleotide amplification primer set for IGH, a second oligonucleotide amplification primer set for IGK, and a third oligonucleotide amplification primer set for IGL.

Thus, the methods and compositions of the invention can be found useful in many applications in immunology, medicine, and therapeutic development. The methods of the invention offer opportunities for investigating connections between the primary sequences of a collection of selected immune receptors and the target(s) (and epitopes) that caused their selection. With attention to experimental design and control of variables (e.g., HLA type), the methods of the invention can be a useful approach for identifying critical BCRs from tumor-infiltrating lymphocytes, for establishing new criteria for responsiveness to routine or experimental vaccination, and for epidemiological analysis of public exposures and shared responses. The methods of the invention also provide information on the relative contribution of each independent chain to a given response. In addition, our approach provides data on whether there might be physical BCR chain attributes that govern a particular immune response. For example, constraints on the length or biophysical parameters of one or both chains for a given type of response to a given type of antigenic challenge. The methods of the invention can be run with standard laboratory supplies and equipment, without the need for specialized expertise, and the starting sample type has a broad potential range (tumor samples, sorted cells, cells in suspension, etc.). This technology is designed to be scalable and accessible to a variety of laboratories.

It is important to recognize that the methods of the invention can be applied to and will work equally well with BCR heavy and light chains (IGH with IGK or IGL). Given the practical interest in monoclonal antibody development, as well as the general importance of the humoral immune response, the methods of the invention have the potential to become an important technology for biomedical discovery.

Combination of BCR Heterodimer High-Throughput Pairing with Identification of BCR Antigen-Specificity In one embodiment, an antigen library of interest is created in an M13 phage display library, wherein cDNA encoding the antigens are ligated to a phage gene encoding the minor or major coat protein. In one embodiment, the gene encoding the minor coat protein is pIII, and the gene encoding the major coat protein is pVIII.

In one embodiment, said phage gene is introduced into a host bacterial cell for rapid reproduction of the host cell comprising the phage gene. In a further embodiment, once adequate bacterial growth has occurred, the bacterial cells are lysed and mature phage are isolated and washed in a buffered solution.

In one embodiment, the cDNA encoding the antigens is at least 9 base pairs (bp), 12 bp, 15 bp, 18 bp, 21 bp, 24 bp, 27 bp, 30 bp, 33 bp, 36 bp, 37 bp, 40 bp, 43 bp, 46 bp, 49 bp, 60 bp, 90 bp, 120 bp, 150 bp, 270 bp, 360 bp, 480 bp, 540 bp, or 660 bp in length.

In one embodiment, the cDNA encoding the antigens are flanked by a synthetic polynucleotide sequence, and wherein the synthetic polynucleotide sequence comprises at least one barcode sequence, at least one universal adaptor sequence, and at least one sequencing platform tag sequence. In some embodiments, the synthetic polynucleotide sequences flanking the cDNA encoding the antigens all share at least one common primer binding site. In some embodiments, the synthetic polynucleotide sequences flanking the cDNA encoding the antigens each comprise a unique tag or barcode.

In one embodiment, each synthetic polynucleotide sequence is at least 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, 125 bp, 150 bp, 175 bp, 200 bp, 250 bp, 300 bp, 400 bp, 500 bp, or 650 bp in length.

In one embodiment, B-cells comprising extracellular B-cell receptors (BCRs) are isolated from a host and washed at least twice in a buffered solution. In a further embodiment, the B-cells are added to a buffered solution comprising phage of the phage display library, wherein the solution is mixed for a period of at least 5 hours at either 25° C. or 37° C. At the end of the mixing period, B-cells are enriched for those that have phage bound to the BCR. In one embodiment, the enrichment is carried out with the use of flow cytometry.

In one embodiment, the B-cells are introduced into the solution at a B-cell:phage ratio of at least 1:5, 1:6, 1:7, 1:8, 1:9, 1:10, 1:11, 1:12, 1:13, 1:14, 1:15, 1:16, 1:17, 1:17, 1:19, 1:20, 1:25, 1:30, 1:35, 1:40, 1:45, 1:50, 1:60, 1:70, 1:80, 1:90, 1:100, 1:125, 1:150, 1:175, 1:200, 1:300, 1:400, 1:500, 1:750, or 1:1,000.

In one embodiment, the B-cells bound to antigens of the phage display library are distributed into a plurality of aliquots. In further embodiments, mRNA from B-cells bound to antigens of the phage display library are isolated, as are nucleic acids from the phage. For each aliquot, reverse transcription primers, as described herein, are utilized to reverse transcribe mRNA comprising rearranged CDR3 regions of the B-cells that direct incorporation of an oligonucleotide barcode and a universal adapter resulting in cDNA from each of the light and heavy chain sequences comprising a barcode and a universal adaptor, wherein each of the oligonucleotide reverse transcription primers that are contacted with the contents of a single aliquot share at least one common barcode sequence.

In one embodiment, the reverse transcription primers hybridize to the V, J, or C segments of each rearranged DNA sequence encoding a light chain and/or a heavy chain.

In one embodiment, as described herein, amplification primers that hybridize to the universal adaptor sequence are used to amplify the light and heavy chain cDNA sequences. In one embodiment, the amplified light and heavy chain cDNA sequences are quantitatively sequenced to obtain a data set of sequences that includes the B-cell light and heavy chain sequences and associated barcodes for each aliquot.

In one embodiment, the sequenced amplification products are sorted based on the unique barcode to identify light and heavy chain sequences that were amplified from the same aliquot and determining an aliquot occupancy pattern for each unique light and heavy chain sequence. In a further embodiment, the light and heavy chain sequences that are paired are identified based on whether the sequences occur together or do not occur together in a plurality of aliquots based on a statistical probability of observing said aliquot occupancy pattern.

In one embodiment, the nucleic acids isolated from the phage are sequenced, and the paired light and heavy chain sequences previously identified are used to determine whether the antigen encoding sequences are matched to the paired BCR heterodimer based on whether or not the sequences occur together in a plurality of aliquots.

The methods of identifying antigen-specific B-cell receptors can be found useful not only in the ability to begin developing an immune repertoire library that correlates to known antigenic sequences, but in the multitude of applications in immunology, medicine, and patient care. Such a method allows for the surveillance of the BCR repertoire of any given patient and making a quick evaluation of an acute or chronic state of disease with sensitivity and speed of assessment both considerably greater than methods presently known in the art. The methods of the invention offer opportunities for investigating the creation of chimeric BCR receptors as well as adoptive transfers of known disease-fighting B-cells expressing a desirable receptor in the treatment of disease. The methods of the invention can be run with standard laboratory supplies and equipment, without the need for specialized expertise, and the starting sample type has a broad potential range (tumor samples, sorted cells, cells in suspension, etc.). This technology is designed to be scalable and accessible to a variety of laboratories.

It is important to recognize that the methods of the invention can be applied to and will work equally well with BCR heavy and light chains (IGH with IGK or IGL). Given the practical interest in monoclonal antibody development, as well as the general importance of the humoral immune response, the methods of the invention have the potential to become an important technology for biomedical discovery.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or suggestion in any form that they constitute valid prior art or form part of the common general knowledge in any country in the world.

The invention claimed is:

1. A method for identifying antigen-specific B-cell receptor (BCR) sequences comprising:
   (A) incubating a plurality of B-cells with an antigen library displayed by an organism capable of displaying antigens;
   (B) distributing the B-cells bound to antigens of the antigen library into a plurality of aliquots;
   (C) isolating nucleic acids from B-cells bound to antigens of the antigen library and from the organism displaying said antigens;
   (D) sequencing the following elements from each of the aliquots;
      (i) B-cell heavy chain sequence,
      (ii) B-cell light chain sequence, and
      (iii) a nucleotide sequence encoding the antigen bound to the BCR; and (E) identifying the sequenced elements of (D) that occur together in more than one aliquot thereby identifying antigen-specific BCR sequences.

2. The method of claim 1, wherein (A) is immediately followed by enriching for B-cells bound to species of the antigen library.

3. The method of claim 2, wherein enriching for B-cells bound to species of the antigen library comprises flow cytometry.

4. The method of claim 1, wherein (C) is immediately followed by generating a library of amplicons by performing multiplex PCR on the isolated nucleic acids.

5. The method of claim 1, wherein the plurality of B-cells are isolated from a human.

6. The method of claim 1, wherein a plurality of B-cells comprises at least $10^4$ cells.

7. The method of claim 1, wherein said antigen library is a phage display library, a bacterial surface display library, or a yeast surface display library.

8. The method of claim 7, wherein said antigen library is a phage display library, and wherein the phage is selected from the group consisting of T7, M13, fd, f1, T4, and Lambda.

9. The method of claim 1, wherein said antigen library comprises antigens selected from the group consisting of bacterial antigens, viral antigens, fungal antigens, protist antigens, plant antigens, vertebrate antigens, mammalian antigens, and any combination thereof.

10. The method of claim 1, wherein the antigen library comprises a whole-genome library of an organism.

11. The method of claim 10, wherein the organism is a mammalian pathogen.

12. The method of claim 11, wherein the mammalian pathogen is a human pathogen.

13. The method of claim 1, wherein the B-cells express BCRs on the cell surface.

14. The method of claim 1, wherein the antigen library comprises a plurality of antigens, and wherein the nucleotide sequence encoding each antigen is flanked by a synthetic polynucleotide sequence.

15. The method of claim 14, wherein the synthetic polynucleotide sequence comprises at least one barcode sequence.

16. The method of claim 14, wherein the synthetic polynucleotide sequence comprises at least one universal adaptor sequence flanking the antigen.

17. The method of claim 14, wherein the synthetic polynucleotide comprises at least one universal adaptor sequence, a sequencing platform tag sequence, and at least one barcode sequence.

18. The method of claim 1, wherein the nucleotide sequence encoding the antigen is a cDNA.

19. The method of claim 1, further comprising:
(i) for each aliquot, reverse transcribing mRNA comprising rearranged CDR3 regions of the B-cells using oligonucleotide reverse transcription primers that direct incorporation of an oligonucleotide barcode and a universal adapter resulting in cDNA from each of the light and heavy chain sequences comprising a barcode and a universal adaptor, such that amplicons in an aliquot comprises the same unique barcode;
(ii) amplifying the cDNA using amplification primers to obtain amplification products;
(iii) quantitatively sequencing the amplification products of (ii) to obtain a data set of sequences that includes the B-cell light and heavy chain sequences and associated barcodes for each aliquot;
(iv) sorting amplification products based on the unique barcode to identify light and heavy chain sequences that were amplified from the same aliquot and determining an aliquot occupancy pattern for each unique light and heavy chain sequence; and
(v) identifying light and heavy chain sequences as paired immune receptor chains based on whether the sequences occur together or do not occur together in a plurality of aliquots based on a statistical probability of observing said aliquot occupancy pattern.

20. The method of claim 19, wherein each of the oligonucleotide reverse transcription primers that are contacted with the contents of a single aliquot share a common barcode sequence.

21. The method of claim 19, wherein the amplification primers further comprise an additional barcode, an n6 spacer, and/or a sequencing oligonucleotide.

22. The method of claim 19, wherein the amplification primers specifically hybridize to the universal adapter added to the cDNA in step (ii).

23. The method of claim 19, wherein the reverse transcription primers specifically hybridize to V, J, or C segments of each rearranged DNA sequence encoding a light chain and heavy chain polypeptide.

24. The method of claim 23 further comprising clustering the sorted amplification products in step (iv) based on the V, J, and/or C segments of each rearranged DNA sequence.

25. A method for identifying antigen-specific B-cell receptor (BCR) sequences comprising:
(A) incubating a plurality of B-cells with a phage antigen display library;
(B) distributing the B-cells bound to antigens of the antigen library into a plurality of aliquots;
(C) isolating mRNA from B-cells bound to antigens of the antigen library and nucleic acids from the phage;
(D) for each aliquot, reverse transcribing mRNA comprising rearranged CDR3 regions of the B-cells using oligonucleotide reverse transcription primers that direct incorporation of an oligonucleotide barcode and a universal adapter resulting in cDNA from each of the light and heavy chain sequences comprising a barcode and a universal adaptor, wherein each of the oligonucleotide reverse transcription primers that are contacted with the contents of a single aliquot share a common barcode sequence;
(E) amplifying the light and heavy chain cDNA sequences using amplification primers to obtain amplification products;
(F) quantitatively sequencing the amplification products of (E) to obtain a data set of sequences that includes the B-cell light and heavy chain sequences and associated barcodes for each aliquot;
(G) sorting amplification products based on the unique barcode to identify light and heavy chain sequences that were amplified from the same aliquot and determining an aliquot occupancy pattern for each unique light and heavy chain sequence;
(H) identifying light and heavy chain sequences as paired immune receptor chains based on whether the sequences occur together or do not occur together in a plurality of aliquots based on a statistical probability of observing said aliquot occupancy pattern;
(I) generating a library of amplicons by performing PCR on the isolated nucleic acids from the phage, followed by sequencing the library of amplicons; and (J) identifying the paired immune receptor chains in (H) and the nucleic acids in (I) based on whether the sequences occur together or do not occur together in a plurality of aliquots.

26. The method of claim 25, wherein the amplification primers further comprise an additional barcode, an n6 spacer, and/or a sequencing oligonucleotide.

27. The method of claim 25, wherein the amplification primers specifically hybridize to the universal adapter added to the cDNA in (E).

28. The method of claim 25, wherein the reverse transcription primers specifically hybridize to V, J, or C segments of each rearranged DNA sequence encoding a light chain and heavy chain polypeptide.

29. The method of claim 25 further comprising clustering the sorted amplification products in (G) based on the V, J, and/or C segments of each rearranged DNA sequence.

30. The method of claim 25, wherein the isolated nucleic acids from the phage comprise RNA, step (I) is immediately preceded by reverse transcribing RNA comprising antigens of the antigen display library.

* * * * *